US012674176B2

(12) United States Patent
Cerf et al.

(10) Patent No.: US 12,674,176 B2
(45) Date of Patent: Jul. 7, 2026

(54) INSECTICIDAL PROTEINS AND METHODS FOR THEIR USE

(71) Applicant: PIONEER HI-BRED INTERNATIONAL, INC., Johnston, IA (US)

(72) Inventors: David Charles Cerf, Palo Alto, CA (US); Steven D Gruver, Pacifica, CA (US); Lu Liu, Palo Alto, CA (US); Young-Jun Park, Fremont, CA (US); Ute Schellenberger, Palo Alto, CA (US); Jun-Zhi Wei, Johnston, IA (US); Weiping Xie, East Palo Alto, CA (US); Genhai Zhu, San Jose, CA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 18/650,291

(22) Filed: Apr. 30, 2024

(65) Prior Publication Data

US 2025/0011806 A1     Jan. 9, 2025

Related U.S. Application Data

(62) Division of application No. 17/283,042, filed as application No. PCT/US2019/055409 on Oct. 9, 2019, now abandoned.

(60) Provisional application No. 62/743,784, filed on Oct. 10, 2018.

(51) Int. Cl.
| | |
|---|---|
| C07K 14/195 | (2006.01) |
| C12N 5/04 | (2006.01) |
| C12N 15/82 | (2006.01) |

(52) U.S. Cl.
CPC ........ *C12N 15/8286* (2013.01); *C07K 14/195* (2013.01); *C12N 5/04* (2013.01); *C07K 2319/02* (2013.01)

(58) Field of Classification Search
None
See application file for complete search history.

(56) References Cited

U.S. PATENT DOCUMENTS

| | | | |
|---|---|---|---|
| 9,879,277 B2 | 1/2018 | Abad et al. | |
| 2006/0191034 A1 | 8/2006 | Baum et al. | |
| 2014/0283208 A1 | 9/2014 | Abad et al. | |
| 2021/0251240 A1* | 8/2021 | Reynolds et al. | ..... A01N 63/50 |
| 2023/0183734 A1 | 6/2023 | Cerf et al. | |

FOREIGN PATENT DOCUMENTS

| | | |
|---|---|---|
| WO | 2014008054 A2 | 1/2014 |
| WO | 2014159836 A1 | 10/2014 |
| WO | 2016186986 A1 | 11/2016 |
| WO | 2017192560 A1 | 11/2017 |
| WO | 2018075350 A1 | 4/2018 |

OTHER PUBLICATIONS

Webster et al., Synthetic gene design—The rationale for codon optimization and implications for molecular pharming in plants, (2017), Biotechnology and Bioengineering, vol. 114(3), pp. 492-502 (Year: 2017).*
Schellenberger et al., A selective insecticidal protein from Pseudomonas for controlling corn rootworms, 2016, Science, vol. 354(6312), pp. 634-637 (Year: 2016).*
Vesga et al., Phylogenetically closely related pseudomonads isolated from arthropods exhibit differential insect-killing abilities and genetic variations in insecticidal factors, 2021, Environmental Microbiology, vol. 23(9), pp. 5378-5394 (Year: 2021).*
Wei et al., Novel insecticidal proteins from ferns resemble insecticidal proteins from Bacillus thuringiensis, 2023, PNAS, vol. 120(44), pp. 1-7 (Year: 2023).*
Anonymous: "AC A4BUR1," Apr. 3, 2007, XP055962170, Retrieved on [Sep. 19, 2022] Retrieved from URL: https://rest.uniprot.org/uniprotkb/A4BUR1.txt.
Extended European Search Report for European Application No. 19870323.3, mailed Oct. 4, 2022, 11 Pages.
Fussel J., et al., Adaptability as the Key to Success for the Ubiquitous Marine Nitrite Oxidizer Nitrococcus, Science Advances, 2017, vol. 3, No. 11, pp. 1-9.

(Continued)

*Primary Examiner* — Amjad Abraham
*Assistant Examiner* — Christina L Meadows

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of bacterial species. The sequences find use in the construction of expression vectors for subsequent transformation into organisms of interest including plants, as probes for the isolation of other homologous (or partially homologous) genes. The pesticidal proteins find use in controlling, inhibiting growth or killing Lepidopteran, Coleopteran, Dipteran, fungal, Hemipteran and nematode pest populations and for producing compositions with insecticidal activity.

15 Claims, No Drawings

Specification includes a Sequence Listing.

(56) References Cited

OTHER PUBLICATIONS

International Preliminary Report on Patentability for International Application No. PCT/US2019/055409, mailed Apr. 22, 2021, 8 Pages.

International Search Report and Written Opinion for International Application No. PCT/US2019/055409, mailed Feb. 21, 2020, 15 Pages.

Partial Supplementary European Search Report for European Application No. 19870323.3, mailed May 17, 2022, 10 Pages.

Webster G.R., et al., "Synthetic Gene Design—The rationale for Codon Optimization and Implications for Molecular Pharming in Plants," Biotechnology and Bioengineering, 2017, vol. 114, No. 3, pp. 492-502.

* cited by examiner

SEQUENCE LISTING

```
Sequence total quantity: 82
SEQ ID NO: 1               moltype = AA   length = 289
FEATURE                    Location/Qualifiers
source                     1..289
                           mol_type = protein
                           organism = Pseudomonas vranovensis
SEQUENCE: 1
MAISIAINAG QSSSASTVIA TGTVQNVITD TERTLFNIQD GSLKAAVSAY FGRSPNDAYV  60
CSPTPWGDLY QTYNWPQVQA TLSVVSARIV SETSNPIALN TNTFTNHSSV PAEFNCGVTQ  120
EVTVTAESNW SSSSEVGISQ TISYGISFLG AGAQGETALS FTQTWEQGGS QSESVTLGSS  180
AGVTLTLQPG QTVEAILSAS KGVLTVEVEY QITLAGVTAV NYNPTYQGHH FWALDINNVM  240
SAGKLSNVIT SKETIVIDYF TNTTITVQDP ESQDVIRTLV TSARPGISS              289

SEQ ID NO: 2               moltype = AA   length = 289
FEATURE                    Location/Qualifiers
source                     1..289
                           mol_type = protein
                           organism = Pseudomonas vranovensis
SEQUENCE: 2
MAISIAINAG QSSSASTVIA TGTVQNVITD TERTLFNIQD GSLKAAVSAY FGRSPNDAYV  60
```

-continued

```
CSPTPWGDLY QTYNWPQVQA TLSVVSARIV SETSNPIALN TNTFTNHSSV PAEFNCGVTQ    120
EVTVTAESNW SSSSEVGISQ TISYGISFLG AGAQGETALS FTQTWEQGGS QSESVTLGSS    180
AGVALTLQPG QTVEAILSAS KGVLTVEVEY QITLAGVTAV NYNPTYQGHH FWTLDINNVM    240
SAGKLSNVIT SKETIVIDYF TNTTITVQDP ESQDVIRTLV TSVRPGISS               289

SEQ ID NO: 3            moltype = AA   length = 289
FEATURE                 Location/Qualifiers
REGION                  1..289
                        note = XM21_pooled_NODE_1357_58
source                  1..289
                        mol_type = protein
                        organism = unidentified
SEQUENCE: 3
MAISIAINAG QSSSASTVIA TGTVQNVITD TERTLFNIQD GSLKAAVSAY FGRSPNDAYV    60
CSPTPWGDLY QTYNWPQVQA TLSVVSARIV SETSNPIALN TNTFTNHSSV PAEFNCGVTQ    120
EVTVTAESNW SSSSEVGISQ TISYGISFLG AGAQGETALS FTQTWEQGGS QSESVTLGSS    180
AGVALTLQPG QTVEAILSAS KGVLTVEVEY QITLAGVTAV NYNPTYQGHH FWALDINNVM    240
SAGKLSNVIT SKETIVIDYF TNTTITVQDP ESQDVIRTLV TSARPGISS               289

SEQ ID NO: 4            moltype = AA   length = 288
FEATURE                 Location/Qualifiers
source                  1..288
                        mol_type = protein
                        organism = Pseudomonas monteilii
SEQUENCE: 4
MAISINIVAG PDEGVSSVSA TGQEKHIITN GERTAFDIQD SSLKRAVAAY FGKAPNDAYL    60
CSPTPWNDLY KSYDWDQVQT LLNVQSAKII GDATVPTILN TNTFRNNSSV EAEFNCDVTQ    120
NVSVTSESNW SDTSSSVEIGQ EISYSIGFLG TGVEGSTSLN YTQSWQHGGS HSETLELGSS   180
AGVKVTLKPG QAVKAELSAS KGRLVIQIVY QVTLFGDTAI NYNPTYKGHH FYGLNILGVM    240
NSGNLPTTIT TTETISIDYY SNVEVNVYDI ENGSVLETYK LDVKRVAS                288

SEQ ID NO: 5            moltype = AA   length = 287
FEATURE                 Location/Qualifiers
source                  1..287
                        mol_type = protein
                        organism = Echinicola vietnamensis
SEQUENCE: 5
MGISISIIAG HDQSVSSVNA SGTVQHVITD EERTTFRLGD KQLKDAVKAY FGKSPNDAYL    60
HSPTPWGDLY KKYSWPQVQM VLVVQSAEIL GITSEPVIVK TQEFTNDSSK KGTFNVAISD    120
SVNNTTSSNW STGGTLSIGQ KFSYDVKFLG AGGGGETSLS YSQSWGVGGQ ESKSITVGST    180
AGVSVELDPG QSILAELSAS RGVMKVRLRY NAYLIGNTAI NYNPTYKGHH FWSLGIGGVM    240
SSGGIKNSVQ STEDIEIGYY SNSKIELKDK TNGKLVRERV LADEVGV                 287

SEQ ID NO: 6            moltype = AA   length = 286
FEATURE                 Location/Qualifiers
REGION                  1..286
                        note = Sphingomonas species
source                  1..286
                        mol_type = protein
                        organism = unidentified
SEQUENCE: 6
MPLTISVNAG PDAQSSTVAV SGTDLHIITD GERAAFSIED ASLKGAVATY FGEAPDDAFL    60
CSPTPWGDLY ETYGWQQVQT TLAVQSATIL GVSGNPAILS SQIFKNDSSV PAEFNTGITQ    120
EVAVGTESNW TNSSALEIGQ TISYEIGFLG SGAGGETSMS FTETWEQGGS ESETVTLGTS    180
SGVVVTLQPG QAVEAELEAS KGVLQIQIVY QLTLAGMTAI NYGDTYKGHH FWGLDINAVM    240
QAAGLPTSIV TTETLAIDFY ANSQIILKDT SGNVVNTLVM GAAAGK                  286

SEQ ID NO: 7            moltype = AA   length = 291
FEATURE                 Location/Qualifiers
REGION                  1..291
                        note = Granulicella species
source                  1..291
                        mol_type = protein
                        organism = unidentified
SEQUENCE: 7
MAGITVQIIA GTSASTSSVS ASGSVQHIIT DKEVQTFGIP DGKLKDAVAK YFGKSPNDAY    60
LHSDTPWGDL YKTYGWPQVQ TVLNVASATV TGITSEPVIV AQQTFKNNSS VRGTFNVGIS    120
DTVTDTTESN WSTSNTIDVT QTVNYGISPL GSGGGGSTSM SYSRTWGQGG SQSKSVAVGS    180
SQGVTVELDP GESVQALLTA SRGVMKVRIV YQANLIGSTA INYNPRYKDH HFWALDLPSV    240
MQASNINNSL KFTEDIEIGF FTNAEVELKN ASGKAVMALK ATAAIQELQP A            291

SEQ ID NO: 8            moltype = AA   length = 289
FEATURE                 Location/Qualifiers
REGION                  1..289
                        note = Chromatiaceae species
source                  1..289
                        mol_type = protein
                        organism = unidentified
SEQUENCE: 8
```

```
MGINISIVAG QDKSSSSVNA SGTVQHVITD EERTTFHLGD KQLKDAVKAY FGKSPNDAYL    60
HSPTPWDDLY KRYNWPQVEM VLVVQSAEIL GITSEPVIVK TQEFSNNSNK TGTFNVNITE   120
SVDNTTSSNW STGGTLTIGQ KISYKVGFLG TGVEGETSMS YSQSWGVGGQ ESKSITVGSS   180
SGVTVELNPG ESVIAELSAS RGVMKVRIHY NAYLIGSTAV NYNPTYKDHH FWSLDIAAVM   240
SKGGIINSVK STEDIEIGYY SNSKIELKDK KTGTFKAAYS MADQPGKAA               289

SEQ ID NO: 9               moltype = AA  length = 292
FEATURE                    Location/Qualifiers
source                     1..292
                           mol_type = protein
                           organism = Aquimarina latercula
SEQUENCE: 9
MGISISIVAG QDQAASSVNA SGSVQHVITD EERTTFKLGD KQLKDAVNKY FGKSPNDAYL    60
HSPTPWGDLY KKYNWPQVQM VLVVQSAEIL GITSEPVIVK TQDFTNNSSI KGTFNVAISE   120
SLNNTTSSNW STGGTLTIGQ KFSYGVKFLG AGAEGETSLS YSQSWGVGGQ ESKSITVGST   180
SGVSVELDPG ESVVAELSAS RGVMKVRIRY NAYLIGNTAV NYNPTYKKHH FWSLGIGGVM   240
SKGGVSNSVQ STEDIEIGYY SNSKIELKNK ISGKIKASHA LADATAGELT LA          292

SEQ ID NO: 10              moltype = AA  length = 300
FEATURE                    Location/Qualifiers
source                     1..300
                           mol_type = protein
                           organism = Nitrococcus mobilis
SEQUENCE: 10
MGISISIVAG HDKSASSVNA TGTVQHVITD QERTTFHLGD KQLKDAVKAY FGKSPNDVYL    60
HSPTPWGDLY KKYSWPQVQM ILVVQSAEIL GITSEPVIVK TQEFVNNSRQ KGTFNVAISE   120
SVNNTTSSNW STGGTLTIGQ KFSYGVKFLG AGAEGETSLS YSQSWGVGGQ ESKSITVGSS   180
SGVSVELDPG ESVLAELSAS RGVMKVRIRY NAYLIGNTAV NYNPTYKDHH FWSLGVAGVM   240
AKGGITNSVQ STEDIEIGYY SNSKIELKDK ATGALKAAYN MADAPGQSAA ESRQPALDEA   300

SEQ ID NO: 11              moltype = AA  length = 295
FEATURE                    Location/Qualifiers
source                     1..295
                           mol_type = protein
                           organism = Methanosarcina barkeri
SEQUENCE: 11
MGIEISIKAG ADAATSNVSA SGSVQHIITD KERKTFDIED AGLKSAVEKY FGKKPNDAYL    60
HSPTPWDDLY KTYGWSEVQT ILDVKSAKIT EITSEPVIVK TKKFVNSSSK KATFDASISD   120
QVTNTTESNW SQTDTIDVGQ KITYDVSFLG AGGGGETSMS YSHSWGQGGS ESKSITVGSS   180
SGVSVELEPG ESIEAVLSAS RGVMKVRIVY MAHLTGSTAV NYNPTYKDHH FWSLPITGVM   240
SAASLSTNRE FTEDIEIGYY SDAKIELRNP QGQLKATFLV ANKPAVEKVP IKTAV        295

SEQ ID NO: 12              moltype = AA  length = 295
FEATURE                    Location/Qualifiers
REGION                     1..295
                           note = JGI 2170009770 BMHB3_01721240 hypothetical protein
source                     1..295
                           mol_type = protein
                           organism = unidentified
SEQUENCE: 12
MGIEISIKAG ADAATSSVSA SGSVQHIITD KERKTFGIED SGLKSAVEKY FGKKPNDAYL    60
HSPTPWDDLY KTYGWSEVQT ILDVKSAKIT GITSEPVIVA TKKFVNSSSK KATFDASISD   120
QVTNTTESNW SQTDTIDVGQ KITYDVSFLG AGGGGETSMS YSHSWGQGGS ESKSVTVGSS   180
SGVSVELEPG ESIEAVLSAS RGVMRVRIVY MDHLTGSTAV NYNPTYKDHH FWSLPITGVM   240
SAASLSTNRE FTEDIEIGYY SDAKIELRNP QGQLKATFLV ANKPAVEKVP IKTVV        295

SEQ ID NO: 13              moltype = AA  length = 294
FEATURE                    Location/Qualifiers
source                     1..294
                           mol_type = protein
                           organism = Methanosarcina mazei
SEQUENCE: 13
MGIQISIKAG ADASTSSVSA SGSVQHIITD NERKTFGIED AGLKSAVEKY FGKKPNDAYL    60
HSPTPWDDLY KTYGWAEVQT ILDVKSSTIT GITSEPVIVA TKKFVNSSTK VATFDASISD   120
QVNDTTESNW SETDTIDVGQ KITYEVSFLG AGGGGETSMS YSHSWGQGGS ESKSITVGSS   180
SGVTVQLNPG ESVEAVLTAS RGVMKVRIVY LAHLTGSTAV NYNPTYKDHH PWALPITGVM   240
GAASLSTTRE FTEDIEIGYY SDAKIELRDP TGQLKATFLA ANKPAIEKIA VKAV         294

SEQ ID NO: 14              moltype = AA  length = 292
FEATURE                    Location/Qualifiers
source                     1..292
                           mol_type = protein
                           organism = Yokenella regensburgei
SEQUENCE: 14
MGINVQVNTD ADPKKTTVSA SGSIQHVITG NEVNSFGLSD SALKDAVAKY FGKRPNDAYL    60
KSPTPWGDLY KTYGWEQVQT VLVARSAQVL SVNSSPSIIK TVILKNNSNK PATFNASVSD   120
NITNSVETNW NVTTSVDFSE TVSYEVSFEG LGSVGGSTTW SFGMSFGVGG SKSESISIGS   180
DQGVTVDLDP GESVEVQLTA SIGSLRARVF YDVYLTGYSA VNYNPTFKDH HFWALNIGDV   240
MSAGGISNNR QITEDITVGY YSNAQVILSN AKKTVLRALA VPLENSVPVD AG          292
```

-continued

```
SEQ ID NO: 15              moltype = AA  length = 287
FEATURE                    Location/Qualifiers
REGION                     1..287
                           note = Dickeya species
source                     1..287
                           mol_type = protein
                           organism = unidentified
SEQUENCE: 15
MSIKVDITAS SDNHQTIATA TGNDISVISN EERGTFQLND QQLKRAVEVY FGKKPNDAYL   60
SSPTPWGDLY KTYNWQQVMR TLQPVSTRVI SQNSTPVIVM EQDFVNNSSV PAVYNVKISQ  120
SVQNTVKSSW NTGGKLTVGQ KVKYGISFLG TGGGGESSIS YEQSWGIGGE QSTTITLGTE  180
SGLQVTLQPG QAVTAELVAS RGSMKVQVDY QASLSGISAV NYNPTYKDHH FWGLPITQIM  240
RSSNISNAIV SSEIIDIGFY ADSKVILRDK NTGGVFRTFN LFDKHTD            287

SEQ ID NO: 16              moltype = AA  length = 287
FEATURE                    Location/Qualifiers
REGION                     1..287
                           note = Dickeya species
source                     1..287
                           mol_type = protein
                           organism = unidentified
SEQUENCE: 16
MSIKVDITAS SDNHQTIATA TGNDIAVISN EERGTFQLND QQLKRAVEVY FGRKPNDAYL   60
SSPTPWGDLY KTYNWQQVMR TLQPVSTRVI SQNSTPVIVM EQDFVNNSSV PAVYNVKISQ  120
SVQNTVKSSW NTGGKLTVGQ KVKYGISFLG TGGGGESSIS YEQSWGIGGE QSTTITLGTE  180
SGLQVTLQPG QAVTAELVAS RGSMKVQVDY QASLSGISAV NYNPTYKDHH FWGLPITQIM  240
RSSNISNSIV SSEIIDIGFY ADSKVILRDK NTGGVFRTFN LFDKHTD            287

SEQ ID NO: 17              moltype = AA  length = 294
FEATURE                    Location/Qualifiers
source                     1..294
                           mol_type = protein
                           organism = Methanosarcina mazei
SEQUENCE: 17
MGIQISIKAG ADASTSSVRA SGSVQHIITD NERKTFGIED SGLKSAVEKY FGKKPNDAYL   60
HSPTPWDDLY KTYGWAEVQT ILDLKSSTIT GITSEPVIVA TKKFVNSSTK VATFDASISD  120
QVNDTTESNW SETDTIDVGQ KITYEVSFLG AGGGGETSMS YSHSWGQGGS ESKSITVGSS  180
SGVTVQLNPG ESVEAVLTAS RGVMKVRIVY LAHLTGSTAV NYNPTYKDHH FWALPITGVM  240
GAASLSTTRE FTEDIEIGYY SDAKIELRDP TGQLKATFLA ANKPAIEKIA VKAV       294

SEQ ID NO: 18              moltype = AA  length = 294
FEATURE                    Location/Qualifiers
source                     1..294
                           mol_type = protein
                           organism = Methanosarcina mazei
SEQUENCE: 18
MEIQISIKAG ADASTSSVSA SGSVQHIITD NERKTFGIED AGLKSAVEKY FGKKPNDAYL   60
HSPTPWDDLY KTYGWAEVQT ILDVKSSTVT GITSEPVIVA TKKFVNSSTK VATFDASISD  120
QVNDTTESNW SQTDTIDVGQ KITYEVSFLG AGGGGETSMS YSHSWGQGGS ESKSITVGSS  180
SGVTVQLNPG ESVEAVLTAS RGVMKVRIVY LAHLTGSTAV NYNPTYKDHH FWALPITGVM  240
GAASLSTTRE FTEDIEIGYY SDAKIELRDP TGQLKATFLA ANKPAIEKIA VKAV       294

SEQ ID NO: 19              moltype = AA  length = 304
FEATURE                    Location/Qualifiers
source                     1..304
                           mol_type = protein
                           organism = Methanosarcina barkeri
SEQUENCE: 19
MFNWFHTEKY GIEISIKAGA DAATSSVSAS GSVHHIITDK ERKTFGIEDS GLKSAVEKYF   60
GKKPNDAYLH SPTPWDNLYK TYGWSEVRTI LDVKSAKITG ITSEPVIVAT KKFVNSSSKK  120
VTFDAGISDQ VTNTTESNWS QTDTIDVGQK ITYDVSFLGA GGGGETSMSY SHSWGQGGSE  180
SKSITVGSSS GVSVELEPGE SIEAVLSASR GVMKVRIVYM AHLTGSTAVN YNPTYKDHHF  240
WSLPITGVMS AASLSTNREF TEDIEIGYYS DAKVELRNPQ GQVKATFLAA NKPAVEKVPI  300
KTAV                                                            304

SEQ ID NO: 20              moltype = AA  length = 292
FEATURE                    Location/Qualifiers
REGION                     1..292
                           note = Methanosarcina species
source                     1..292
                           mol_type = protein
                           organism = unidentified
SEQUENCE: 20
MGIEISVNAG SDTATSSVNA SGSVQHIITD KERTTFSIQD GGLKDAVNKY FGKRPNDAYL   60
HSPTPWDDLY KTYGWPEVET VLVVQSATIR GITSEPVIVA TKTFSNSSSK KATFDASISD  120
QVTNTVESNW SQTDTIEVGQ KFTYNVSFLG AGGGGETSMS YSHSWGQGGS ESKSITVGSS  180
SGVKVELEPG ESVEAQLTAS RGVMKVRIVY KAYLIGSTAI NYNPTYKDHH FWALGIGGVM  240
GAASLPTTRE YTEDIEIGYY SNSKIELRDP AGQLKGMFFE ADKAAVADNV AL         292
```

```
SEQ ID NO: 21              moltype = AA   length = 182
FEATURE                    Location/Qualifiers
source                     1..182
                           mol_type = protein
                           organism = Methanosarcina barkeri
SEQUENCE: 21
MGIEISIKAG ADAATSSVSA SGSVQHIITD KERKTFDIED SGLKSAVGKY FGKKPNDAYL   60
HSPTPWDDLY KTYGWSEVQT ILDVKSAKIT GITSEPVIVA TKKFVNSSSK KATFDASISD  120
QVTNTTESNW SQTDTIDVGQ KITYDVSFLG AGGGGETSMS YSHSWGQGGS ESKSITVGSA  180
QE                                                                182

SEQ ID NO: 22              moltype = AA   length = 289
FEATURE                    Location/Qualifiers
source                     1..289
                           mol_type = protein
                           organism = Methanosarcina mazei
SEQUENCE: 22
MGIQISIKAG ADASTSSVRA SGSVQHIITD NERKTFGIED SGLKSAVEKY FGKKPNDAYL   60
HSPTPWDDLY KTYGWAEVQT ILDLKSSTIT GITSEPVIVA TKKFVNSSTK VATFDASISD  120
QVNDTTESNW SETDTIDVGQ KITYEVSFLG AGGGGGETSM SYSHSWGQGG SESKSITVGS  180
SSGVTVQLNP GESVEAVLTA SRGVMKVRIV YLAHLTGSTA VNYNPTYKDH HFWALPITGV  240
MGAASLSTTR EFTEDIEIGY YSDAKIELRD PTGQLKATFL AAISQQLKK             289

SEQ ID NO: 23              moltype = AA   length = 248
FEATURE                    Location/Qualifiers
REGION                     1..248
                           note = internal pool YJP-3_D0530001_NODE_186_185
source                     1..248
                           mol_type = protein
                           organism = unidentified
SEQUENCE: 23
MSISIKVYAS IYEGQSRISY GGRDVSLISQ QERNTFKLND NQLKNAAKRV FGRRPNDAFL   60
RSPTPWNLYE NNRWMQTQRS LFIQGVRLIE RSSSPVIVAN QEFVNSSSVP AKFNAAIEQN  120
VSNTVSSQWS TGGTLSIGQT IKVEVGFLGT GVGSETSLSY EQSWGISGER SQSITVGTSS  180
GVEVELQPGQ PGQPAPRPTS RRGTVPTSAM PAAPAATPSE RPGDSAHTAP APGQSPAAET  240
ASAPVLWQ                                                           248

SEQ ID NO: 24              moltype = AA   length = 294
FEATURE                    Location/Qualifiers
source                     1..294
                           mol_type = protein
                           organism = Methanosarcina mazei
SEQUENCE: 24
MGIQISIKAG ADASTSSVSA SGSVQHIITD NERKTFGIED AGLKSAVEKY FGKKPNDAYL   60
HSPTPWDDLY KTYGWAEVQT ILDVRSSTIT GITSEPVIVA TKKFVNSSTK VATFDASISD  120
QVNDTTESNW SETDTIDVGQ KITYEVSFLG AGGGGETSMS YSHSWGQGGS ESKSITVGSS  180
SGVTVQLNPG ESVEAVLTAS RGVMKVRIVY LAHLTGSTAV NYNPTYKDHH FWALPITGVM  240
GAASLSTTRE FTEDIEIGYY SDAKIELRDP TGQLKATFLA ANKPAIEKIA VKAV        294

SEQ ID NO: 25              moltype = AA   length = 294
FEATURE                    Location/Qualifiers
source                     1..294
                           mol_type = protein
                           organism = Methanosarcina mazei
SEQUENCE: 25
MGIQISIKAG ADASTSSVSA SGSVQHIITD NERKTFGIED AGLKSAVEKY FGKKPNDAYL   60
HSPTPWDDLY KTYGWAEVQT ILDVRSSTIT GITSEPVIVA TKKFVNSSTK VATFDASISD  120
QVNDTTESNW SQTDTIDVGQ KITYEVSFLG AGGGGETSMS YSHSWGQGGS ESKSITVGSS  180
SGVTVQLNPG ESVEAVLTAS RGVMKVRIVY LAHLTGSTAV NYNPTYKDHH FWALPITGVM  240
GAASLSTTRE FTEDIEIGYY SDAKIELRDP TGQLKATFLA ANKPAIEKIA VKAV        294

SEQ ID NO: 26              moltype = AA   length = 294
FEATURE                    Location/Qualifiers
source                     1..294
                           mol_type = protein
                           organism = Methanosarcina mazei
SEQUENCE: 26
MGIQISIKAG ADASTSSVSA SGSVQHIITD NERKTFGIED SGLKSAVEKY FGKKPNDAYL   60
HSPTPWDDLY KTYGWAEVQT ILDVRSSTIT GITSEPVIVA TKKFVNSSTK VATFDASISD  120
QVNDTTESNW SETDTIDVGQ KITYEVSFLG AGGGGETSMS YSHSWGQGGS ESKSITVGSS  180
SGVTVQLNPG ESVEAVLTAS RGVMKVRIVY LAHLTGSTAV NYNPTYKDHH FWALPITGVM  240
GAASLSTTRE FTEDIEIGYY SDAKIELRDP TGQLKATFLA ANKPAIEKIA VKAV        294

SEQ ID NO: 27              moltype = AA   length = 294
FEATURE                    Location/Qualifiers
REGION                     1..294
                           note = Methanosarcina species
source                     1..294
```

-continued

```
                          mol_type = protein
                          organism = unidentified
SEQUENCE: 27
MGIQISIKAG ADASTSSVSA SGSVQHIITD NERKTFGIED AGLKSAVEKY FGKKPNDAYL    60
HSPTPWDDLY KTYGWAEVQT ILDVKSSTVT GITSEPVIVA TKKFVNSSTK VATFDASISD   120
QVNDTTESNW SQTDTIDVGQ KITYEVSFLG AGGGGETSMS YSHSWGQGGS ESKSITVGSS   180
SGVTVQLNPG ESVEAVLTAS RGVMKVRIVY LAHLTGSTAV NYNPTYKDHH FWALPITGVM   240
GAASLSTTRE FTEDIEIGYY SDAKIELRDP TGQLKATFLA ANKPAIEKIA VKAV         294

SEQ ID NO: 28             moltype = AA  length = 301
FEATURE                   Location/Qualifiers
REGION                    1..301
                          note = Proteobacteria species
source                    1..301
                          mol_type = protein
                          organism = unidentified
SEQUENCE: 28
MSISVRIRAG SNMQNSSVYA EGSEFHIITD SERYSFNIGS DADLKNAVGK YFGKNPNDAY    60
LHSPTPWGDL YKTYGWPQTQ TNLTVASSTI AEITSEPSIV KTQTFKNNSS VAGTFDVSIS   120
EEVSNTVESN WNNSSSVSFG QSISYNVSFL GTGGGGETSF GFEQTWGKGG SNSKSVTVGS   180
SSGVTVLLQP GESVKSILTA TRGYMNVRLV YRANLSGTCA VNYNPTFQGH HFWGLGINNV   240
VNAAGSSNNV QIVEDIKIGY YSDSELILED LNGNRRIYHF AIPGMPPAGK SAPTSSREAT   300
L                                                                  301

SEQ ID NO: 29             moltype = AA  length = 294
FEATURE                   Location/Qualifiers
source                    1..294
                          mol_type = protein
                          organism = Anaerobacillus macyae
SEQUENCE: 29
MSQDGIEISI KPGLDKESSS VTAVGSVRHI ITKKEMKNFG VERDQLKKSV GNFFGQAPKD    60
VPLYSPTPWG DLFRKFGGDE TSTVLKVKDA KVIDITSKPV VISSQTFKND SSSHATFDCA   120
IKDSVSETVE SSWSSSNKIE ASQAINYTVG FPGGDAGGET KIAYSHSWGE ETSHSKQIEV   180
GRSSGVHVNL EPGQAVEAII NASRGSMKVE IVYEAKLSGS FWTNYPNKWK KHHFWRFNID   240
QVFNTNKIPN SIIVTENILV GFYANSTIDL KDVETQRSLN SVIADNSETL SFTT         294

SEQ ID NO: 30             moltype = AA  length = 291
FEATURE                   Location/Qualifiers
source                    1..291
                          mol_type = protein
                          organism = Enterobacter cloacae
SEQUENCE: 30
MRINIQLREN IESSIVNGSG VLSGVLTNTE QQTFGLDERH IRWAVCSISG REPNDVFVRS    60
PTPWGDLYQR YNWRQVHRMT EIRSARFLEF ETVPEIVAET ELVNNSSVSG VFTANMNTTV   120
TNTMSSGWHV DHGITVGQSI RYGVTKVGGE TSFEYTHGWG ENGEVSESVS LSTGSGVTVQ   180
LEPGQAVVAL MIASRGQARV QVEYVSYLNG LVATNYNPRH NGHHFLGYGV ESVLRALSNS   240
NSRISTETIT IGMYSRARVE LRDKETKRLL RTVWLDEEII PGGVVVPQPE L            291

SEQ ID NO: 31             moltype = AA  length = 291
FEATURE                   Location/Qualifiers
source                    1..291
                          mol_type = protein
                          organism = Pectobacterium betavasculorum
SEQUENCE: 31
MTMRINVIIQ ENIENSVVNG SGITSGIITD VERRTFNLED TQLKRACGLL VGKEPTDAFL    60
RSPTPWNDLF VTYNWAQTQR NTSVRTARFV GHNAVPELVS EKELVNNSSI GATFNANLST   120
TVSNTVSSSW SSSHSISVGQ EIEYKILGIG GSTSFDYTHE WGVGGEQSQT IELSTGAGVE   180
VYLEPGQAVS AQMVASRGNA QVAIEYLSYL TGGAAMNYYP RYDGHHFRWR AISRIMDVGG   240
ISNQVITREN LNISVYSSAR LELIDIKTKK LLRTYYLGDI LSVGEANAQD D            291

SEQ ID NO: 32             moltype = AA  length = 294
FEATURE                   Location/Qualifiers
source                    1..294
                          mol_type = protein
                          organism = Sodalis praecaptivus
SEQUENCE: 32
MKINIQPRES IEDSVVNGSG VLSEVITSDE QRLFKLEEPD IIRAITALNG REPNDVFVRS    60
PTPWGDLYSS YRWRQVHKNT EIFSAKFLQF SSAPEIVSET ELVNNSKVAG EFNVNLLTEV   120
LNTVSSGWKV EDGISVGQKV TYGVDWLKGE TSFEYTHGWG VNGEVSESVT LTTGAGVTVL   180
LAPGQAVVAQ MIASRGRARV EVEYLSHLDG LVAMNYEPPY KEHHFWGRDV ASILRQNSTP   240
NACRSTEVIE IAMYSKARVE LRDKANKDLL KTVWLNEEAK PIGNSVASAE LCRE         294

SEQ ID NO: 33             moltype = AA  length = 285
FEATURE                   Location/Qualifiers
REGION                    1..285
                          note = Proteobacteria species
source                    1..285
                          mol_type = protein
                          organism = unidentified
```

```
SEQUENCE: 33
MSILLSVIAG MSADHSSASG SGQEIHIITD KERESFGIGN DQVLKKAVEA YFGKSPDDVY    60
LKSDTPWDDL YKTYNWSQVQ TNYRVRDVQI LEITSQPEIL AKKTFENKSS KSVTYNASIS   120
DTRANTLETH WSQSTNKSVG FSIKASFSVP GVFGFEGGST FNFDSTWGEG GFQSTTTTVG   180
TTTGIIVTLD PGEKVEAHLN ATRGHLKVRV NYDTYLTGIT AVNYAQTYKE HHFWGLPIDK   240
VLKSSGINNN QIVTQDLNFS YYSDAHVVVY DQKGREKRTI NASFN                   285

SEQ ID NO: 34            moltype = DNA   length = 870
FEATURE                  Location/Qualifiers
source                   1..870
                         mol_type = other DNA
                         organism = Pseudomonas vranovensis
SEQUENCE: 34
atggctatta gtatcgcgat caatgctggg caatcttcat ccgcgtcaac cgtcattgcc    60
acgggcacgg tccagaacgt tatcaccgac accgagcgaa ccttgttcaa catccaggat   120
gggtcgttga aagcggcggt gtctgcctat tttggccgct cgcccaatga cgcttacgtt   180
tgcagcccca cgccctgggg tgatctgtac cagacctaca actggccgca ggtacaagcc   240
acgctgtcgg tggtgagcgc aaggattgtc tcggaaacct cgaacccgat tgccctcaat   300
accaatacct tcaccaacca ctcctcggtg ccggcggagt tcaactgcgg ggtcacccag   360
gaggtgacgg tcaccgcgga aagcaactgg tcgagctcgt cggaagtcgg catcagccag   420
acgatttcct acgggatctc gttcctcggc gccggcgccc agggcgaaac cgccttgagt   480
ttcacccaga cctgggagca gggcggttcg caaagtgagt cggtaaccct gggttcgagc   540
gccggagtga ccctgacctt gcaacccggg cagaccgtag aggcgatact gtcggccagc   600
aagggggtac tgacggtaga agttgagtat caaataaccc tggcggggt aacggcggtc     660
aattacaacc cgacgtatca ggggcatcac ttctgggcac tggatatcaa caacgtcatg   720
agtgccggca aactgtcgaa tgtcatcacc agcaaagaaa ccatcgtgat cgactacttc   780
accaatacca cgatcaccgt gcaggaccct gaaagccagg atgtcatccg caccctcgtc   840
acctcggcca ggccgggcat cagttcataa                                    870

SEQ ID NO: 35            moltype = DNA   length = 870
FEATURE                  Location/Qualifiers
source                   1..870
                         mol_type = other DNA
                         organism = Pseudomonas vranovensis
SEQUENCE: 35
atggctatta gtatcgcgat caatgctggg caatcttcat ccgcgtcaac cgtcattgcc    60
acgggcacgg tccagaacgt tatcaccgac accgagcgaa ccttgttcaa catccaggat   120
gggtcgttga aagcggcggt gtctgcctat tttggccgct cgcccaatga cgcttacgtt   180
tgcagcccca cgccctgggg tgatctgtac cagacctaca attggccgca ggtacaagcc   240
acgctgtcgg tggtgagcgc aaggattgtc tcggaaacct cgaatccgat tgccctcaat   300
accaatacct tcaccaacca ctcctcggtg ccggcggagt tcaactgcgg ggtcacccag   360
gaggtgacgg tcaccgcgga aagcaactgg tcgagctcgt cggaagtcgg catcagccag   420
acgatttcct acgggatctc gttcctcggc gccggcgccc agggcgaaac cgccttgagt   480
ttcacccaga cctgggagca gggcggttcg caaagtgagt cggtaaccct gggttcgagc   540
gccggagtgg ccctgacctt gcaacccggg cagaccgtag aggcgatact gtcggccagc   600
aagggggtac tgacggtaga agttgagtat caaataaccc tggcggggt aacggcggtc     660
aattacaacc cgacgtatca ggggcatcac ttctgggcac tggatatcaa caacgtcatg   720
agtgccggca aactgtcgaa tgtcatcacc agcaaagaaa ccatcgtgat cgactacttc   780
accaatacca cgatcaccgt gcaggaccct gaaagccagg atgtcatccg caccctcgtc   840
acctcggtca ggccgggcat cagttcataa                                    870

SEQ ID NO: 36            moltype = DNA   length = 870
FEATURE                  Location/Qualifiers
misc_feature             1..870
                         note = XM21_pooled_NODE_1357_58
source                   1..870
                         mol_type = other DNA
                         organism = unidentified
SEQUENCE: 36
atggctatta gtatcgcgat caatgctggg caatcttcat ccgcgtcaac cgtcattgcc    60
acgggcacgg tccagaacgt tatcaccgac accgagcgaa ccttgttcaa catccaggat   120
gggtcgttga aagcggcggt gtctgcctat tttggccgct cgcccaatga cgcttacgtt   180
tgcagcccca cgccctgggg tgatctgtac cagacctaca actggccgca ggtacaagcc   240
acgctgtcgg tggtgagcgc aaggattgtc tcggaaacct cgaacccgat tgccctcaat   300
accaatacct tcaccaacca ctcctcggtg ccggcggagt tcaactgcgg ggtcacccag   360
gaggtgacgg tcaccgcgga aagcaactgg tcgagctcgt cggaagtcgg catcagccag   420
acgatttcct acgggatctc gttcctcggc gccggcgccc agggcgaaac cgccttgagt   480
ttcacccaga cctgggagca gggcggttcg caaagtgagt cggtaaccct gggttcgagc   540
gccggagtgg ccctgacctt gcaacccggg cagaccgtag aggcgatact gtcggccagc   600
aagggggtac tgacggtaga agttgagtat caaataaccc tggcggggt aacggcggtc     660
aattacaacc cgacgtatca ggggcatcac ttctgggcac tggatatcaa caacgtcatg   720
agtgccggca aactgtcgaa tgtcatcacc agcaaagaaa ccatcgtgat cgactacttc   780
accaatacca cgatcaccgt gcaggaccct gaaagccagg atgtcatccg caccctcgtc   840
acctcggcca ggccgggcat cagttcataa                                    870

SEQ ID NO: 37            moltype = DNA   length = 867
FEATURE                  Location/Qualifiers
source                   1..867
                         mol_type = other DNA
```

-continued

```
                              organism = Pseudomonas monteilii
SEQUENCE: 37
atggctattt caattaatat tgttgcggga cctgacgaag gcgtatcttc agtttctgct    60
acaggccaag aaaagcacat catcaccaac ggcgagcgga ccgcgttcga cattcaagac   120
tcatcgttaa aacgtgcagt cgccgcttat tttggcaaag cgccaaacga tgcatacctg   180
tgcagtccga caccttggaa tgacctgtac aaaagctacg actgggacca ggttcaaaca   240
ctccttaatg tacaaagcgc gaagataatt ggcgacgcaa ccgttcctac aatccttaac   300
acaaacacgt tcagaaacaa ctcctcagtt gaagctgagt ttaattgcga tgtaactcag   360
aacgtgtcgg ttacctctga aagcaattgg tctgatacat cctccgttga aatcggacag   420
gaaatcagct attcgattgg ttttttgggt acggggtag aaggctcaac atcgctaaat    480
tacacgcaaa gttggcagca tggtggctct cacagcgaaa cactcgagct tggttcgagc   540
gcaggggtga aggtcaccct caaaccagga caggcagtca aagcggagct atctgcaagt   600
aaaggtagac ttgttatcca gattgtttac caagtcactc tctttggaga tactgcaatc   660
aactacaacc ccacctacaa ggggcatcac ttttacggcc ttaacatctt gggcgtaatg   720
aatagcggaa acttaccaac aaccatcacc acaactgaaa caatctctat cgattactac   780
tccaacgtag aagttaacgt ttatgacatc gaaaacggca gtgtattgga aacgtacaaa   840
cttgatgtta agagagttgc ttcgtaa                                       867

SEQ ID NO: 38          moltype = DNA   length = 864
FEATURE                Location/Qualifiers
source                 1..864
                       mol_type = other DNA
                       organism = Echinicola vietnamensis
SEQUENCE: 38
atgggaatca gcattagtat tattgcagga catgaccagt ccgtttcaag tgtaaatgca    60
agtggaacgg tccagcacgt catcaccgac gaagagcgaa ccacttttag attgggcgat   120
aagcagctca aggatgcggt aaaggcctat tttggcaaat ctccaaacga tgcctatctg   180
cacagtccga caccatgggg cgatttgtac aagaaataca gttggcccca agtgcagatg   240
gtgctggtcg ttcagagcgc agagatcttg ggcatcacct cagaaccggt gatcgtcaag   300
acccaggaat tcaccaatga cagcagcaaa aaggggacgt ttaacgtcgc catttccgat   360
tcggtaaaca atacgaccag ctccaattgg agtacaggag gaacattgtc aattggccag   420
aagtttagct atgacgtgaa gtttctcggt gctggcggtg gaggggagac ctcccttttcc   480
tatagccaat cttggggagt aggagggcag gaatccaagt ccattaccgt gggatccacc   540
gcaggagtga gtgtggagct cgacccgggg cagtccatcc tagcggaact ttctgccagc   600
aggggtgtca tgaaggtgag gttgcggtac aatgcctact tgatcggcaa cacggccatc   660
aattataacc ccacctacaa aggtcatcac ttctggagcc tgggaatcgg cggggtgatg   720
tcatcgggag gaatcaaaaa ttccgtgcag tctaccgaag acattgaaat cggatattat   780
tccaattcca aaatcgaatt gaaggataag accaacggga aattggtacg tgaaagggtg   840
cttgccgacg aggtgggtgt ttga                                          864

SEQ ID NO: 39          moltype = DNA   length = 861
FEATURE                Location/Qualifiers
misc_feature           1..861
                       note = Sphingomonas species
source                 1..861
                       mol_type = other DNA
                       organism = unidentified
SEQUENCE: 39
atgcccctga caatcagcgt caacgccgga cccgacgccc agtcgtctac tgtcgccgta    60
tcgggaaccg atctgcacat catcaccgac ggcgagcgag ctgctttcag catcgaggac   120
gcgagccgga agggcgcggt ggcgacctat ttcggcgaag ctcccgacga cgccttttttg   180
tgcagtccga cgccgtgggg ggatctgtac gagacctacg ggtggcagca ggtccagacc   240
acattggcgg tgcagagcgc gaccattctc ggcgtttcgg gcaacccggc gatattgagc   300
tcgcagatat tcaagaacga cagcagcgtt ccgccgagt tcaacaccgg catcacccag    360
gaagtagccg tgggcacgga aagcaattgg accaattcga gcgcgctcga aatcggccag   420
acgatttcct atgagatcgg ctttctcggc tcggggggcgg gcggggaaac gtcgatgtcg   480
ttcaccgaga catgggagca gggcggatcg gagagcgaga ccgtgacgct gggcaccagc   540
tcgggtgtgt tagtgacgct acaacccggc caagccgttg aggccgagct tgaagcgagc   600
aagggcgtgc tgcagatcca gatcgtctat cagctcacgt tggccggtat gaccgcgatc   660
aactatggcg acacgtacaa gggccaccat ttctggggc tggacatcaa cgccggtcatg   720
caggccgcgg ggctgccgac ttccatcgtc acgaccgaaa cgctcgcgat cgatttctac   780
gcgaactcgc agatcatcct taaggacacg agcggaaatg tcgtgaatac cctcgtcatg   840
ggcgccgcg ccggaaaata g                                             861

SEQ ID NO: 40          moltype = DNA   length = 876
FEATURE                Location/Qualifiers
misc_feature           1..876
                       note = Granulicella species
source                 1..876
                       mol_type = other DNA
                       organism = unidentified
SEQUENCE: 40
atggctggaa ttactgtaca aatcatcgct ggtacttctg cgtctacttc ctcggttagc    60
gcaagcggaa gcgttcaaca catcatcacc gacaaagaag tgcaaacctt cggcattccg   120
gacggcaaac tgaaggacgc cgtcgcgaaa tacttcggca aatcccccaa tgatgcctat   180
ctccacagcg acacgccgtg gggtgaccta tacaagacct acggctggcc gcaggccag    240
accgttctca acgttgccag cgcaacggtt accggcatca cctccgagcc tgtgattgtt   300
gcccagcaga cccttcaaaaa caacagcagc gtgcggggca ccttcaatgt cggcatctcc   360
gatacggtga ccgataccac cgaaagcaac tggtctacca gcaacaccat cgatgtcact   420
```

```
cagacggtta actacggaat cagcttcctc ggttcgggcg gcggcggctc cacgtcgatg   480
tcctacagcc gcacctgggg tcagggcgga tcgcagagca aatcggtcgc ggtcggctcc   540
agccagggcg ttacggttga gcttgatccc ggcgaatcgg ttcaggccct gctgacggca   600
agccgtggcg tcatgaaggt caggatcgtc tatcaggcga acctcatcgg ttccaccgca   660
atcaactaca acccaaggta caaagaccac cacttcgtcg cgctcgacct tcccagcgtc   720
atgcaagcgt ccaacatcaa caactctctc aagttcaccg aagatatcga gatcggtttc   780
ttcacgaacg ccgaggtgga gttgaagaat gcctccggca aggccgtcat ggcgctcaag   840
gcaacggcag caatccagga gttgcagccg gcttag                             876

SEQ ID NO: 41          moltype = DNA   length = 870
FEATURE                Location/Qualifiers
misc_feature          1..870
                       note = Chromatiaceae species
source                1..870
                       mol_type = other DNA
                       organism = unidentified
SEQUENCE: 41
atgggcatta acatcagcat cgttgctgga caagataaat cttcatccag tgtaaatgct   60
agcggaactg tacagcatgt tattactgat gaggaacgaa caacttttca tttaggtgat   120
aaacagctta aggatgcggt aaaagcctat tttggtaaga gtccaaacga tgcttatctt   180
catagcccaa caccctggga cgacctatac aaaagatata attggccaca agtagaaatg   240
gtgctggttg tccagagcgc agaaatcctt ggtattacct cagagccgat tattgttaaa   300
acccaagaat tttcaaataa cagtaataag acgggaacct tcaacgttaa tatcactgag   360
tcagtagaca atacaacatc atctaactgg agcacggggg gtacactcac catcggccaa   420
aaaatttcct ataaagtagg atttctaggt actggtgttg agggtgaaac ttcaatgtca   480
tacagtcaat catggggcgt tggcgggcaa gagtcaaaat caatcacagt gggttcatcc   540
tctggcgtaa ccgtagaact taaccctggt gagtctgtta ttgctgagct ttcagcaagc   600
cgtggcgtaa tgaaagttcg tatccattac aatgcctatc tcatcggaag tacggcggta   660
aactataacc ctacctacaa ggatcatcat ttctggagct tagacattgc cgctgttatg   720
tccaaaggag gcatcatcaa ctcagtgaaa tcaaccgaag acatagagat tggttattat   780
tctaactcta agatcgaact gaaagataaa aaaacgggaa cctttaaagc cgcgtactct   840
atggccgatc aaccgggtaa agcagcataa                                    870

SEQ ID NO: 42          moltype = DNA   length = 879
FEATURE                Location/Qualifiers
source                1..879
                       mol_type = other DNA
                       organism = Aquimarina latercula
SEQUENCE: 42
atgggtatta gtattagtat tgttgctgga caagatcagg cagcatctag cgtaaatgca   60
agtggatccg ttcaacacgt gattaccgat gaggaaagaa caacttttaa attgggggat   120
aaacaattaa aagatgcagt aaataagtat ttcggaaaat ctcctaatga tgcttactta   180
catagcccaa cgccatgggg cgatttgtat aaaaaatata attggccaca ggtacagatg   240
gttctggtgg tacaaagtgc agagatatta ggaattacat cagaaccggt gattgtaaaa   300
acacaagatt ttacaaacaa cagtagtata aaaggaacat ttaatgttgc gatttcagaa   360
tcattaaaca atactacttc gtctaattgg agtacaggta gtacattaac cattggtcag   420
aagtttagtt atggagtaaa atttcttgga gctggagcag aaggagaaac ctcattatct   480
tatagccaat catggggagt tggtggtcaa gagtctaaat caattaccgt aggttctaca   540
tcgggagtaa gtgtagaatt ggatcctgga gaatctgtag tagcagaact ttctgctagt   600
agaggagtta tgaaagtaag gattagatat aatgcttatc tgataggtaa tacagcggta   660
aactataatc ctacatataa gaaacaccat ttctggagtt taggaatcgg tggtgtcatg   720
tctaaaggag gagtttctaa ctcagtgcaa tccacagaag atatagaaat tggatactat   780
tctaattcta aaattgaact aaaagaataa ataagcggta agataaaagc gagtcatgca   840
ttagcagatg ctactgctgg cgaacttaca ttagcttaa                         879

SEQ ID NO: 43          moltype = DNA   length = 903
FEATURE                Location/Qualifiers
source                1..903
                       mol_type = other DNA
                       organism = Nitrococcus mobilis
SEQUENCE: 43
atgggcatca gtatcagcat cgtcgccggt cacgacaaat ccgcatcaag cgtaaacgcc   60
accggaaccg tgcagcacgt cattacggat caggaacgga cgactttcca tcttggcgat   120
aagcaactca aggacgccgt caaggcgtat ttcgggaaca gcccgaacga cgtgtacttg   180
catagcccga cgccgtgggg tgatctctac aagaagtaca gttggccgca ggtccaaatg   240
atcctggtcg tccagagcgc ggagattctc ggcatcacct cggagccggt gatcgtcaag   300
actcaggagt tcgtgaataa tagccgccag aaaggcacct taacgttgc catcacggag   360
tcggtgaaca acaccacgtc ctccaactgg agtaccggcg gcacgcttac gatcgggcag   420
aagttctcct acggtgtcaa gtttctcggt gccggggccg aggggagac ttcgctgtcg   480
tacagccagt cgtggggagt cgggggggcag gagtcgaaat cgatcactgt aggttcatcg   540
tccgggggtga gtgtagagct tgatcccggc gagtccgttc tcgccgagct ctctgccagt   600
cggggcgtga tgaaagtacg aattcgctat aacgcctacc tcatcggcaa tacagccgtg   660
aattacaacc ccacctataa ggaccatcat ttctggagct tgggtgtcgc gggtgtcatg   720
gcgaaaggcg gcattaccaa ttcggtgcaa tcgaccgaag acatcgagat cggttattac   780
tccaattcca agatcgagct caaagataag gcgacgggtg ccttgaaggc cgcctacaat   840
atggccgacg cgcccgggca atcggccgcg gagtctcgcc agcctgctct cgatgaggcc   900
tag                                                                 903

SEQ ID NO: 44          moltype = DNA   length = 888
```

-continued

```
FEATURE             Location/Qualifiers
source              1..888
                    mol_type = other DNA
                    organism = Methanosarcina barkeri
SEQUENCE: 44
atgggaattg aaatcagcat aaaggcgggt gcagacgcag caacttcaaa cgtcagcgct    60
tcgggaagtg tacagcacat tatcacagat aaagagagaa agacatttga cattgaagat   120
gcaggtctta aaagtgcagt tgaaaagtat ttcggaaaga aacctaatga tgcttatctt   180
cacagcccta ctccctggga tgacctctac aaaacatacg gctggagtga ggttcagacg   240
atactggatg tcaagagcgc aaaaataact gagatcactt cagaaccagt aatagtggca   300
accaagaaat tcgtcaatag cagctcaaag aaagccactt tcgatgccag catttcggac   360
caggtaacca ataccacgga gagcaactgg tctcagacgg acacaatcga tgtagggcag   420
aagattacat atgatgtcag cttcctgggg gccggtggag gaggagaaac ctcaatgtct   480
tacagccatt cctgggggca aggcggatct gaaagcaaaa gcattacagt cggctcaagc   540
tcaggagtaa gtgtagaatt ggaacctggc gagtcaattg aagctgtact gtcagcaagc   600
cgaggtgtaa tgaaggtgag gattgtttac atggcccatc taacaggcag tacagctgtc   660
aattataacc cgacttacaa agaccaccat ttctggtctc ttcctattac tggcgttatg   720
agtgctgcca gtctctcgac taacagagaa tttacagaag acatcgagat aggctactac   780
tcagacgcaa aaatagaact aagaaatccg caggtcaat taaaggcaac atttttggtg    840
gctaataaac ccgcagttga aaaagtacca attaaaacag cagtttaa               888

SEQ ID NO: 45      moltype = DNA   length = 885
FEATURE             Location/Qualifiers
source              1..885
                    mol_type = other DNA
                    organism = Methanosarcina mazei
SEQUENCE: 45
atgggaatcc aaataagcat aaaagcgggt gctgacgcat caacttccag cgtcagcgct    60
tcgggaagtg tacagcacat catcacagac aatgagagaa agacattcgg cattgaagat   120
gcaggtctca agagtgcagt tgaaaagtat tttggaaaga agccgaatga tgcctatctt   180
cacagcccta ctccatggga cgaccttttac aaaacatatg gatgggctga ggttcagaca   240
atactggacg tcaagagttc aacaataacc gggattactt cagaaccggt tatagtggca   300
accaagaaat tcgtcaacag cagcacaaag gtagccactt tcgatgccag catttcgagac   360
caggtcaatg ataccacgga aagcaactgg tctgaaacgg acacaatcga cgtagggcag   420
aagattactt atgaggtcag ctttctggga gccggaggag ggggagaaac atcaatgtct   480
tacagccatt cctggggtca gggaggctct gagagcaaaa gcattacagt aggttcaagt   540
tcgggagtta ctgttcagtt aaacccggga gagtcggttg aagctgtact gacagcaagc   600
agaggtgtaa tgaaggtaag gattgtttac ctggcacatc tgacaggcag tactgctgtc   660
aattataacc cgacttacaa agaccaccat ttctggtctc ttcccattac cggtgttatg   720
ggtgctgcaa gcctctcaac taccagggaa tttacagaag atattgagat cggctactac   780
tcagacgcaa aaatagaact gagagacccg acagggcagt taaaggcaac attcctggca   840
gccaataagc cagcaattga aaaaatagca gtcaaagcag tgtaa                  885

SEQ ID NO: 46      moltype = DNA   length = 879
FEATURE             Location/Qualifiers
source              1..879
                    mol_type = other DNA
                    organism = Yokenella regensburgei
SEQUENCE: 46
atgggtatta atgtacaagt taacactgat gctgacccga agaaaacgac ggtcagcgct    60
agcggctcta tccaacatgt tatcaccggt aatgaagtta atagttttgg acttagcgac   120
tcagcgttga aagacgcagt ggctaaatat tttggtaaaa gaccaaatga tgcatatttca   180
aagagcccca cccctggggg ggatctgtat aaaacttacg gctgggaaca agtacaaacg   240
gtgttggtcg cgcgaagtgc ccaggtgctc tcggtcaatt caagcccctc aatcatcaag   300
accgtgattt tgaagaacaa ttcgaataaa cctgccacat tcaacgccag tgttagtgat   360
aatattacta atagcgttga aaccaactgg aacgtaacaa cctcggtgga tttctccgaa   420
accgtcagct atgaagttag ctttgaaggc cttggcagcg ttggcggctc aacaacatgg   480
agctttggca tgagcttcgg cgttggagga tccaaaagtg agagtatcag tattgggtcc   540
gaccaaggcg ttaccgtaga tcttgatcct ggtgagtccg ttgaagttca gctcaccgcc   600
agcatcggct cattaagagc gcgggtgttc tatgatgtgt atcttactgg ctatagcgcc   660
gtaaattaca accccacctt taaagaccac cacttctggg cattgaatat tggcgatgtg   720
atgagtgctg tgtggaattt cgaataaccgg cagatcacag aagacatcac cgtgggttat   780
tactctaatg cacacaggtt at tctatccaac gcgaaaaaaa ccgttctgcg agctcttgct   840
gttccactgg aaaaattccgt gccggtggat gccggttaa                          879

SEQ ID NO: 47      moltype = DNA   length = 864
FEATURE             Location/Qualifiers
misc_feature        1..864
                    note = Dickeya species
source              1..864
                    mol_type = other DNA
                    organism = unidentified
SEQUENCE: 47
atgtcaataa aagttgatat cactgcatca tcagacaacc atcaaacgat agccacggct    60
acaggaaatg atatttccgt tatcagcaat gaagaaagag gtactttca gctaaacgat    120
caacagttaa agagggcagt tgaagtttat tttggcaaaa aaccaaatga cgcatacctt   180
tctagtccta cgccctgggg ggatttatat aagacctaca attggcagca ggttatgaga   240
accttacagc cggtaagcac aagggtcata agccaaaact caacaccggt cattgttatg   300
gaacaggatt ttgttaataa cagttctgtt cctgctgttt ataatgtaaa aatctcacaa   360
```

```
agtgttcaga acacagtaaa atccagctgg aatactggag gaaagctaac tgtaggtcag  420
aaagttaagt atggcatatc ctttctggga acaggtggcg ggggcgagtc atctatatcg  480
tatgaacagt cgtggggaat tggcggtgaa caatctacga ctataacgtt aggaactgaa  540
tccggcttgc aggttactct acagccaggc caggccgtta cggcagagct ggtcgcatcc  600
agaggatcga tgaaagttca ggtagattat caggcgtctc tttctggaat cagtgcggtt  660
aattataacc ccacctataa agaccatcat ttttggggac ttcccatcac tcagatcatg  720
agaagttcaa acataagtaa tgcgatagtt tcatctgaaa taatcgatat cggatttttac 780
gctgattcaa aagttattct tcgcgacaaa aataccggtg gagttttcag aacatttaat  840
cttttcgaca aacacaccga ctag                                        864
```

```
SEQ ID NO: 48        moltype = DNA  length = 864
FEATURE              Location/Qualifiers
misc_feature         1..864
                     note = Dickeya species
source               1..864
                     mol_type = other DNA
                     organism = unidentified
SEQUENCE: 48
atgtcaataa aagttgatat tactgcatca tcagacaacc atcaaacgat agccacagct  60
acaggaaatg atattgccgt tatcagcaat gaagaaagag gtactttttca gctaaacgat 120
caacagctaa agagggcggt tgaagtttat tttggcagaa aaccgaatga tgcatacctt 180
tctagcccta cgccctgggg ggatttatat aagacctaca attggcagca ggttatgaga 240
accttacagc cggtaagcac aagggtcatt agccaaaact caacaccggt tattgttatg 300
gaacaggatt ttgttaataa cagctctgtt cctgctgttt ataatgtaaa aatctcacaa 360
agtgttcaga ataccgtaaa atccagctgg aataccggag gaaagttaac cgtagggcag 420
aaagttaagt atggcatatc ctttctggga acgggtggaa ggggcgagtc atctatatcg 480
tatgaacagt cgtggggaat tggcggtgaa caatcgacga ctataacgtt aggaactgaa 540
tccggcttgc aggttactct acagccaggc caggccgtta cagcgagct ggtcgcatcc 600
agaggatcga tgaaagttca ggtagattat caggcgtctc tttctggaat cagtgcggtt 660
aattataacc ccacctataa agaccatcat ttctggggac ttcccatcac tcagatcatg 720
agaagttcaa atataagtaa ctcgatagtt tcatctgaaa taatcgacat cggatttttac 780
gctgactcaa aagttattct tcgcgacaaa aataccggtg gggtgttcag aacgtttaat  840
cttttcgaca aacacaccga ctag                                        864
```

```
SEQ ID NO: 49        moltype = DNA  length = 885
FEATURE              Location/Qualifiers
source               1..885
                     mol_type = other DNA
                     organism = Methanosarcina mazei
SEQUENCE: 49
atgggaattc aaataagcat aaaggcagga gctgacgcat caacttccag cgtcagagca  60
tcgggaagtg tacagcacat catcacagac aatgagagaa agacattcgg cattgaagac 120
tctggcctca agagtgcagt tgaaaagtat tttggaaaga agccgaatga tgcctatctt 180
cacagcccta ctccatggga cgacctttac aaaaacatatg gatgggctga ggttcagaca 240
atactggacc tcaagagttc aacaataacc gggattactt cagaaccggt tatagtggca 300
accaagaaat tcgtcaacag cagcacaaag gtagccactt cgatgccag catttcagac 360
caggtcaatg ataccacgga aagcaactgg tctgaaacgg acacaatcga tgtaggcag 420
aagattactt atgaggtcag ctttctggga gccggaggag ggggagaaac atcaatgtct 480
tacagccatt cctggggtca gggaggctct gagagcaaaa gcattacagt aggttcaagt 540
tcgggagtta ctgttcagtt aaacccggga gagtcggttg aagctgtact gacagcaagc 600
agaggtgtaa tgaaggtaag gattgtttac ctggcacatc tgacaggcag tactgctgtc 660
aattataacc cgacttacaa agaccaccat ttctgggctc ttcccattac cggtgttatg 720
ggtgctgcaa gcctctcaac taccagggaa tttacagaag atattgagat cggctactac 780
tcagacgcaa aaatagaact gagagacccg acaggacagt taaaagcaac attcctggca 840
gccaataagc cagcaattga aaaaatagca gtcaaagcag tgtaa                 885
```

```
SEQ ID NO: 50        moltype = DNA  length = 885
FEATURE              Location/Qualifiers
source               1..885
                     mol_type = other DNA
                     organism = Methanosarcina mazei
SEQUENCE: 50
atggaaattc aaataagcat aaaggcagga gctgacgcat caacttccag cgtcagcgca  60
tcgggaagtg tacagcacat catcacagac aatgagagaa agacattcgg cattgaagac 120
gccggcctca agagtgcagt agaaaaatat tttgggaaga aaccgaatga tgcatatctt 180
cacagtccca ctccatggga cgacctttac aaaaacatacg ggtgggctga agttcaaaca 240
atactggacg tcaagagttc aacagtgacc gggattactt cagaaccagt tatagtggca 300
accaagaaat tcgtcaacag cagcacaaag gtagccactt cgatgccgac catttcggac 360
caggtcaacg ataccacgga aagcaactgg tctcagacga cacaatcga tgtagggcag 420
aagattactt atgaagtcag cttcctggga gccggaggag ggggagaaac gtccatgtct 480
tacagccatt cctggggtca gggaggctct gagagcaaaa gcattacagt tggttcaagt 540
tcgggagtta ctgttcagtt aaacccggga gagtcggttg aagctgtatt gaccgcaagc 600
agaggcgtaa tgaaggtaag gattgtttac ctggcacatc tgacaggcag tactgctgtc 660
aattataacc cgacttacaa agaccaccat ttctgggccc ttcccattac cggtgttatg 720
ggtgctgcaa gcctctcaac taccagggaa tttacagaag atattgagat cggctactac 780
tcagacgcaa aaatagaact gagagacccg acaggacagt taaaggcaac attcctggca 840
gccaataagc cagcaattga aaaaatagct gtcaaagcag tgtaa                 885
```

```
SEQ ID NO: 51        moltype = DNA  length = 915
```

```
FEATURE                   Location/Qualifiers
source                    1..915
                          mol_type = other DNA
                          organism = Methanosarcina barkeri
SEQUENCE: 51
atatttaatt ggtttcatac agaaaagtat gggattgaaa tcagcataaa ggcgggtgca   60
gatgcagcaa cttcaagcgt cagcgcttcg ggaagtgtac atcacattat cacggataaa  120
gagagaaaga catttggcat tgaagattca ggtctcaaga gtgcagttga aaagtatttc  180
ggaaagaaac ctaatgatgc ttatcttcac agccccactc cctgggataa cctctacaaa  240
acatacggct ggagtgaggt tcggacgata ctggatgtca agagtgcaaa aataaccggg  300
attacttcag aaccagtaat agtggcaaca aagaaattcg tcaatagcag ctcaaaaaag  360
gtaactttcg atgccggcat ttcggaccag gtaaccaata ccacagagag caactggtct  420
cagacggaca caatcgatgt agggcagaag attacatatg atgtcagctt cctgggagcc  480
ggtggaggag gagaaacctc aatgtcctac agccattcct ggatccagtt tggatctgaa  540
agcaaaagta ttacagtcgg ctcaagctca ggagtaagtg tagaattgga acctggcgag  600
tcaattgaag ccgtactgtc agcaagccgg ggtgtaatga aggtaaggat tgtttacatg  660
gcccatctaa caggtagtac agctgtcaat tataacccga cttacaaaga ccatcatttc  720
tggtctcttc ctattactgg cgttatgagt gctgccagtc tctcgactaa cagagaattt  780
acggaagata tcgagatcgg ctactactca gacgcgaaag tagaactaag aaacccgcag  840
ggtcaagtaa aagcaacatt tttagcggct aataaacccg cagttgaaaa agtgccaatt  900
aaaacagcag tttaa                                                    915

SEQ ID NO: 52           moltype = DNA   length = 879
FEATURE                   Location/Qualifiers
misc_feature             1..879
                          note = Methanosarcina species
source                    1..879
                          mol_type = other DNA
                          organism = unidentified
SEQUENCE: 52
atgggtattg aaattagtgt taatgcgggg tcagacacag ctacttcaag tgtcaatgcc   60
tcaggaagcg tacagcacat aatcaccgat aaagaaagaa cgacattcag cattcaggac  120
ggaggtctta aggatgccgt taacaagtat tttgggaaga gaccaaatga cgcatattta  180
cacagcccta cccctggga cgacctttac aaaacatatg gttggcctga agtagagaca  240
gtgctcgtcg tccagagtgc aacaataaga gggattacct cggagcctgt gattgtggca  300
acaaagactt ttagcaacag cagcagtaaa aaagcaactt tcgatgccag catttcggac  360
caggtcacca atactgtgga gagcaactgg tcccaaacgg acacgatcga ggtagggcag  420
aagtttacat ataacgtcag tttcctggga gccggcggag ggggagaaac atccatgtca  480
tacagccatt cctgggggca gggtggctct gagagcaaga gcatcacggt cggatcgagt  540
tcggagtca aggttgagtt ggaacccggg gaatcggttg aagcccagct cacagccagc  600
agaggggtga tgaaggtcag gattgtttac aaagcatatc tgatcggctc cactgctatc  660
aactacaacc caacgtacaa ggaccaccat ttctgggctc ttggcatcgg cggggttatg  720
ggtgcagcat ccctgccgac caccagggaa tacacggaag acatcgagat tggctactac  780
tcaaactcaa aaatagaact cagagacccg gcaggtcagc tgaaggggga gttcttcgag  840
gctgataaag cagcagtagc tgacaatgta gctttgtaa                         879

SEQ ID NO: 53           moltype = DNA   length = 549
FEATURE                   Location/Qualifiers
source                    1..549
                          mol_type = other DNA
                          organism = Methanosarcina barkeri
SEQUENCE: 53
atgggtattg aaatcagcat aaaggcgggt gcagacgcag caacttcaag cgtcagcgct   60
tcggaagtg tacagcacat tatcacagat aaagagagaa agacatttga cattgaagat  120
tcaggtctca agagtgcagt tggaaagtat ttcggaaaga aacctaatga tgcttatctt  180
cacagcccca ctccctggga tgacctctac aaaacatacg gctggagtga ggttcagacg  240
atactggatg tcaagagtgc aaaaataacc gggattactt cagaaccagt aatagtggca  300
accaagaaat tcgtcaatag cagctcaaaa aaggccactt tcgatgccag catttcggac  360
caggtaacca ataccacaga gagcaactgg tctcagacgg acacaatcga tgtagggcag  420
aagattacat atgatgtcag cttcctggga gccggtggag gaggagaaac ctcaatgtcc  480
tacagccatt cctgggggca gggtggatct gaaagcaaaa gtattacagt cggctcagct  540
caggagtaa                                                           549

SEQ ID NO: 54           moltype = DNA   length = 747
FEATURE                   Location/Qualifiers
misc_feature             1..747
                          note = internal pool YJP-3_D0530001_NODE_186_185
source                    1..747
                          mol_type = other DNA
                          organism = unidentified
SEQUENCE: 54
atgtctatta gtataaaggt ttatgcatct atatatgagg ggcaatcccg catctcttac   60
ggaggaaggg atgtttcatt gatatctcag caagaaagaa ataccttcaa attaaatgat  120
aatcaattaa aaaatgcagc caagcgagta tttggtcgca ggccaaatga tgcttttta  180
cgtagcccaa cccttggaa tctttatgag aataatcgtt ggatgcaaac tcaacgtagt  240
ttatttatcc aaggtgtcag gttaattgag cgttcatcaa gcccagttat cgtagcaaat  300
caagagtttg tcaactcaag ttctgttcct gcaaaattta atgcagccat cgagcaaaat  360
gtttctaata ccgtaagctc acagtggtca actggaggaa cgctctcaat aggacaaact  420
ataaaagtcg aagttggttt tcttggaaca ggagtgggct cagaaacatc attgagttac  480
```

```
gaacaatcat ggggcatttc tggcgagcgg tcccagtcaa ttactgtcgg tacgtcctct  540
ggtgtggaag tagaattgca accagggcaa ccagggcaac cagcgccccg cccaaccagc  600
cgacgcggga ctgtacccac atcagcaatg ccggcagcac cagcagcaac accatcagaa  660
aggcctggcg acagtgctca taccgcgccc gcgccagggc aaagcccggc agcagaaaca  720
gcatcagcgc cagtcctgtg gcaataa                                       747
```

```
SEQ ID NO: 55              moltype = DNA   length = 885
FEATURE                    Location/Qualifiers
source                     1..885
                           mol_type = other DNA
                           organism = Methanosarcina mazei
SEQUENCE: 55
atgggaattc aaataagcat aaaggcagga gctgacgcat caacttccag cgtcagcgca  60
tcgggaagtg tacagcacat catcacagac aatgagagaa agacattcag cattgaagat  120
gcaggtctca agagtgcagt tgaaaaatat tttgggaaga aaccgaatga tgcatatctt  180
cacagcccta ctccatggga cgacctttac aaaacatatg ggtgggctga agttcaaaca  240
atactggacg tcaggagttc aacaataacc gggattactt cagaaccggt tatagtggca  300
accaaaaaat tcgtcaacag cagcaaaag gtagccactt tcgatgccag catttcagac  360
caggtcaatg ataccacgga aagcaactgg tctgaaacgg acacaatcga cgtagggcag  420
aagattactt atgaggtcag ctttctggga gccggaggag ggggagaaac atcaatgtct  480
tacagccatt cctggggtca gggaggctct gagagcaaaa gcattacagt aggttcaagt  540
tcgggagtta ctgttcagtt aaacccggga gagtcggttg gacagcaagc  600
agaggtgtaa tgaaggtaag gattgtttac ctggcacatc tgacaggcag tactgctgtc  660
aattataacc cgacttacaa agaccaccat ttctgggctc ttcccattac cggtgttatg  720
ggtgctgcaa gcctctcaac taccagggaa tttacagaag atattgagat cggctactac  780
tcagacgcaa aaatagaact gagagacccg acaggacagt taaaggcaac attcctggca  840
gccaataagc cagcaattga aaaaatagca gtcaaagcag tgtaa           885
```

```
SEQ ID NO: 56              moltype = DNA   length = 885
FEATURE                    Location/Qualifiers
source                     1..885
                           mol_type = other DNA
                           organism = Methanosarcina mazei
SEQUENCE: 56
atgggaattc aaataagcat aaaggcagga gctgacgcat caacttccag cgtcagcgca  60
tcgggaagtg tacagcacat catcacagac aatgagagaa agacattcgg cattgaagat  120
gcaggtctca agagtgcagt tgaaaaatat tttgggaaga aaccgaatga tgcatatctt  180
cacagcccta ctccatggga cgacctttac aaaacatatg ggtgggctga agttcaaaca  240
atactggacg tcaggagttc aacaataacc gggattactt cagaaccggt tatagtggca  300
accaagaaat tcgtcaacag cagcacaaag gtagccactt tcgatgccag catttcggac  360
caggtcaacg ataccacgga aagcaactgg tctcagacag acacaatcga tgtagggcag  420
aagattactt atgaagtcag cttcctggga gccggaggag ggggagaaac gtccatgtct  480
tacagccatt cctggggtca gggaggctct gagagcaaaa gcattacagt tggttcaagt  540
tcgggagtta ctgttcagtt aaacccggga gagtcggttg aagctgtatt gaccgcaagc  600
agaggcgtaa tgaaggtaag gattgtttac ctggcacatc tgacaggcag tactgctgtc  660
aattataacc cgacttacaa agaccaccat ttctgggccc ttcccattac cggtgttatg  720
ggtgctgcaa gcctctcaac taccagggaa tttacagaag atattgagat cggctactac  780
tcagacgcaa aaatagaact gagagacccg acaggacagt taaaggcaac attcctggca  840
gccaataagc cagcaattga aaaaatagca gtcaaagcag tgtaa           885
```

```
SEQ ID NO: 57              moltype = DNA   length = 885
FEATURE                    Location/Qualifiers
source                     1..885
                           mol_type = other DNA
                           organism = Methanosarcina mazei
SEQUENCE: 57
atgggaatcc aaataagcat aaaagcaggt gctgacgcat caacttccag cgtcagcgct  60
tcgggaagtg tacagcacat catcacagac aatgagagaa agacattcgg cattgaagac  120
tctggcctca agagtgcagt tgaaaaatat tttgggaaga aaccgaatga tgcatatctt  180
cacagcccta ctccatggga cgacctttac aaaacatatg ggtgggctga agttcaaaca  240
atactggacg tcaggagttc aacaataacc gggattactt cagaaccggt tatagtggca  300
accaaaaaat tcgtcaacag cagcacaaag gtagccactt tcgatgccag catttcgac  360
caggtcaatg ataccacgga aagcaactgg tctgaaacgg acacaatcga cgtagggcag  420
aagattactt atgaggtcag ctttctggga gccggaggag ggggagaaac atcaatgtct  480
tacagccatt cctggggtca gggaggctct gagagcaaaa gcattacagt aggttcaagt  540
tcgggagtta ctgttcagtt aaacccggga gagtcggttg aagctgtact gacagcaagc  600
agaggcgtaa tgaaggtaag gattgtttac ctggcacatc tgacaggcag tactgctgtc  660
aattataacc cgacttacaa agaccaccat ttctgggctc ttcccattac cggtgttatg  720
ggtgctgcaa gcctctcaac taccagggaa tttacagaag atattgagat cggctactac  780
tcagacgcaa aaatagaact gagagacccg acagggcagt taaaggcaac attcctggca  840
gccaataagc cagcaattga aaaaatagca gtcaaagcag tgtaa           885
```

```
SEQ ID NO: 58              moltype = DNA   length = 885
FEATURE                    Location/Qualifiers
misc_feature               1..885
                           note = Methanosarcina species
source                     1..885
                           mol_type = other DNA
                           organism = unidentified
```

```
SEQUENCE: 58
atgggaattc aaataagcat aaaggcagga gctgacgcat caacttccag cgtcagcgca   60
tcgggaagtg tacagcacat catcacagac aatgagagaa agacattcgg cattgaagac  120
gccggcctca agagtgcagt agaaaaatat tttgggaaga aaccgaatga tgcatatctt  180
cacagtccca ctccatggga cgacctttac aaaacatacg ggtgggctga agttcaaaca  240
atactggacg tcaagagttc aacagtgacc gggattactt cagaaccagt tatagtggca  300
accaagaaat tcgtcaacag cagcacaaag gtagccactt tcgatgccag catttcggac  360
caggtcaacg ataccacgga aagcaactgg tctcagacag acacaatcga cgtagggcag  420
aagattactt atgaggtcag ctttctggga gccggaggag ggggagaaac gtccatgtct  480
tacagccatt cctgggggtca gggaggctct gagagcaaaa gcattacagt tggttcaagt  540
tcgggagtta ctgttcagtt aaacccggga gagtcggttg aagctgtatt gaccgcaagc  600
agaggcgtaa tgaaggtaag gattgtttac ctggcacatc tgacaggcag tactgctgtc  660
aattataacc cgacttacaa agaccaccat ttctgggccc ttcccattac cggtgttatg  720
ggtgctgcaa gcctctcaac taccagggaa tttacagaag atattgagat cggctactac  780
tcagacgcaa aaatagaact gagagacccg acaggacagt taaaggcaac attcctggca  840
gccaataagc cagcaattga aaaaatagct gtcaaagcag tgtaa             885

SEQ ID NO: 59          moltype = DNA  length = 906
FEATURE                Location/Qualifiers
misc_feature           1..906
                       note = Proteobacteria species
source                 1..906
                       mol_type = other DNA
                       organism = unidentified
SEQUENCE: 59
atgtcaatat cagtcagaat tagagctggt tcaaacatgc aaaattctag cgtatatgct   60
gagggttctg aatttcatat tatcacagat tcagaaagat attcatttaa tattggtagt  120
gatgcagatt taaaaaatgc tgtagggaaa tattttggta aaaatccaaa tgatgcctat  180
ttacatagtc ctactccatg gggcgattta tataaaactt atggctggcc tcaaactcaa  240
actaatttga ctgtggcaag ttcaactata gcggaaatca cctcagaacc ttccatagta  300
aaaacgcaaa catttaaaaa caatagcagt gttgcaggaa catttgatgt gagtatttcg  360
gaagaagttt caaatacagt tgaaagcaat tggaataata gttctagtgt aagttttgga  420
cagtctatta gttataatgt ttcttttta ggaacaggag gtggcggtga aacaagtttt  480
gggtttgaac aaacttgggg aaaaggaggt tctaatagta aatcgttac tgtaggttct  540
tcttctggtg ttactgtatt attacaaccc ggagagtctg taaaatctat tttgaccgca  600
actcgtggat atatgaatgt acgtctcgtt tacagagcaa atttaagtgg aacttgtgct  660
gtaaactaca accccacatt tcaaggtcat cattttgggg gattaggaat taataatgta  720
gtcaatgcag caggaagttc aaataatgtc caaattgtag aagatataaa aataggatat  780
tattctgatt ccgaacttat tttagaagat ttaaatggta atagaagaat ttatcatttc  840
gcaattccag gcatgcctcc agcgggcaaa agtgctccaa cttcatctcg agaagcaact  900
ctttaa                                                        906

SEQ ID NO: 60          moltype = DNA  length = 885
FEATURE                Location/Qualifiers
source                 1..885
                       mol_type = other DNA
                       organism = Anaerobacillus macyae
SEQUENCE: 60
atgagccaag acggtattga gattagtatc aagcctggtc tggacaaaga atcatctagc   60
gtgacagcag ttggaagtgt tcgtcacatt attaccaaaa aggaaatgaa gaattttgga  120
gttgagagag atcaattaaa gaaatccgta ggaaatttt tcggccaagc gcctaaggat  180
gtatttcttt atagtccgac accatggggt gatctgttta gaaaatttgg tggagatgaa  240
acctcaactg ttttgaaggt taaggacgct aaagtaattg atattacctc taaaccagtt  300
gttatatcaa gccaaacgtt taagaacgac agtagtagtc atgctacatt tgactgtgca  360
attaaagatt cagtaagtga aacagttgaa agttcatgga gtagttcaaa taagattgag  420
gcttcgcaag ctattaatta tacagtaggc ttcccaggtg gtgatgctgg aggtgaaact  480
aaaatagctt actcccattc atggggagaa gaaacatctc attcaaaaca aatagaggtg  540
ggccgttctt ctggcgtgca tgtgaattta gaaccaggac aagcagtaga agcgataata  600
aatgcaagtc gagggagtat gaaagtggaa atagtgtacg aagcaaaatt gtctggttct  660
ttttggacta attatccaaa caaatgtgaaa aaacatcatt tttggcgttt taacatagat  720
caggtatttta atactaataa aatcccaaat tccatcattg tcacagagaa catcttagtt  780
ggttttttatg caaactcaac aattgatctt aaagatgttg aaacgcaaag atctcttaat  840
tccgttattg cagataattc cgaaacactt agctttacca cttaa             885

SEQ ID NO: 61          moltype = DNA  length = 876
FEATURE                Location/Qualifiers
source                 1..876
                       mol_type = other DNA
                       organism = Enterobacter cloacae
SEQUENCE: 61
atgagaataa atatacagtt aagggaaaac attgaaagca gtattgttaa cggcagtggg   60
gtgttatcag gtgtattaac aaacactgag caacaaacat tcggtcttga tgaaagacat  120
attcggtggg ctgtttgctc tatcagtggc agggagccga atgatgtttt cgtccgaagt  180
ccaacccctt ggggtgatct gtatcaaaga tataactggc ggcaggttca ccgtatgact  240
gagataagga gtgcaagatt tcttgagttt gagactgtcc cagagatagt tgcagaaact  300
gaactcgtaa ataacagctc agtttcaggt gtgtttacag caaacatgaa tacaactgta  360
accaatacca tgtcatctgg ctggcatgtt gatcacggca ttactgttgg gcaaagcatc  420
agatatggtt ttacaaaggt gggggggagaa acctcttttg aatatactca tggatggggt  480
gaaaatggcg aagtatctga atctgtctca ttgagtacag gatccggcgt gaccgtccag  540
```

-continued

```
cttgaaccgg gacaagcagt cgtggcatta atgatagcca gtaggggaca agcaagagtc  600
caggtggaat atgtgtcgta tttaaatggt cttgtcgcta caaattataa cccgcgccac  660
aacggtcacc attttctagg atatgggggta gagtctgtac taagagcgct cagcaattca  720
aattctcgta tatccactga aacaataact attgggatgt actcaagagc cagagttgag  780
ctgagagata aagaaacaaa acgtttattg cgaacagtat ggcttgatga ggaaatcatt  840
cctggtggag tcgttgttcc gcagcctgaa ttatga                            876
```

```
SEQ ID NO: 62          moltype = DNA   length = 876
FEATURE                Location/Qualifiers
source                 1..876
                       mol_type = other DNA
                       organism = Pectobacterium betavasculorum
SEQUENCE: 62
atgacaatga gaataaatgt aataatccaa gaaaatattg aaaatagtgt ggttaatggt  60
agcggtatta catcaggtat tattacagat gtagaacgcc gcacatttaa tcttgaagat  120
actcagttga aaagagcatg cggattactt gtcggaaaag aacccacgga tgctttcttg  180
cgcagcccaa caccctggaa tgatctttt gttacttata attgggctca aacacaaaga  240
aataccagtg tcagaacagc taggttcgtg ggacataatg ctgtacctga gttggtttca  300
gagaaagaac tagtaaataa cagctctatt ggtgcaacct ttaatgcaaa tctatctaca  360
actgtatcta atacggtgtc atctagttgg tcatcttctc attcaatctc tgtaggacag  420
gaaattgaat ataaaatatt ggggattggt ggtagcacat cttttgatta tacgcatgag  480
tggggagtcg gtggtgagca atcacaaact atcgaactaa atcgtggtgc aggtgtggaa  540
gtttacctcg aacctggtca ggcagttagc gcacagatgg tcgctagtag gggaaatgct  600
caggttgcta ttgaatatct gtcatattta acgggtggtg cagcaatgaa ttattaccct  660
cgttacgacg gacatcattt tagatggcgt gctatttctc gtataatgga tgttgggggt  720
atatccaatc aagtaataac gagggagaat ttaaatattt ctgtatattc tagtgcccgg  780
ctggaattga tagatataaa aacgaaaaaa ctattaagaa catattattt gggggatatc  840
ttatctgtgg gggaggcgaa tgctcaagat gattga                            876
```

```
SEQ ID NO: 63          moltype = DNA   length = 885
FEATURE                Location/Qualifiers
source                 1..885
                       mol_type = other DNA
                       organism = Sodalis praecaptivus
SEQUENCE: 63
atgaaaatta atatacagcc aagagaaagt atcgaggaca gtgttgtaaa cggaagcggc  60
gttttgtcgg aggtcataac cagcgatgag caacgcctat tcaagcttga agagcccgat  120
atcatcaggg ctattactgc cctgaatggg agggaaccca atgatgtgtt tgtccgcagt  180
cctacaccct gggggggacct gtacagcagc tatcgctggc ggcaggttca caaaaacacg  240
gagattttca gcgccaaatt tctacaattt agttcagcgc cagagatcgt ttcggaaacc  300
gaattggtca ataacagtaa ggtggcgggt gaattcaacg tcaatttatt aaccgaagtt  360
cttaataccg tttcctccgg atggaaggtg gaggatggga tttccgttgg gcaaaaagtc  420
acttacggcg tagattggct caaaggcgaa acctcttttg agtatactca cggctggggg  480
gtgaatggtg aagtgtcgga gtctgtcacc cttacgaccg gcgccggggt gacggtcttg  540
ctggcccccg gtcaggcagt cgttgcgcag atgattgcaa gccggggccg ggccagagtc  600
gaagtggaat atctttctca cctcgatggt ctcgtcgcaa tgaactatga gcctccgtat  660
aaggaacatc attttttggg gcgagatgtc gcgtctatat tgagacaaaa ttcgacgcct  720
aacgcatgtc gttcaactga agttatagaa attgccatgt attccaaggc gcgagtagag  780
ttacgggata aagcaaacaa agatttactg aaaacggttt ggctgaatga ggaggcaaaa  840
cctatcggca atagcgtcgc ctcggcagaa ctttgcagag agtag                  885
```

```
SEQ ID NO: 64          moltype = DNA   length = 858
FEATURE                Location/Qualifiers
misc_feature           1..858
                       note = Proteobacteria species
source                 1..858
                       mol_type = other DNA
                       organism = unidentified
SEQUENCE: 64
atgtctattt tattgtctgt tattgctgga atgagtgcgg atcattcatc tgcatccgga  60
tcgggtcagg aaattcatat cattacggat aaagaaagag aatcatttgg tataggaaat  120
gaccaagttt taaaaaaggc ggtggaagct tattttggaa aatctcctga tgatgtttat  180
ttaaaaagtg acactccatg ggacgatctt tataaaacat acaactggtc acaagtacag  240
acaaattata gagtaagaga tgttcaaatt cttgaaataa catcccaacc agaaattctt  300
gcaaagaaaa cctttgaaaa taaaagtagc aagagtgtta cctataatgc ttctatttca  360
gataccagag caaatactct tgaaactcat tggtcacaat ccacaaataa atctgttgga  420
ttttctataa aagccagctt ttccgttccc ggagtttttcg gatttgaggg aggcagcacc  480
tttaattttg atagcacttg gggcgaaggt ggttttcaat caaccacaac gactgtgggc  540
acaaccacag gtattattgt aaccttagac cctggagaaa aagtcgaagc ccacttaaat  600
gccacacgag gccatctgaa agtgagagtc aattacgata cctatttaac cggcattaca  660
gcagtaaatt atgctcaaac atataaagaa catcactttt ggggattgcc tattgataaa  720
gttcttaaat catcaggaat aaacaacaat caaattgtga ctcaggatct caactttagc  780
tactattccg atgcccatgt ggtcgtttac gatcaaaaag gaagagaaaa aagaacaatt  840
aatgcttcat ttaattga                                                858
```

```
SEQ ID NO: 65          moltype = AA   length = 295
FEATURE                Location/Qualifiers
REGION                 1..295
                       note = Chimeric polypeptide
```

-continued

```
source                  1..295
                        mol_type = protein
                        organism = Synthetic construct
SEQUENCE: 65
MAISIAINAG QSSSASTVIA TGTVQNVITD TERTLFNIQD GSLKAAVSAY FGRSPNDAYV  60
CSPTPWGDLY QTYNWPQVQA TLSVVSARIV SETSNPIALN TNTFTNHSSV PAEFNCGVTQ  120
EVTVTAESNW SSSSEVGISQ TISYGISFLG AGGGGETSMS YSHSWGQGGS ESKSITVGSS  180
SGVSVELEPG ESIEAVLSAS RGVMKVRIVY MAHLTGSTAV NYNPTYKDHH FWSLPITGVM  240
SAASLSTNRE FTEDIEIGYY SDAKIELRNP QGQLKATFLV ANKPAVEKVP IKTAV       295

SEQ ID NO: 66          moltype = AA  length = 295
FEATURE                Location/Qualifiers
REGION                 1..295
                       note = Chimeric polypeptide
source                 1..295
                       mol_type = protein
                       organism = Synthetic construct
SEQUENCE: 66
MAISIAINAG QSSSASTVIA TGTVQNVITD TERTLFNIQD GSLKAAVSAY FGRSPNDAYV  60
HSPTPWDDLY KTYGWSEVQT ILDVKSAKIT EITSEPVIVA TKKFVNSSSK KATFDASISD  120
QVTNTTESNW SQTDTIDVGQ KITYDVSFLG AGGGGETSMS YSHSWGQGGS ESKSITVGSS  180
SGVSVELEPG ESIEAVLSAS RGVMKVRIVY MAHLTGSTAV NYNPTYKDHH FWSLPITGVM  240
SAASLSTNRE FTEDIEIGYY SDAKIELRNP QGQLKATFLV ANKPAVEKVP IKTAV       295

SEQ ID NO: 67          moltype = AA  length = 289
FEATURE                Location/Qualifiers
REGION                 1..289
                       note = Chimeric polypeptide
source                 1..289
                       mol_type = protein
                       organism = Synthetic construct
SEQUENCE: 67
MGIEISIKAG ADAATSNVSA SGSVQHIITD KERKTFDIED AGLKSAVEKY FGKKPNDAYL  60
CSPTPWGDLY QTYNWPQVQA TLSVVSARIV SETSNPIALN TNTFTNHSSV PAEFNCGVTQ  120
EVTVTAESNW SSSSEVGISQ TISYGISFLG AGAQGETALS FTQTWEQGGS QSESVTLGSS  180
AGVTLTLQPG QTVEAILSAS KGVLTVEVEY QITLAGVTAV NYNPTYQGHH FWALDINNVM  240
SAGKLSNVIT SKETIVIDYF TNTTITVQDP ESQDVIRTLV TSARPGISS              289

SEQ ID NO: 68          moltype = AA  length = 295
FEATURE                Location/Qualifiers
REGION                 1..295
                       note = Chimeric polypeptide
source                 1..295
                       mol_type = protein
                       organism = Synthetic construct
SEQUENCE: 68
MGIEISIKAG ADAATSNVSA SGSVQHIITD KERKTFDIED AGLKSAVEKY FGKKPNDAYL  60
CSPTPWGDLY QTYNWPQVQA ILDVKSAKIT EITSEPVIVA TKKFVNSSSK KATFDASISD  120
QVTNTTESNW SQTDTIDVGQ KITYDVSFLG AGGGGETSMS YSHSWGQGGS ESKSITVGSS  180
SGVSVELEPG ESIEAVLSAS RGVMKVRIVY MAHLTGSTAV NYNPTYKDHH FWSLPITGVM  240
SAASLSTNRE FTEDIEIGYY SDAKIELRNP QGQLKATFLV ANKPAVEKVP IKTAV       295

SEQ ID NO: 69          moltype = AA  length = 295
FEATURE                Location/Qualifiers
REGION                 1..295
                       note = Chimeric polypeptide
source                 1..295
                       mol_type = protein
                       organism = Synthetic construct
SEQUENCE: 69
MGIEISIKAG ADAATSNVSA SGSVQHIITD KERKTFDIED AGLKSAVEKY FGKKPNDAYL  60
CSPTPWGDLY QTYNWPQVQA TLSVVSARIV SETSNPIALN TNTFTNHSSV PAEFNCGVTQ  120
EVTNTTESNW SQTDTIDVGQ KITYDVSFLG AGGGGETSMS YSHSWGQGGS ESKSITVGSS  180
SGVSVELEPG ESIEAVLSAS RGVMKVRIVY MAHLTGSTAV NYNPTYKDHH FWSLPITGVM  240
SAASLSTNRE FTEDIEIGYY SDAKIELRNP QGQLKATFLV ANKPAVEKVP IKTAV       295

SEQ ID NO: 70          moltype = AA  length = 295
FEATURE                Location/Qualifiers
REGION                 1..295
                       note = Chimeric polypeptide
source                 1..295
                       mol_type = protein
                       organism = Synthetic construct
SEQUENCE: 70
MGIEISIKAG ADAATSNVSA SGSVQHIITD KERKTFDIED AGLKSAVEKY FGKKPNDAYV  60
CSPTPWGDLY QTYNWPQVQA TLSVVSARIV SETSNPIALN TNTFTNHSSV PAEFNCGVTQ  120
EVTVTAESNW SSSSEVGISQ TISYGISFLG AGGGGETSMS YSHSWGQGGS ESKSITVGSS  180
SGVSVELEPG ESIEAVLSAS RGVMKVRIVY MAHLTGSTAV NYNPTYKDHH FWSLPITGVM  240
SAASLSTNRE FTEDIEIGYY SDAKIELRNP QGQLKATFLV ANKPAVEKVP IKTAV       295
```

```
SEQ ID NO: 71            moltype = DNA   length = 888
FEATURE                  Location/Qualifiers
misc_feature             1..888
                         note = Chimeric polynucleotide
source                   1..888
                         mol_type = other DNA
                         organism = Synthetic construct
SEQUENCE: 71
atggctatta gtatcgcgat caatgctggg caatcttcat ccgcgtcaac cgtcattgcc   60
acgggcacgg tccagaacgt tatcaccgac accgagcgaa ccttgttcaa catccaggat   120
gggtcgttga aagcggcggt gtctgcctat tttggccgct cgcccaatga cgcttacgtt   180
tgcagcccca cgccctgggg tgatctgtac cagacctaca actggccgca ggtacaagcc   240
acgctgtcgg tggtgagcgc aaggattgtc tcggaaacct cgaacccgat tgccctcaat   300
accaatacct tcaccaacca ctcctcggtg ccggcggagt tcaactgcgg ggtcacccag   360
gaggtgacgg tcaccgcgga aagcaactgg tcgagctcgt cggaagtcgg catcagccag   420
acgatttcct acgggatctc gttcctcggc gccggcggcg cgggcgaaac ctccatgtct   480
tactcccact cctgggggca gggcggttcg gaatcgaagt cgataaccgt gggttcgtcg   540
tccggagtgt ccgtggagct ggaacccggg gagtccatag aggcggtact gtcggcctcg   600
cggggggtaa tgaaggtacg aattgtgtat atggcgcacc tgacggggtc aacggcggtc   660
aattacaacc cgacgtataa ggaccatcac ttctggtcac tgcctatcac gggcgtcatg   720
tctgccgcct cgctgtcgac gaaccgcgag ttcacggaag acatcgagat cggctactac   780
tccgatgcca agatcgagct gcgcaaccct caaggccagc ttaaggccac cttcctcgtc   840
gccaacaagc cggcggtgga gaaggtacca atcaagacgg cggtgtaa              888

SEQ ID NO: 72            moltype = DNA   length = 888
FEATURE                  Location/Qualifiers
misc_feature             1..888
                         note = Chimeric polynucleotide
source                   1..888
                         mol_type = other DNA
                         organism = Synthetic construct
SEQUENCE: 72
atggctatta gtatcgcgat caatgctggg caatcttcat ccgcgtcaac cgtcattgcc   60
acgggcacgg tccagaacgt tatcaccgac accgagcgaa ccttgttcaa catccaggat   120
gggtcgttga aagcggcggt gtctgcctat tttggccgct cgcccaatga cgcttacgtt   180
cactcgccca cgccctggga tgatctgtac aagacctacg gctggtcgga ggtacaaacc   240
atcctggacg tgaagtccgc aaagattacg gagataacct cggagccggt tatcgtcgct   300
accaagaagt tcgtcaactc ctcctcgaag aaggcgacgt tcgacgcgtc gatctccgac   360
caggtgacga acaccacgga atccaactgg tcgcagacgg acacgatcga cgtcggccag   420
aagattacct acgacgtctc gttcctcggc gccggcggcg cgggcgaaac ctccatgtct   480
tactcccact cctgggggca gggcggttcg gaatcgaagt cgataaccgt gggttcgtcg   540
tccggagtgt ccgtggagct ggaacccggg gagtccatag aggcggtact gtcggcctcg   600
cggggggtaa tgaaggtacg aattgtgtat atggcgcacc tgacggggtc aacggcggtc   660
aattacaacc cgacgtataa ggaccatcac ttctggtcac tgcctatcac gggcgtcatg   720
tctgccgcct cgctgtcgac gaaccgcgag ttcacggaag acatcgagat cggctactac   780
tccgatgcca agatcgagct gcgcaaccct caaggccagc ttaaggccac cttcctcgtc   840
gccaacaagc cggcggtgga gaaggtacca atcaagacgg cggtgtaa              888

SEQ ID NO: 73            moltype = DNA   length = 870
FEATURE                  Location/Qualifiers
misc_feature             1..870
                         note = Chimeric polynucleotide
source                   1..870
                         mol_type = other DNA
                         organism = Synthetic construct
SEQUENCE: 73
atgggtattg agatctcgat caaggctggg gcagatgcag ccacgtcaaa cgtctctgcc   60
tcgggctcgg tccagcacat tatcaccgac aaggagcgaa agacgttcga catcgaggat   120
gcgggcctga aatcggccgt ggaaaagtat tttggcaaga agcccaatga cgcttacctt   180
tgcagcccca cgccctgggg tgatctgtac cagacctaca actggccgca ggtacaagcc   240
acgctgtcgg tggtgagcgc aaggattgtc tcggaaacct cgaacccgat tgccctcaat   300
accaatacct tcaccaacca ctcctcggtg ccggcggagt tcaactgcgg ggtcacccag   360
gaggtgacgg tcaccgcgga aagcaactgg tcgagctcgt cggaagtcgg catcagccag   420
acgatttcct acgggatctc gttcctcggc gccggcgccc agggcgaaac cgccttgagt   480
ttcacccaga cctgggagca gggcggttcg caaagtgagt cggtaaccct gggttcgagc   540
gccgagtga cctgacctt gcaacccggg cagaccgtag aggcgatact gtcggccagc   600
aagggggtac tgacggtaga agttgagtat caaataaccc tggcggggt aacggcggtc   660
aattacaacc cgacgtatca ggggcatcac ttctgggcac tggatatcaa caacgtcatg   720
agtgccggca aactgtcgaa tgtcatcacc agcaaagaaa ccatcgtgat cgactacttc   780
accaatacca cgatcaccgt gcaggaccct gaaagccagg atgtcatccg caccctcgtc   840
acctcggcca ggccgggcat cagttcataa                                 870

SEQ ID NO: 74            moltype = DNA   length = 888
FEATURE                  Location/Qualifiers
misc_feature             1..888
                         note = Chimeric polynucleotide
source                   1..888
                         mol_type = other DNA
```

```
                             organism = Synthetic construct
SEQUENCE: 74
atgggtattg agatctcgat caaggctggg gcagatgcag ccacgtcaaa cgtctctgcc    60
tcgggctcgg tccagcacat tatcaccgac aaggagcgaa agacgttcga catcgaggat   120
gcgggcctga aatcggcggt ggaaaagtat tttggcaaga agcccaatga cgcttacctt   180
tgcagcccca cgccctgggg tgatctgtac cagacctaca actggccgca ggtacaagcc   240
atcctggacg tgaagtccgc aaaagattacg gagataacct cggagccggt tatcgtcgct   300
accaagaagt tcgtcaactc ctcctcgaag aaggcgacgt tcgacgcgtc gatctccgac   360
caggtgacga acaccacgga atccaactgg tcgcagacgg acacgatcga cgtcggccag   420
aagattacct acgacgtctc gttcctcggc gccggcggcg gcggcgaaac ctccatgtct   480
tactcccact cctgggggca gggcggttcg gaatcgaagt cgataaccgt gggttcgtcg   540
tccgagtgt ccgtggagct ggaacccggg gagtccatag aggcggtact gtcggcctcg   600
cggggggtaa tgaaggtacg aattgtgtat atggcgcacc tgacggggtc aacggcggtc   660
aattacaacc cgacgtataa ggaccatcac ttctggtcac tgcctatcac gggcgtcatg   720
tctgccgcct cgctgtcgac gaaccgcgag ttcacggaag acatcgagat cggctactac   780
tccgatgcca agatcgagct gcgcaaccct caaggccagc ttaaggccac cttcctcgtc   840
gccaacaagc cggcggtgga gaaggtacca atcaagacgg cggtgtaa               888

SEQ ID NO: 75              moltype = DNA  length = 888
FEATURE                    Location/Qualifiers
misc_feature               1..888
                           note = Chimeric polynucleotide
source                     1..888
                           mol_type = other DNA
                           organism = Synthetic construct
SEQUENCE: 75
atgggtattg agatctcgat caaggctggg gcagatgcag ccacgtcaaa cgtctctgcc    60
tcgggctcgg tccagcacat tatcaccgac aaggagcgaa agacgttcga catcgaggat   120
gcgggcctga aatcggcggt ggaaaagtat tttggcaaga agcccaatga cgcttacctt   180
tgcagcccca cgccctgggg tgatctgtac cagacctaca actggccgca ggtacaagcc   240
acgctgtcgg tggtgagcgc aaggattgtc tcggaaacct cgaacccgat tgccctcaat   300
accaatacct tcaccaacca ctcctcggtg ccggcggagt tcaactgcgg ggtcacccag   360
caggtgacga acaccacgga atccaactgg tcgcagacgg acacgatcga cgtcggccag   420
aagattacct acgacgtctc gttcctcggc gccggcggcg gcggcgaaac ctccatgtct   480
tactcccact cctgggggca gggcggttcg gaatcgaagt cgataaccgt gggttcgtcg   540
tccgagtgt ccgtggagct ggaacccggg gagtccatag aggcggtact gtcggcctcg   600
cggggggtaa tgaaggtacg aattgtgtat atggcgcacc tgacggggtc aacggcggtc   660
aattacaacc cgacgtataa ggaccatcac ttctggtcac tgcctatcac gggcgtcatg   720
tctgccgcct cgctgtcgac gaaccgcgag ttcacggaag acatcgagat cggctactac   780
tccgatgcca agatcgagct gcgcaaccct caaggccagc ttaaggccac cttcctcgtc   840
gccaacaagc cggcggtgga gaaggtacca atcaagacgg cggtgtaa               888

SEQ ID NO: 76              moltype = DNA  length = 888
FEATURE                    Location/Qualifiers
misc_feature               1..888
                           note = Chimeric polynucleotide
source                     1..888
                           mol_type = other DNA
                           organism = Synthetic construct
SEQUENCE: 76
atgggtattg agatctcgat caaggctggg gcagatgcag ccacgtcaaa cgtctctgcc    60
tcgggctcgg tccagcacat tatcaccgac aaggagcgaa agacgttcga catcgaggat   120
gcgggcctga aatcggcggt ggaaaagtat tttggcaaga agcccaatga cgcttacgtt   180
tgcagcccca cgccctgggg tgatctgtac cagacctaca actggccgca ggtacaagcc   240
acgctgtcgg tggtgagcgc aaggattgtc tcggaaacct cgaacccgat tgccctcaat   300
accaatacct tcaccaacca ctcctcggtg ccggcggagt tcaactgcgg ggtcacccag   360
gaggtgacgg tcaccgcgga aagcaactgg tcgagctcgt cggaagtcgg catcagccag   420
acgatttcct acgggatctc gttcctcggc gccggcggcg gcggcgaaac ctccatgtct   480
tactcccact cctgggggca gggcggttcg gaatcgaagt cgataaccgt gggttcgtcg   540
tccgagtgt ccgtggagct ggaacccggg gagtccatag aggcggtact gtcggcctcg   600
cggggggtaa tgaaggtacg aattgtgtat atggcgcacc tgacggggtc aacggcggtc   660
aattacaacc cgacgtataa ggaccatcac ttctggtcac tgcctatcac gggcgtcatg   720
tctgccgcct cgctgtcgac gaaccgcgag ttcacggaag acatcgagat cggctactac   780
tccgatgcca agatcgagct gcgcaaccct caaggccagc ttaaggccac cttcctcgtc   840
gccaacaagc cggcggtgga gaaggtacca atcaagacgg cggtgtaa               888

SEQ ID NO: 77              moltype = DNA  length = 37
FEATURE                    Location/Qualifiers
misc_feature               1..37
                           note = Synthetic sequence
source                     1..37
                           mol_type = other DNA
                           organism = Synthetic construct
SEQUENCE: 77
tatatcatat ggctattagt atcgcgatca atgctgg                            37

SEQ ID NO: 78              moltype = DNA  length = 37
FEATURE                    Location/Qualifiers
misc_feature               1..37
```

-continued

```
                          note = Synthetic sequence
source                    1..37
                          mol_type = other DNA
                          organism = Synthetic construct
SEQUENCE: 78
ttggatcctt atgaactgat gcccggcctg gccgagg                          37

SEQ ID NO: 79            moltype = DNA   length = 42
FEATURE                  Location/Qualifiers
misc_feature             1..42
                          note = Synthetic sequence
source                    1..42
                          mol_type = other DNA
                          organism = Synthetic construct
SEQUENCE: 79
tatatcatat gatggctatt tcaattaata ttgttgcggg ac                    42

SEQ ID NO: 80            moltype = DNA   length = 39
FEATURE                  Location/Qualifiers
misc_feature             1..39
                          note = Synthetic sequence
source                    1..39
                          mol_type = other DNA
                          organism = Synthetic construct
SEQUENCE: 80
aaggatcctt acgaagcaac tctcttaaca tcaagtttg                        39

SEQ ID NO: 81            moltype = DNA   length = 16
FEATURE                  Location/Qualifiers
misc_feature             1..16
                          note = Synthetic sequence
source                    1..16
                          mol_type = other DNA
                          organism = Synthetic construct
SEQUENCE: 81
taccttgtta cgactt                                                 16

SEQ ID NO: 82            moltype = DNA   length = 20
FEATURE                  Location/Qualifiers
misc_feature             1..20
                          note = Synthetic sequence
misc_feature             12
                          note = "m" is an "a" or "c"
source                    1..20
                          mol_type = other DNA
                          organism = Synthetic construct
SEQUENCE: 82
agagtttgat cmtggctcag                                             20
```

INSECTICIDAL PROTEINS AND METHODS FOR THEIR USE

CROSS-REFERENCE TO RELATED APPLICATIONS

This application is a divisional application of U.S. patent application Ser. No. 17/283,042, filed Apr. 6, 2021, which is a national stage patent application of International patent application no. PCT/US2019/055409, filed Oct. 9, 2019, which claims the benefit of U.S. Provisional Application No. 62/743,784 filed on Oct. 10, 2018, the disclosures of each of which are incorporated herein by reference in their entireties.

REFERENCE TO SEQUENCE LISTING SUBMITTED ELECTRONICALLY

An XML formatted sequence listing having the file name "105990USDIV1_SequenceListingl.xml" created on Sep. 29, 2024, and having a size of 131,379 bytes is filed in computer readable form concurrently with the specification. The sequence listing contained in this XML formatted document is part of the specification and is herein incorporated by reference in its entirety.

FIELD

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants.

BACKGROUND

Biological control of insect pests of agricultural significance using a microbial agent, such as fungi, bacteria or another species of insect affords an environmentally friendly and a commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of *Bacillus thuringiensis*. These genetically engineered crops are now widely used in agriculture and have provided the farmer with an environmentally friendly alternative to traditional insect-control methods. While they have proven to be very successful commercially, these genetically engineered, insect-resistant crop plants provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with increased insecticidal activity, different spectrum of activity, and/or mode of action against insect pests, e.g., insecticidal proteins which are active against a variety of insects in the order Lepidoptera and the order Coleoptera including but not limited to insect pests that have developed resistance to existing insecticides.

SUMMARY

In one aspect, compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. Compositions also comprise transformed bacteria, plants, plant cells, tissues and seeds.

In another aspect, isolated or recombinant nucleic acid molecules are provided encoding IPD102 polypeptides including amino acid substitutions, deletions, insertions, and fragments thereof. Provided are isolated or recombinant nucleic acid molecules capable of encoding IPD102 polypeptides of SEQ ID NOs: 1-33 and 65-70, as well as amino acid substitutions, deletions, insertions, fragments thereof, and combinations thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In another aspect, IPD102 polypeptides are encompassed. Also provided are isolated or recombinant IPD102 polypeptides of SEQ ID NOs: 1-33 and 65-70, as well as amino acid substitutions, deletions, insertions, fragments thereof and combinations thereof.

In another aspect, methods are provided for producing the polypeptides and for using those polypeptides for controlling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional genes for insect resistance, for example, one or more additional genes for controlling Coleopteran, Lepidopteran, Hemipteran or nematode pests. The transgenic plant may further comprise any gene imparting an agronomic trait of interest.

In another aspect, methods for detecting the nucleic acids and polypeptides of the embodiments in a sample are also included. A kit for detecting the presence of an IPD102 polypeptide or detecting the presence of a polynucleotide encoding an IPD102 polypeptide in a sample is provided. The kit may be provided along with all reagents and control samples necessary for carrying out a method for detecting the intended agent, as well as instructions for use.

In another aspect, the compositions and methods of the embodiments are useful to produce organisms for the production of IPD102 polypeptides and transgenic plants with enhanced pest resistance or tolerance. These organisms and compositions comprising the organisms are desirable for agricultural purposes. The compositions of the embodiments are also useful for generating altered or improved proteins that have pesticidal activity or for detecting the presence of IPD102 polypeptides.

DETAILED DESCRIPTION

It is to be understood that this disclosure is not limited to the particular methodology, protocols, cell lines, genera, and reagents described, as such may vary. It is also to be understood that the terminology used herein is for describing particular embodiments only, and is not intended to limit the scope of the present disclosure.

The present disclosure is drawn to compositions and methods for controlling pests. The methods involve transforming organisms with nucleic acid sequences encoding IPD102 polypeptides. The nucleic acid sequences of the embodiments are useful for preparing plants and microorganisms that possess pesticidal activity. Thus, transformed bacteria, plants, plant cells, plant tissues and seeds are provided. The compositions include pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered IPD102 polypeptides by methods such as site directed mutagenesis, domain swapping or DNA shuffling. The IPD102 polypeptides find use in controlling or killing Lepidopteran, Coleopteran, Dipteran, fungal, Hemipteran and nematode pest populations and for producing compositions with pesticidal activity. Insect pests of interest include, but are not limited to, Coleoptera and Hemiptera species including but not limited to: *Diabrotica virgifera virgifera* LeConte (western corn rootworm); *D. barberi* Smith and Lawrence (northern corn rootworm); *D. undecimpunctata howardi* Barber (southern corn rootworm); and *Nezara viridula* Linnaeus (southern green stink bug).

Definitions

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this disclosure belongs unless clearly indicated otherwise.

By "pesticidal toxin" or "pesticidal protein" or "insecticidal protein" is used herein to refer to a toxin that has toxic activity against one or more pests, including, but not limited to, members of the Lepidoptera, Diptera, Hemiptera and Coleoptera orders or the Nematoda phylum or a protein with pesticidal activity that has sequence identity to such a protein.

"Sufficiently identical" is used herein to refer to an amino acid sequence that has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to a reference sequence using one of the alignment programs described herein using standard parameters.

As used herein, the term "protein," "peptide molecule," or "polypeptide" includes those molecules that undergo modification, including post-translational modifications, such as, but not limited to, disulfide bond formation, glycosylation, phosphorylation or oligomerization. Thus, as used herein, the terms "protein," "peptide molecule" or "polypeptide" includes any protein that is modified by any biological or non-biological process.

The terms "amino acid" and "amino acids" refer to all naturally occurring L-amino acids.

A "recombinant protein" is used herein to refer to a protein that is no longer in its natural environment, for example in vitro or in a recombinant bacterial or plant host cell. An IPD102 polypeptide that is substantially free of cellular material includes preparations of protein having less than about 30%, 20%, 10% or 5% (by dry weight) of other cellular proteins (also referred to herein as a "contaminating protein").

"Retains insecticidal activity" is used herein to refer to a polypeptide having at least about 10%, at least about 30%, at least about 50%, at least about 70%, 80%, 90%, 95% or higher of the insecticidal activity of the full-length IPD102 polypeptide.

"Fragments" or "biologically active portions" include polypeptide fragments comprising amino acid sequences sufficiently identical to an IPD102 polypeptide and having insecticidal activity and polynucleotides encoding the fragment. "Fragments" or "biologically active portions" of IPD102 polypeptides includes fragments comprising amino acid sequences sufficiently identical to the amino acid sequence set forth in IPD102 polypeptides of the disclosure, wherein the polypeptide has insecticidal activity.

An "isolated" nucleic acid molecule (or DNA) is used herein to refer to a nucleic acid sequence (or DNA) that is no longer in its natural environment by the hand of man, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes.

"Contiguous nucleotides" is used herein to refer to nucleotide residues that are immediately adjacent to one another.

As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments, the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a synthetic nucleic acid sequence.

"Retains insecticidal activity" is used herein to refer to a polypeptide having at least about 10%, at least about 30%, at least about 50%, at least about 70%, 80%, 90%, 95% or higher of the insecticidal activity of the full-length IPD102 polypeptide.

In some embodiments, the IPD102 polypeptide includes an amino acid sequence deduced from the full-length nucleic acid sequence disclosed herein and amino acid sequences that are shorter than the full-length sequences, either due to the use of an alternate downstream start site or due to processing that produces a shorter protein having pesticidal activity. Processing may occur in the organism the protein is expressed in or in the pest after ingestion of the protein.

Thus, provided herein are novel isolated or recombinant nucleic acid sequences that confer pesticidal activity. Also provided are the amino acid sequences of IPD102 polypeptides. The protein resulting from translation of these IPD102 genes allows cells to control or kill certain pests that ingest it.

IPD102 Proteins and Variants and Fragments Thereof

IPD102 polypeptides are encompassed by the disclosure. "IPD102 polypeptide" and "IPD102 protein" as used herein interchangeably refers to a polypeptide having insecticidal activity including but not limited to insecticidal activity against one or more insect pests, and is sufficiently identical to the IPD102 polypeptide of any one of SEQ ID NOs: 1-33 and 65-70. A variety of IPD102 polypeptides are contemplated. Sources of IPD102 polypeptides or related proteins include species selected from, but not limited to, the Genera *Pseudomonas, Methanosarcina, Echinicola, Sphingomonas, Granulicella, Chromatiaceae, Aquimarina, Nitrococcus, Yokenella, Dickeya, Enterobacter, Pectobacterium, Proteobacteria, Anaerobacillus,* and *Sodalis.*

In some embodiments, the IPD102 polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOs: 1-33 and 65-70, as well as amino acid substitutions, deletions, insertions, fragments thereof, and combinations thereof.

In some embodiments, the sequence identity is against the full-length sequence of an IPD102 polypeptide.

In another aspect IPD102 polypeptides are encompassed. Also provided are isolated or recombinant IPD102 polypeptides of SEQ ID NOs: 1-33 and 65-70. The term "about" when used herein in context with percent sequence identity means+/−0.5%. These values can be appropriately adjusted to determine corresponding homology of proteins considering amino acid similarity and the like.

In some embodiments, the sequence identity is calculated using ClustalW algorithm in the ALIGNX® module of the Vector NTI® Program Suite (Invitrogen Corporation, Carlsbad, Calif.) with all default parameters. In some embodiments, the sequence identity is across the entire length of polypeptide calculated using ClustalW algorithm in the ALIGNX® module of the Vector NTI® Program Suite (Invitrogen Corporation, Carlsbad, Calif.) with all default parameters.

In some embodiments fragments of IPD102 polypeptides comprise an amino acid sequence sufficiently identical to the amino acid sequence set forth in IPD102 polypeptides of the disclosure, wherein the polypeptide has insecticidal activity. Such biologically active portions can be prepared by recombinant techniques and evaluated for insecticidal activity. In some embodiments, the IPD102 polypeptide retains insecticidal activity against a Lepidopteran species. In some embodiments, the insecticidal activity is against one or more insect pests selected from *Diabrotica virgifera virgifera* LeConte (western corn rootworm); *D. barberi* Smith and Lawrence (northern corn rootworm); *D. undecimpunctata howardi* Barber (southern corn rootworm); and *Nezara viridula* Linnaeus (southern green stink bug).

In some embodiments, the polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more amino acids from the N-terminus and/or C-terminus, by proteolysis, by insertion of a start codon, by deletion of the codons encoding the deleted amino acids and concomitant insertion of a start codon, and/or insertion of a stop codon.

In some embodiments, the IPD102 polypeptide fragment is an N-terminal truncation of at least 1, 2, 3, 4, 5, 6, 7, 8, 9, 10, 11, 12, 13, 14, 15, 16, 17, 18, 19, 20, 21, 22, 23, 24 or more amino acids from the N-terminus of IPD102 polypeptides of SEQ ID NOs: 1-33 and 65-70.

In some embodiments, the IPD102 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids from the N-terminus and/or C-terminus relative to IPD102 polypeptides of SEQ ID NOs: 1-33 and 65-70.

In some embodiments, an IPD102 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of any one of the IPD102 polypeptides of SEQ ID NOs: 1-33 and 65-70, wherein the IPD102 polypeptide has insecticidal activity.

In some embodiments, an IPD102 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of any one of the IPD102 polypeptides of SEQ ID NOs: 1-33 and 65-70.

In some embodiments, an IPD102 polypeptide comprises an amino acid sequence of any one of SEQ ID NOs: 1-33 and 65-70 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or more amino acid substitutions, deletions and/or insertions compared to the native amino acid at the corresponding position of the respective IPD102 polypeptide of SEQ ID NOs: 1-33 and 65-70.

Amino acid sequence variants of an IPD102 polypeptide can be prepared by mutations in the DNA. This may also be accomplished by one of several forms of mutagenesis and/or in directed evolution.

In some aspects, the changes encoded in the amino acid sequence will not substantially affect the function of the protein. Such variants will possess the desired pesticidal activity. However, it is understood that the ability of an IPD102 polypeptide to confer pesticidal activity may be improved using such techniques upon the compositions of this disclosure.

Variants may be made by making random mutations or the variants may be designed. In the case of designed mutants, there is a high probability of generating variants with similar activity to the native toxin when amino acid identity is maintained in critical regions of the toxin which account for biological activity or are involved in the determination of three-dimensional configuration which ultimately is responsible for the biological activity. A high probability of retaining activity will also occur if substitutions are conservative. Amino acids may be placed in the following classes: nonpolar, uncharged polar, basic, and acidic. Conservative substitutions whereby an amino acid of one class is replaced with another amino acid of the same type are least likely to materially alter the biological activity of the variant. Table 1 provides a listing of examples of amino acids belonging to each class.

TABLE 1

| Classes of amino acids | |
| --- | --- |
| Class of Amino Acid | Examples of Amino Acids |
| Nonpolar Side Chains | Ala (A), Val (V), Leu (L), Ile (I), Pro (P), Met (M), Phe (F), Trp (W) |
| Uncharged Polar Side Chains | Gly (G), Ser (S), Thr (T), Cys (C), Tyr (Y), Asn (N), Gln (Q) |
| Acidic Side Chains | Asp (D), Glu (E) |
| Basic Side Chains | Lys (K), Arg (R), His (H) |
| Beta-branched Side Chains | Thr, Val, Ile |
| Aromatic Side Chains | Tyr, Phe, Trp, His |

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by inclusion of amino acid encoding sequences in the oligonucleotides utilized in the PCR amplification. Alternatively, the protein sequences added can include entire protein-coding sequences, to generate protein fusions. Such fusion proteins are often used to (1) increase expression of a protein of interest (2) introduce a binding domain, enzymatic activity or epitope to facilitate either protein purification, protein detection or other experimental uses (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different IPD102 polypeptide coding regions can be used to create a new IPD102 polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling include for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

Domain swapping or shuffling is another mechanism for generating altered IPD102 polypeptides. Domains may be swapped between IPD102 polypeptides resulting in hybrid or chimeric toxins with improved insecticidal activity or target spectrum. Methods for generating recombinant proteins and testing them for pesticidal activity are disclosed in, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266:17954-17958; Schnepf, et al., (1990) *J. Biol. Chem.* 265:20923-20930; Rang, et al., 91999) *Appl. Environ. Microbiol.* 65:2918-2925).

Phylogenetic, sequence motif, and structural analyses of insecticidal protein families. A sequence and structure analysis method can be employed, which is composed of four components: phylogenetic tree construction, protein sequence motifs finding, secondary structure prediction, and alignment of protein sequences and secondary structures. Details about each component are illustrated below.

Phylogenetic Tree Construction

The phylogenetic analysis can be performed using the software MEGA5. Protein sequences can be subjected to ClustalW version 2 analysis (Larkin M. A et al (2007) *Bioinformatics* 23(21): 2947-2948) for multiple sequence alignment. The evolutionary history is then inferred by the Maximum Likelihood method based on the JTT matrix-based model. The tree with the highest log likelihood is obtained, exported in Newick format, and further processed to extract the sequence IDs in the same order as they appeared in the tree. A few clades representing sub-families can be manually identified for each insecticidal protein family.

Protein Sequence Motifs Finding

Protein sequences are re-ordered according to the phylogenetic tree built previously, and fed to the MOTIF analysis tool MEME (Multiple EM for MOTIF Elicitation) (Bailey T. L., and Elkan C., *Proceedings of the Second International Conference on Intelligent Systems for Molecular Biology*, pp. 28-36, AAAI Press, Menlo Park, California, 1994.) for identification of key sequence motifs. MEME is setup as follows: Minimum number of sites 2, Minimum motif width 5, and Maximum number of motifs 30. Sequence motifs unique to each sub-family were identified by visual observation. The distribution of MOTIFs across the entire gene family could be visualized in HTML webpage. The MOTIFs are numbered relative to the ranking of the E-value for each MOTIF.

Secondary Structure Prediction

PSIPRED, top ranked secondary structure prediction method (Jones D T. (1999) *J. Mol. Biol.* 292: 195-202), can be used for protein secondary structure prediction. The tool provides accurate structure prediction using two feed-forward neural networks based on the PSI-BLAST output. The PSI-BLAST database is created by removing low-complexity, transmembrane, and coiled-coil regions in Uniref100. The PSIPRED results contain the predicted secondary structures (Alpha helix: H, Beta strand: E, and Coil: C) and the corresponding confidence scores for each amino acid in a given protein sequence.

Alignment of Protein Sequences and Secondary Structures

A script can be developed to generate gapped secondary structure alignment according to the multiple protein sequence alignment from step 1 for all proteins. All aligned protein sequences and structures are concatenated into a single FASTA file, and then imported into MEGA for visualization and identification of conserved structures.

In some embodiments, the IPD102 polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to, net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, IPD102 polypeptide having increased expression, increased solubility, decreased phytotoxicity, and digestibility of proteolytic fragments in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

In some embodiments, variants include polypeptides that differ in amino acid sequence due to mutagenesis. Variant proteins encompassed by the disclosure are biologically active, that is they continue to possess the desired biological activity (i.e. pesticidal activity) of the native protein. In some embodiment, the variant will have at least about 10%, at least about 30%, at least about 50%, at least about 70%, at least about 80% or more of the insecticidal activity of the native protein. In some embodiments, the variants may have improved activity over the native protein.

In some embodiments, the insecticidal activity is against a Coleopteran and/or Hemipteran species. In some embodiments, the insecticidal activity is against one or more insect pests selected from *Diabrotica virgifera virgifera* LeConte (western corn rootworm); *D. barberi* Smith and Lawrence (northern corn rootworm); *D. undecimpunctata howardi* Barber (southern corn rootworm); and *Nezara viridula* Linnaeus (southern green stink bug).

In some embodiments, the translation initiator methionine of the IPD102 polypeptide is cleaved off post translationally, for example by a methionine aminopeptidase in many cellular expression systems.

In some embodiments, the IPD102 polypeptide comprises the amino acid sequence of any one of SEQ ID NOs: 1-33 and 65-70.

In some embodiments, chimeric polypeptides are provided comprising regions of at least two different IPD102 polypeptides of the disclosure.

In some embodiments, chimeric polypeptides are provided comprising regions of at least two different IPD102 polypeptides selected from SEQ ID NO: 1 and SEQ ID NO: 11.

In some embodiments, chimeric IPD102 polypeptides are provided comprising an N-terminal Region of a first IPD102 polypeptide of the disclosure operably fused to a C-terminal Region of a second IPD102 polypeptide of the disclosure.

In other embodiments, the IPD102 polypeptide may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) J. Biol. Chem., 271:22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterfication reaction between the two termini to form a branched ester or thioester intermediate and peptide bond cleavage coupled to cyclization of the intein C-terminal asparagine to free the intein (Evans, et al., (2000) *J. Biol. Chem.*, 275:9091-9094. The IPD102 polypeptide may be encoded by two separate genes where the intein of the precursor protein comes from the two genes, referred to as a split-intein, and the two portions of the precursor are joined by a peptide bond formation.

In some embodiments, the IPD102 polypeptide is a circular permuted variant. In certain embodiments, the IPD102 polypeptide is a circular permuted variant of the polypeptide of SEQ ID NO: 1, or variant thereof having an amino acid substitution, deletion, addition or combinations thereof.

In another embodiment, fusion proteins are provided that include within its amino acid sequence an amino acid sequence comprising an IPD102 polypeptide or chimeric IPD102 polypeptide of the disclosure. Polynucleotides encoding an IPD102 polypeptide may be fused to signal sequences which will direct the localization of the IPD102 polypeptide to particular compartments of a prokaryotic or eukaryotic cell and/or direct the secretion of the IPD102 polypeptide of the embodiments from a prokaryotic or eukaryotic cell. For example, in *E. coli*, one may wish to direct the expression of the protein to the periplasmic space. Examples of signal sequences or proteins (or fragments thereof) to which the IPD102 polypeptide may be fused to direct the expression of the polypeptide to the periplasmic space of bacteria include, but are not limited to, the pe/B signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the IPD102 polypeptide may be fused to the pe/B pectate lyase signal sequence to increase the efficiency of expression and purification of such polypeptides in Gram-negative bacteria (see, U.S. Pat. Nos. 5,576,195 and 5,846,818). The fusion protein may be a plant plastid transit peptide/polypeptide fusions or an Apoplast transit peptides such as rice or barley alpha-amylase secretion signal. The plastid transit peptide is generally fused N-terminal to the polypeptide to be targeted (e.g., the fusion partner). In one embodiment, the fusion protein consists essentially of the plastid transit peptide and the IPD102 polypeptide to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide if the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, because of specific intercellular conditions or the combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept "in frame" to allow the synthesis of the desired fusion protein. In some cases, it may be preferable to remove the initiator methionine of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity if the transit peptide cleavage site remains accessible and the function of the second protein is not altered by the addition of these extra amino acids at its N-terminus. Precise cleavage site between the transit peptide and the second protein (with or without its initiator methionine) can be created using gene synthesis (Stemmer, et al., (1995) *Gene* 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) *J. Biol. Chem.* 263(29):15104-9. In some embodiments, the IPD102 polypeptide is fused to a heterologous signal peptide or heterologous transit peptide.

In some embodiments, fusion proteins are provide comprising an IPD102 polypeptide or chimeric IPD102 polypeptide of the disclosure represented by a formula selected from the group consisting of:

$$R^1\text{-}L\text{-}R^2, R^2\text{-}L\text{-}R^1, R^1\text{-}R^2 \text{ or } R^2\text{-}R^1$$

wherein $R^1$ is an IPD102 polypeptide or chimeric IPD102 polypeptide of the disclosure and $R^2$ is a protein of interest. In some embodiments, $R^1$ and $R^2$ are an IPD102 polypeptide or chimeric IPD102 polypeptide of the disclosure. The $R^1$ polypeptide is fused either directly or through a linker (L) segment to the $R^2$ polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

One example of a highly-flexible linker is the (GlySer)-rich spacer region present within the pIII protein of the filamentous bacteriophages, e.g. bacteriophages M13 or fd (Schaller, et al., 1975). This region provides a long, flexible spacer region between two domains of the pIII surface protein. Also included are linkers in which an endopeptidase recognition sequence is included. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Linkers of the present disclosure include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

Nucleic Acid Molecules, and Variants and Fragments Thereof

Isolated or recombinant nucleic acid molecules comprising nucleic acid sequences encoding IPD102 polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

In some embodiments, an isolated nucleic acid molecule encoding IPD102 polypeptides has one or more change in the nucleic acid sequence compared to the native or genomic nucleic acid sequence. In some embodiments, the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; deletion of one or more upstream or downstream regulatory regions; and deletion of the 5' and/or 3' untranslated region associated with the genomic nucleic acid sequence. In some embodiments, the nucleic acid molecule encoding an IPD102 polypeptide is a non-genomic sequence.

A variety of polynucleotides that encode IPD102 polypeptides or related proteins are contemplated. Such polynucleotides are useful for production of IPD102 polypeptides in host cells when operably linked to a suitable promoter, transcription termination and/or polyadenylation sequences. Such polynucleotides are also useful as probes for isolating homologous or substantially homologous polynucleotides that encode IPD102 polypeptides or related proteins.

Methods for Engineering IPD102 Polypeptides

Methods for engineering IPD102 polypeptides are also encompassed by the disclosure. In some embodiments, the method for engineering IPD102 polypeptides uses rational protein design based on a secondary, tertiary or quaternary structure model of the IPD102 polypeptide. In silico modeling tools can be used in the methods of the disclosure. In some embodiments, the rational protein design uses an in-silico modeling tool selected from, but not limited to, PyMOL (PyMOL Molecular Graphics System, Version 1.7.4 Schrödinger, LLC.), Maestro©, BioLuminate (Zhu, K.; et al., Proteins, 2014, 82(8), 1646-1655; Salam, N. K et al., Protein Eng. Des. Sel., 2014, 27(10), 365-74; Beard, H. et al. PLoS ONE, 2013, 8(12), e82849), MOE© (Molecular Operating Environment (MOE), 2013.08; Chemical Computing Group Inc., 1010 Sherbooke St. West, Suite #910, Montreal, QC, Canada, H3A 2R7, 2015), Jmol, and Discovery Studio© (Accelrys Software Inc. Discovery Studio Modeling Environment, Release 3.5.0, San Diego: Accelrys Software Inc. 2013). In some embodiments, the modeling uses Discovery Studio© software. In some embodiments, the method the structural coordinates can be determined by homology modeling. In some embodiments of the method, the structural coordinates can be determined by X-ray crystallography or solution NMR.

In some embodiments, the IPD102 polypeptide is engineered by the method of the disclosure to have a modified physical property compared to the native IPD102 polypeptide. In some embodiments, the modified physical properties include, but are not limited to net surface charge and charge distribution on the protein surface, net hydrophobicity and hydrophobic residue distribution on the protein surface, surface charge density, surface hydrophobicity density, total count of surface ionizable groups, and protein size. In some embodiments, the modified physical in-properties include, but are not limited to solubility, folding, stability, protease stability, digestibility, planta expression, insecticidal potency, spectrum of insecticidal activity, ion channel activity of protomer pore, and receptor binding. In some embodiments, the modified physical property is improved protease stability, improved in-planta expression, improved solubility, improved potency, improved ion-channel activity of protomer pore, and/or improved receptor binding.

Using the methods of the disclosure, proteolytically-sensitive sites can be identified and may be modified or utilized to produce more stable or more biologically active IPD102 polypeptides.

Using methods of the disclosure, sites involved in receptor binding and/or pore formation can be identified and may be modified to create IPD102 polypeptides having enhanced insecticidal activity; enhanced ability to form channels; and reduced size.

Using methods of the disclosure, occupation of a site by a water molecule can be identified and can be modified to create IPD102 molecules having modified flexibility in a region or increasing the number of hydrophobic residues along that surface, which may be involved in receptor binding and/or pore formation.

Using methods of the disclosure, hydrogen bonding in a region can be identified and the amino acids may be substituted to modify the number of hydrogen bonds, including salt bridges, to create IPD102 polypeptides having a modified hydrophobic interaction surface facilitating pre-pore and pore formation and/or modified insecticidal activity.

Using methods of the disclosure, loop regions can be identified and may be modified to create IPD102 polypeptides having modified channel or pore formation, folding, and/or receptor binding.

Using methods of the disclosure, complex electrostatic surfaces and hydrophobic or hydrophilic interactions can be identified and modified to create IPD102 polypeptides having modified receptor interaction Using methods of the disclosure, metal binding sites can be identified and modified to create IPD102 polypeptides having modified ion channel or pore activity.

Using methods of the disclosure, amino acids that may be buried or otherwise removed from the surface of the protein that hold in place the three-dimensional structure can be identified and modified to create IPD102 polypeptides having modified stability or flexibility.

Using methods of the disclosure, non-specific binding sites to other biomolecules can be identified and modified to create IPD102 polypeptides having modified receptor binding to the specific receptor and enhanced toxicity.

Applying various computational tools coupled with the understanding of saturated mutagenesis and the structural/functional relationship for IPD102 polypeptides as disclosed herein, various physical properties of IPD102 polypeptides can be identified and modified for the better overall performance as an insecticidal protein against the desired targets. Combinatory mutagenesis at various regions can enhance specificity to the current active targets and potentially can also change activity spectrum against different targets. Such targeted combinatorial mutagenesis can be achieved with incorporation of mutagenic oligo nucleotides or generated by gene synthesis or the combination of both approaches. Mutagenesis on defined loop regions can also enhance physical properties of IPD102 polypeptides such as increasing protein stability by reducing protease degradation ability and increasing thermostability etc. In additional, combinatorial mutagenesis can be applied to the amino acid residues involved in hydrophobic interface surface. Enhancement of hydrophobic interface surface can potentially increase insecticidal activity, thermostability and other physical properties. Additional improvements can also be achieved through mutagenesis of other part of the molecule such as various beta-sheets and alpha helices to increase stability and activity.

Polynucleotides Encoding IPD102 Polypeptides

One source of polynucleotides that encode IPD102 polypeptides or related proteins is a species selected from, but not limited to, *Pseudomonas, Methanosarcina, Echinicola, Sphingomonas, Granulicella, Chromatiaceae, Aquimarina,* Nitrococcus, Yokenella, Dickeya, *Enterobacter, Pectobacterium, Proteobacteria, Anaerobacillus,* or *Sodalis species,*

*which contains an IPD*102 polynucleotide of any one of SEQ ID NOs: 34-64, encoding certain IPD102 polypeptides of SEQ ID NOs: 1-33.

The polynucleotides of SEQ ID NOs: 34-64 and 71-76 can be used to express IPD102 polypeptides in recombinant bacterial hosts that include but are not limited to *Agrobacterium, Bacillus, Escherichia, Salmonella, Pseudomonas* and *Rhizobium* bacterial host cells. The polynucleotides are also useful as probes for isolating homologous or substantially homologous polynucleotides that encode IPD102 polypeptides or related proteins. Such probes can be used to identify homologous or substantially homologous polynucleotides derived from species selected from, but not limited to, *Pseudomonas, Methanosarcina, Echinicola, Sphingomonas, Granulicella, Chromatiaceae, Aquimarina, Nitrococcus, Yokenella, Dickeya, Enterobacter, Pectobacterium*, Proteobacteria, Anaerobacillus, and Sodalis.

Polynucleotides that encode IPD102 polypeptides can also be synthesized de novo from an IPD102 polypeptide sequence. The sequence of the polynucleotide gene can be deduced from an IPD102 polypeptide sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide. Examples of IPD102 polypeptide sequences that can be used to obtain corresponding nucleotide encoding sequences include, but are not limited to the IPD102 polypeptides of SEQ ID NOs: 1-33 and 65-70. Furthermore, synthetic IPD102 polynucleotide sequences of the disclosure can be designed so that they will be expressed in plants.

In some embodiments, the nucleic acid molecule encoding an IPD102 polypeptide is a polynucleotide having the sequence set forth in one of SEQ ID NOs: 34-64 and 71-76, and variants, fragments and complements thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

"Complement" is used herein to refer to a nucleic acid sequence that is complementary to a given nucleic acid sequence such that it can hybridize to the given nucleic acid sequence to thereby form a stable duplex. In some embodiments, the nucleic acid sequence is fully complementary. "Polynucleotide sequence variants" is used herein to refer to a nucleic acid sequence that except for the degeneracy of the genetic code encodes the same polypeptide.

In some embodiments, the nucleic acid molecule encoding the IPD102 polypeptide is a non-genomic nucleic acid sequence.

In some embodiments, the nucleic acid molecule encoding an IPD102 polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to any one of the nucleic acid sequences of SEQ ID NOs: 34-64 and 71-76, wherein the encoded IPD102 polypeptide has insecticidal activity.

In some embodiments, the IPD102 polynucleotide encodes an IPD102 polypeptide having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOs: 1-33 and 65-70, and has at least one amino acid substitution, deletion, insertion or combination therefore, compared to the native sequence.

In some embodiments, the nucleic acid molecule encodes an IPD102 polypeptide comprising an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of any one of the amino acid sequences of SEQ ID NOs: 1-33 and 65-70.

In some embodiments, the nucleic acid molecule encodes an IPD102 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of any one of the amino acid sequences of SEQ ID NOs: 1-33 and 65-70.

In some embodiments, the nucleic acid molecule encodes an IPD102 polypeptide comprising an amino acid sequence of any one of SEQ ID NOs: 1-33 and 65-70 having 1, 2, 3, 4, 5, 6, 7, 8, 9, 1011, 12, 13, 14, 15, 16, 17, 18, 19, 20, 21, 22, 23, 24, 25, 26, 27, 28, 29, 30, 31, 32, 33, 34, 35 or more amino acid substitutions, deletions and/or insertions compared to the amino acid at the corresponding position of the respective SEQ ID NO: 1-33 and 65-70.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

The polynucleotide coding sequence can be modified to add a codon at the position following the methionine start codon to create a restriction enzyme site for recombinant cloning purposes and/or for expression purposes. In some embodiments, the IPD102 polypeptide further comprises an alanine residue at the position after the translation initiator methionine.

Also provided are nucleic acid molecules that encode transcription and/or translation products that are subsequently spliced to ultimately produce functional IPD102 polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an IPD102 polypeptide encoding sequence. An example of trans-splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365, 377 and 6,531,316). Thus, in some embodiments, the poly-nucleotides do not directly encode a full-length IPD102 polypeptide, but rather encode a fragment or fragments of an IPD102 polypeptide. These polynucleotides can be used to express a functional IPD102 polypeptide through a mecha-nism involving splicing, where splicing can occur at the level of polynucleotide (e.g., intron/exon) and/or polypep-tide (e.g., intein/extein). This can be useful, for example, in controlling expression of pesticidal activity, since a func-tional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding IPD102 polypeptides are also encompassed by the embodiments. A fragment of a nucleic acid sequence may encode a biologically active portion of an IPD102 polypeptide or it may be a fragment that can be used as a hybridization probe or PCR primer using methods disclosed below. Nucleic acid molecules that are fragments of a nucleic acid sequence that are contiguous or up to the number of nucleotides present in a full-length nucleic acid sequence disclosed herein, depending upon the intended use. Fragments of the nucleic acid sequences of the embodiments will encode protein fragments that retain the biological activity of the IPD102 polypeptide and, hence, retain insec-ticidal activity. In some embodiments, the IPD102 polypep-tide retains at least about 10%, at least about 30%, at least about 50%, at least about 70%, 80%, 90%, 95% or higher of the insecticidal activity of the full-length IPD102 polypep-tide. In some embodiments, the insecticidal activity is against a Coleopteran and/or Hemipteran species. In some embodiments, the insecticidal activity is against one or more insect pests selected from *Diabrotica virgifera virgifera* LeConte (western corn rootworm); *D. barberi* Smith and Lawrence (northern corn rootworm); *D. undecimpunctata howardi* Barber (southern corn rootworm); and *Nezara viridula* Linnaeus (southern green stink bug).

In some embodiments, the IPD102 polypeptide is encoded by a nucleic acid sequence sufficiently identical to the nucleic acid sequence of any one of SEQ ID NOs: 34-64 and 71-76. "Sufficiently homologous" is used herein to refer to an amino acid or nucleic acid sequence that has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. These values can be appropriately adjusted to determine corresponding homology of proteins encoded by two nucleic acid sequences by considering degeneracy, amino acid similarity, reading frame positioning, and the like. In some embodiments, the sequence homology is against the full-length sequence of the polynucleotide encoding an IPD102 polypeptide or against the full-length sequence of an IPD102 polypeptide.

In some embodiments, the nucleic acid encodes an IPD102 polypeptide having at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOs: 1-33 and 65-70.

To determine the percent identity of two or more amino acid sequences or of two or more nucleic acid sequences, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence (e.g., across the entirety of a sequence of the disclosure). The percent identity between two sequences can be determined using techniques similar to those described below, with or without allowing gaps. In calculating percent identity, typically exact matches are counted.

Another non-limiting example of a mathematical algo-rithm utilized for the comparison of sequences is the algo-rithm of Needleman and Wunsch, (1970) J. Mol. Biol. 48(3):443-453, used GAP Version 10 software to determine sequence identity or similarity using the following default parameters: % identity and % similarity for a nucleic acid sequence using GAP Weight of 50 and Length Weight of 3, and the nwsgapdna.cmpii scoring matrix; % identity or % similarity for an amino acid sequence using GAP weight of 8 and length weight of 2, and the BLOSUM62 scoring program. Equivalent programs may also be used. "Equiva-lent program" is used herein to refer to any sequence comparison program that, for any two sequences in question, generates an alignment having identical nucleotide residue matches and an identical percent sequence identity when compared to the corresponding alignment generated by GAP Version 10.

In some embodiments, the IPD102 polynucleotide encodes an IPD102 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of any one of the amino acid sequences of SEQ ID NOs: 1-33 and 65-70.

In some embodiments, polynucleotides are provided encoding chimeric polypeptides comprising regions of at least two different IPD102 polypeptides of the disclosure.

In some embodiments, polynucleotides are provided encoding chimeric polypeptides comprising regions of at least two different IPD102 polypeptides selected from SEQ ID NOs: 1-33 and 65-70.

In some embodiments, polynucleotides are provided encoding chimeric polypeptides comprising an N-terminal Region of a first IPD102 polypeptide of the disclosure operably fused to a C-terminal Region of a second IPD102 polypeptide of the disclosure.

In some embodiments, polynucleotides are provided encoding chimeric polypeptides comprising an N-terminal Region of a first IPD102 polypeptide operably fused to a C-terminal Region of a second IPD102 polypeptide, where the IPD102 polypeptide is selected from SEQ ID NOs: 1-33 and 65-70.

In some embodiments, an IPD102 polynucleotide encodes the IPD102 polypeptide comprising an amino acid sequence of any one of SEQ ID NOs: 1-33 and 65-70.

The embodiments also encompass nucleic acid molecules encoding IPD102 polypeptide variants. "Variants" of the IPD102 polypeptide encoding nucleic acid sequences include those sequences that encode the IPD102 polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the IPD102 polypeptides disclosed as discussed below.

The present disclosure provides isolated or recombinant polynucleotides that encode any of the IPD102 polypeptides disclosed herein. Due to the degeneracy of the genetic code, a multitude of nucleotide sequences encoding IPD102 polypeptides of the present disclosure exist.

Changes can be introduced by mutation of the nucleic acid sequences thereby leading to changes in the amino acid sequence of the encoded IPD102 polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known, including those developed by the inventors and their co-workers. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made during the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-319; Gates, et al., (1996) *J Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene,* 164:49-53; Stemmer, (1995) *Science* 270: 1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortle, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology* (Eckstein and Lilley, eds., Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); Zoller and Smith, (1982)

21

*Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); Nakamaye and Eckstein, (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA,* 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following US patents, PCT Publications and Applications and EPO publications: U.S. Pat. Nos. 5,723,323, 5,763,192, 5,814,476, 5,817,483, 5,824,514, 5,976,862, 5,605,793, 5,811,238, 5,830,721, 5,834,252, 5,837,458, WO 1995/22625, WO 1996/33207, WO 1997/20078, WO 1997/35966, WO 1999/41402, WO 1999/41383, WO 1999/41369, WO 1999/41368, EP 752008, EP 0932670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, WO 2001/23401 and PCT/US01/06775.

The nucleotide sequences of the embodiments can also be used to isolate corresponding sequences from a *Pseudomonas, Methanosarcina, Echinicola, Sphingomonas, Granulicella, Chromatiaceae, Aquimarina, Nitrococcus, Yokenella, Dickeya, Enterobacter, Pectobacterium, Proteobacteria, Anaerobacillus, or Sodalis* species. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are disclosed in Sambrook, et al., (1989) *Molecular Cloning: A Laboratory Manual* (2d ed., Cold Spring Harbor Laboratory Press, Plainview, New York), hereinafter "Sambrook". See also, Innis, et al., eds. (1990) *PCR Protocols: A Guide to Methods and Applications* (Academic Press, New York); Innis and Gelfand, eds. (1995) PCR Strategies (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

To identify potential IPD102 polypeptides from *Pseudomonas, Methanosarcina, Echinicola, Sphingomonas, Granulicella, Chromatiaceae, Aquimarina, Nitrococcus, Yokenella, Dickeya, Enterobacter, Pectobacterium, Proteobacteria, Anaerobacillus,* or *Sodalis,* the *Pseudomonas, Methanosarcina, Echinicola, Sphingomonas, Granulicella, Chromatiaceae, Aquimarina, Nitrococcus, Yokenella, Dickeya, Enterobacter, Pectobacterium, Proteobacteria, Anaerobacillus,* or *Sodalis* cell lysates can be screened with antibodies generated against an IPD102 polypeptides and/or IPD102 polypeptides using Western blotting and/or ELISA methods. This type of assays can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of IPD102 polypeptides using protocols in the literatures (Scott Patterson, (1998), 10.22, 1-24, Current Protocol in Molecular Biology published by John Wiley & Son Inc). Specifically, LC-MS/MS based protein identification method is used to associate the MS data of given cell lysate or desired molecular weight enriched samples (excised from SDS-PAGE gel of relevant molecular weight bands to IPD102 polypeptides) with sequence information of SEQ ID NOs: 1-33, and their homologs. Any match in peptide sequences indicates the potential of having the homologous proteins in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known IPD102 polypeptide-encoding nucleic acid sequence disclosed herein. Degenerate primers designed based on conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequence encoding an IPD102 polypeptide of the disclosure or a fragment or variant thereof. Methods for the preparation of probes for hybridization are disclosed in Sambrook and Russell, (2001), supra, herein incorporated by reference.

For example, an entire nucleic acid sequence, encoding an IPD102 polypeptide, disclosed herein or one or more portions thereof may be used as a probe capable of specifically hybridizing to corresponding nucleic acid sequences encoding IPD102 polypeptide-like sequences and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) Molecular Cloning: A Laboratory Manual (2d ed., Cold Spring Harbor Laboratory Press, Cold Spring Harbor, N.Y.).

Hybridization of such sequences may be carried out under stringent conditions. "Stringent conditions" or "stringent hybridization conditions" is used herein to refer to conditions under which a probe will hybridize to its target sequence to a detectably greater degree than to other sequences (e.g., at least 2-fold over background). Preferably, hybridization is conducted under stringent conditions by techniques well-known in the art, as described, for example, in Keller and Manak (1993). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

$T_m$ (in ° C.) may be experimentally determined or may be approximated by calculation. For DNA-DNA hybrids, the $T_m$ can be approximated from the equation of Meinkoth and Wahl (1984): $T_m$(° C.)=81.5° C.+16.6(log M)+0.41(% GC)−0.61(% formamide)−500/L; where M is the molarity of monovalent cations, % GC is the percentage of guanosine and cytosine nucleotides in the DNA, % formamide is the percentage of formamide in the hybridization solution, and L is the length of the hybrid in base pairs. Alternatively, the $T_m$ is described by the following formula (Beltz et al., 1983): $T_m$(° C.)=81.5° C.+16.6(log[Na+])+0.41(% GC)−0.61(% formamide)−600/L where [Na+] is the molarity of sodium ions, % GC is the percentage of guanosine and cytosine nucleotides in the DNA, % formamide is the percentage of formamide in the hybridization solution, and L is the length of the hybrid in base pairs.

Compositions

Compositions comprising at least one IPD102 polypeptide or IPD102 chimeric polypeptide of the disclosure are also embraced.

Antibodies

Antibodies to an IPD102 polypeptide of the embodiments or to variants or fragments thereof are also encompassed. The antibodies of the disclosure include polyclonal and monoclonal antibodies as well as fragments thereof which retain their ability to bind to an IPD102 polypeptide found in the insect gut. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and $F(ab)_2$ fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. Antibodies against IPD102 polypeptides or antigen-binding portions thereof can be produced by a variety of techniques, including conventional monoclonal antibody methodology, for example the standard somatic cell hybridization technique of Kohler and Milstein, (1975) *Nature* 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing an IPD102 polypeptide as antigens.

A kit for detecting the presence of an IPD102 polypeptide or detecting the presence of a nucleotide sequence encoding an IPD102 polypeptide in a sample is provided. In one embodiment, the kit provides antibody-based reagents for detecting the presence of an IPD102 polypeptide in a tissue sample. In another embodiment, the kit provides labeled nucleic acid probes useful for detecting the presence of one or more polynucleotides encoding an IPD102 polypeptide. The kit is provided along with appropriate reagents and controls for carrying out a detection method, as well as instructions for use of the kit.

Receptor Identification and Isolation

Receptors to the IPD102 polypeptide of the embodiments or to variants or fragments thereof are also encompassed. Methods for identifying receptors can be found in Hofmann, et. al., (1988) *Eur. J. Biochem.* 173:85-91; and Gill, et al., (1995) *J. Biol. Chem.* 27277-27282) and can be employed to identify and isolate the receptor that recognizes the IPD102 polypeptide using the brush-border membrane vesicles from susceptible insects. In addition to the radioactive labeling method listed in the cited literatures, an IPD102 polypeptide can be labeled with fluorescent dye and other common labels such as streptavidin. Brush-border membrane vesicles (BBMV) of susceptible insects such as soybean looper and stink bugs can be prepared according to the protocols listed in the references and separated on SDS-PAGE gel and blotted on suitable membrane. Labeled IPD102 polypeptide can be incubated with blotted membrane of BBMV and labeled IPD102 polypeptide can be identified with the labeled reporters. Identification of protein band(s) that interact with the IPD102 polypeptide can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the IPD102 polypeptide. Receptor function for insecticidal activity by the IPD102 polypeptide can be verified by RNAi type of gene knock out method (Rajagopal, et al., (2002) *J. Biol. Chem.* 277:46849-46851).

Nucleotide Constructs, Expression Cassettes and Vectors

The use of the term "nucleotide constructs" herein is not intended to limit the embodiments to nucleotide constructs comprising DNA. Nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the IPD102 polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments, the DNA construct comprises a polynucleotide encoding an IPD102 polypeptide of the embodiments.

In some embodiments, the DNA construct comprises a polynucleotide encoding a chimeric IPD102 polypeptide of the embodiments.

In some embodiments, the DNA construct comprises a polynucleotide encoding a fusion protein comprising an IPD102 polypeptide of the embodiments.

In some embodiments, the DNA construct comprises a polynucleotide comprising a first coding sequence encoding the N-terminal Region of a first IPD102 polypeptide of the disclosure and a second coding sequence encoding the C-terminal Region of a second IPD102 polypeptide of the disclosure.

In some embodiments, the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers including, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used, each of which is incorporated by reference. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proud-foot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modi-fied to account for the specific preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize usage for 28 genes from maize plants is listed in Table 4 of Murray, et al., supra. Methods for synthesizing plant-preferred genescan be found in Murray, et al., (1989) *Nucleic Acids Res.* 17:477-498, and Liu H et al. *Mol Bio Rep* 37:677-684, 2010, herein incorporated by reference. A *Zea maize* usage table can be also found at kazusa.or.jp//cgi-bin/show.cgi?species=4577, which can be accessed using the www prefix.

A *Glycine max* usage table can be found at kazusa.or.jp//cgi-bin/show.cgi?species=3847&aa=1&style=N, which can be accessed using the www prefix.

In some embodiments, the recombinant nucleic acid mol-ecule encoding an IPD102 polypeptide has maize optimized codons.

Additional sequence modifications are known to enhance gene expression in a cellular host. These include elimination of sequences encoding spurious polyadenylation signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expres-sion vector is intended. Host cells may be prokaryotic cells such as *E. coli* or eukaryotic cells such as yeast, insect, amphibian or mammalian cells or monocotyledonous or dicotyledonous plant cells. An example of a monocotyle-donous host cell is a maize host cell. When possible, the sequence is modified to avoid predicted hairpin secondary mRNA structures.

The expression cassettes may additionally contain 5' leader sequences. Such leader sequences can act to enhance translation. Translation leaders include: picornavirus lead-ers, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-

385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) *Methods Enzymol.* 153:507-516). In some embodiments, the signal sequence is in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids includ-ing chloroplasts, mitochondria, and the like. Nuclear-en-coded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the informa-tion for targeting to the lumen. Recent research in pro-teomics of the higher plant chloroplast has achieved in the identification of numerous nuclear-encoded lumen proteins (Kieselbach et al. *FEBS LETT* 480:271-276, 2000; Peltier et al. Plant Cell 12:319-341, 2000; Bricker et al. *Biochim. Biophys Acta* 1503:350-356, 2001), the lumen targeting signal peptide of which can potentially be used in accor-dance with the present disclosure. About 80 proteins from *Arabidopsis*, as well as homologous proteins from spinach and garden pea, are reported by Kieselbach et al., *Photo-synthesis Research,* 78:249-264, 2003. Table 2 of this pub-lication, which is incorporated into the description herewith by reference, discloses 85 proteins from the chloroplast lumen, identified by their accession number (see also US Patent Application Publication 2009/09044298). In addition, the recently published draft version of the rice genome (Goff et al, *Science* 296:92-100, 2002) is a suitable source for lumen targeting signal peptide which may be used in accor-dance with the present disclosure.

Suitable chloroplast transit peptides (CTP) include chi-meric CT's comprising but not limited to, an N-terminal domain, a central domain or a C-terminal domain from a CTP from *Oryza sativa* 1-decoy-D xylose-5-Phosphate Syn-thase *Oryza sativa*-Superoxide dismutase *Oryza sativa*-soluble starch synthase *Oryza sativa*-NADP-dependent Malic acid enzyme *Oryza sativa*-Phospho-2-dehydro-3-de-oxyheptonate Aldolase 2 *Oryza sativa*-L-Ascorbate peroxi-dase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type US Patent Application Publication 2012/0304336).

The IPD102 polypeptide gene to be targeted to the chlo-roplast may be optimized for expression in the chloroplast to account for differences in usage between the plant nucleus and this organelle. In this manner, the nucleic acids of interest may be synthesized using chloroplast-preferred sequences.

In preparing the expression cassette, the various DNA fragments may be manipulated to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

Several promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) Nature 313:810-812); rice actin (McElroy, et al., (1990) Plant Cell 2:163-171); ubiquitin (Christensen, et al., (1989) Plant Mol. Biol. 12:619-632 and Christensen, et al., (1992) Plant Mol. Biol. 18:675-689); pEMU (Last, et al., (1991) Theor. Appl. Genet. 81:581-588); MAS (Velten, et al., (1984) EMBO J. 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) Ann. Rev. Phytopath. 28:425-449; Duan, et al., (1996) Nature Biotechnology 14:494-498); wun1 and wun2, U.S. Pat. No. 5,428,148; win1 and win2 (Stanford, et al., (1989) Mol. Gen. Genet. 215:200-208); systemin (McGurl, et al., (1992) Science 225:1570-1573); WIP1 (Rohmeier, et al., (1993) Plant Mol. Biol. 22:783-792; Eckelkamp, et al., (1993) FEBS Letters 323:73-76); MPI gene (Corderok, et al., (1994) Plant J. 6(2):141-150) and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) Neth. J. Plant Pathol. 89:245-254; Uknes, et al., (1992) Plant Cell 4: 645-656 and Van Loon, (1985) Plant Mol. Virol. 4:111-116. See also, WO 1999/43819, herein incorporated by reference.

Of interest are promoters that are expressed locally at or near the site of pathogen infection. See, for example, Marineau, et al., (1987) Plant Mol. Biol. 9:335-342; Matton, et al., (1989) Molecular Plant-Microbe Interactions 2:325-331; Somsisch, et al., (1986) Proc. Natl. Acad. Sci. USA 83:2427-2430; Somsisch, et al., (1988) Mol. Gen. Genet. 2:93-98 and Yang, (1996) Proc. Natl. Acad. Sci. USA 93:14972-14977. See also, Chen, et al., (1996) Plant J. 10:955-966; Zhang, et al., (1994) Proc. Natl. Acad. Sci. USA 91:2507-2511; Warner, et al., (1993) Plant J. 3:191-201; Siebertz, et al., (1989) Plant Cell 1:961-968; U.S. Pat. No. 5,750,386 (nematode-inducible) and the references cited therein. Of particular interest is the inducible promoter for the maize PRms gene, whose expression is induced by the pathogen Fusarium moniliforme (see, for example, Cordero, et al., (1992) Physiol. Mol. Plant Path. 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters include but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) Proc. Natl. Acad. Sci. USA 88:10421-10425 and McNellis, et al., (1998) Plant J. 14(2): 247-257) and tetracycline-inducible and tetracycline-repressible promoters (see, for example, Gatz, et al., (1991) Mol. Gen. Genet. 227:229-237 and U.S. Pat. Nos. 5,814,618 and 5,789,156), herein incorporated by reference.

Tissue-preferred promoters can be utilized to target enhanced an IPD102 polypeptide expression within a particular plant tissue. Tissue-preferred promoters include those discussed in Yamamoto, et al., (1997) Plant J. 12(2)255-265; Kawamata, et al., (1997) Plant Cell Physiol. 38(7): 792-803; Hansen, et al., (1997) Mol. Gen Genet. 254(3): 337-343; Russell, et al., (1997) Transgenic Res. 6(2):157-168; Rinehart, et al., (1996) Plant Physiol. 112(3):1331-1341; Van Camp, et al., (1996) Plant Physiol. 112(2):525-535; Canevascini, et al., (1996) Plant Physiol. 112(2):513-524; Yamamoto, et al., (1994) Plant Cell Physiol. 35(5): 773-778; Lam, (1994) Results Probl. Cell Differ. 20:181-196; Orozco, et al., (1993) Plant Mol Biol. 23(6):1129-1138; Matsuoka, et al., (1993) Proc Natl. Acad. Sci. USA 90(20): 9586-9590 and Guevara-Garcia, et al., (1993) Plant J. 4(3):495-505. Such promoters can be modified, if necessary, for weak expression.

Leaf-preferred promoters can be found in Yamamoto, et al., (1997) Plant J. 12(2):255-265; Kwon, et al., (1994) Plant Physiol. 105:357-67; Yamamoto, et al., (1994) Plant Cell Physiol. 35(5):773-778; Gotor, et al., (1993) Plant J. 3:509-18; Orozco, et al., (1993) Plant Mol. Biol. 23(6):1129-1138 and Matsuoka, et al., (1993) Proc. Natl. Acad. Sci. USA 90(20):9586-9590.

Root-preferred or root-specific promoters are known and can be selected from the many available from the literature or isolated de novo from various compatible species. See, for example, Hire, et al., (1992) Plant Mol. Biol. 20(2):207-218 (soybean root-specific glutamine synthetase gene); Keller and Baumgartner, (1991) Plant Cell 3(10):1051-1061 (root-specific control element in the GRP 1.8 gene of French bean); Sanger, et al., (1990) Plant Mol. Biol. 14(3):433-443 (root-specific promoter of the mannopine synthase (MAS) gene of Agrobacterium tumefaciens) and Miao, et al., (1991) Plant Cell 3(1):11-22 (full-length cDNA clone encoding cytosolic glutamine synthetase (GS), which is expressed in roots and root nodules of soybean). See also, Bogusz, et al., (1990) Plant Cell 2(7):633-641, where two root-specific promoters isolated from hemoglobin genes from the nitrogen-fixing nonlegume Parasponia andersonii and the related non-nitrogen-fixing nonlegume Trema tomentosa are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, Plant Science (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2 gene is root specific in the intact plant and stimulated by wounding in leaf tissue, an especially desirable combination of characteristics for use with an insecticidal or larvicidal gene (see, *EMBO J.* 8(2): 343-350). The TR1 gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US20130117883.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529, herein incorporated by reference). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1093), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed; herein incorporated by reference. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of between about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611, herein incorporated by reference.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724. Such disclosures are herein incorporated by reference.

The above list of selectable marker genes is not meant to be limiting. Any selectable marker gene can be used in the embodiments.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants include but not limited to, stable transformation methods, transient transformation methods, and virus-mediated methods.

"Stable transformation" is as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Bio-technology* 6:923-926) and Led transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the IPD102 polynucleotide or variants and fragments thereof directly into the plant or the introduction of the IPD102 polypeptide transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107: 775-784, all of which are herein incorporated by reference. Alternatively, the IPD102 polynucleotide can be transiently transformed into the plant using techniques involving viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods for the targeted insertion of a polynucleotide at a specific location in the plant genome include the insertion of the polynucleotide at a desired genomic location using a site-specific recombination system. See, for example, WO 1999/25821, WO 1999/25854, WO 1999/25840, WO 1999/25855 and WO 1999/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation include plant transformation vectors that are comprised of more than one contiguous DNA segment. These vectors are often referred to as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one can identify and proliferate the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired IPD102 polypeptide. It is also recognized that such a viral polyprotein, comprising at least a portion of the amino acid sequence of an IPD102 of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules, are known in the art. See, for example, U.S. Pat. Nos. 5,889,191; 5,889,190; 5,866,785; 5,589,367 and 5,316,931; herein incorporated by reference.

Methods for transformation of chloroplasts can be found for example in Svab, et al., (1990) *Proc. Natl. Acad. Sci. USA* 87:8526-8530; Svab and Maliga, (1993) *Proc. Natl. Acad. Sci. USA* 90:913-917; Svab and Maliga, (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci. USA* 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotih*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Evaluation of Plant Transformation

Following introduction of heterologous foreign DNA into plant cells, the transformation or integration of the heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, NY). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled 32P target DNA fragment to confirm the integration of introduced gene into the plant genome according to standard techniques (Sambrook and Russell, (2001) supra).

In Northern blot analysis, RNA is isolated from specific tissues of transformant, fractionated in a formaldehyde agarose gel, and blotted onto a nylon filter according to standard procedures that can be found in Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the IPD102 polypeptide.

Methods to Introduce Genome Editing Technologies into Plants

In some embodiments, the disclosed IPD102 polynucleotide compositions can be introduced into the genome of a plant using genome editing technologies, or previously introduced IPD102 polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed IPD102 polynucleotide has previously been introduced into a genome, genome editing technologies may be used to alter or modify the introduced polynucleotide sequence. Site specific modifications that can be introduced into the disclosed IPD102 polynucleotide compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed IPD102 polynucleotide compositions disclosed herein within the genome of a plant, to generate molecular stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Stacking of Traits in Transgenic Plants

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments, the polynucleotides encoding the IPD102 polypeptide disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to:

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262:1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*), McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including, but are not limited to: insecticidal proteins from *Pseudomonas* sp. such as PSEEN3174 (Monalysin; (2011) PLoS Pathogens 7:1-13); from *Pseudomonas protegens* strain CHAO and Pf-5 (previously *fluorescens*) (Pechy-Tarr, (2008) Environmental Microbiology 10:2368-2386; GenBank Accession No. EU400157); from *Pseudomonas taiwanensis* (Liu, et al., (2010) J. Agric. Food Chem., 58:12343-12349) and from *Pseudomonas pseudoalcaligenes* (Zhang, et al., (2009) Annals of Microbiology 59:45-50 and Li, et al., (2007) Plant Cell Tiss. Organ Cult. 89:159-168); insecticidal proteins from *Photorhabdus* sp. and *Xenorhabdus* sp. (Hinchliffe, et al., (2010) The Open Toxicology Journal, 3:101-118 and Morgan, et al., (2001) Applied and Envir. Micro. 67:2062-2069); U.S. Pat. Nos. 6,048,838, and 6,379,946; a PIP-1 polypeptide of U.S. Pat. No. 9,688,730; an AfIP-1A and/or AfIP-1B polypeptide of U.S. Pat. No. 9,475,847; a PIP-47 polypeptide of US Publication Number US20160186204; an IPD045 polypeptide, an IPD064 polypeptide, an IPD074 polypeptide, an IPD075 polypeptide, and an IPD077 polypeptide of PCT Publication Number WO 2016/114973; an IPD080 polypeptide of PCT Serial Number PCT/US17/56517; an IPD078 polypeptide, an IPD084 polypeptide, an IPD085 polypeptide, an IPD086 polypeptide, an IPD087 polypeptide, an IPD088 polypeptide, and an IPD089 polypeptide of Serial Number PCT/US17/54160; PIP-72 polypeptide of US Patent Publication Number US20160366891; a PtIP-50 polypeptide and a PtIP-65 polypeptide of US Publication Number US20170166921; an IPD098 polypeptide, an IPD059 polypeptide, an IPD108 polypeptide, an IPD109 polypeptide of U.S. Ser. No. 62/521,084; a PtIP-83 polypeptide of US Publication Number US20160347799; a PtIP-96 polypeptide of US Publication Number US20170233440; an IPD079 polypeptide of PCT Publication Number WO2017/23486; an IPD082 polypeptide of PCT Publication Number WO 2017/105987, an IPD090 polypeptide of Serial Number PCT/US17/30602, an IPD093 polypeptide of U.S. Ser. No. 62/434,020; an IPD103 polypeptide of Serial Number PCT/US17/39376; an IPD101 polypeptide of U.S. Ser. No. 62/438,179; an IPD121 polypeptide of US Serial Number U.S. 62/508,514; and δ-endotoxins including, but not limited to a Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of δ-endotoxin polypeptides and the *B. thuringiensis* cytolytic cyt1 and cyt2 genes. Members of these classes of *B. thuringiensis* insecticidal proteins can be found in Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix).

Examples of δ-endotoxins also include but are not limited to Cry1A proteins of U.S. Pat. Nos. 5,880,275, 7,858,849, and 8,878,007; a Cry1Ac mutant of U.S. Pat. No. 9,512,187; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476, 226; Cry1B of U.S. patent application Ser. No. 10/525,318, US Patent Application Publication Number US20160194364, and U.S. Pat. Nos. 9,404,121 and 8,772, 577; Cry1B variants of PCT Publication Number WO2016/61197 and Serial Number PCT/US17/27160; Cry1C of U.S. Pat. No. 6,033,874; Cry1D protein of US20170233759; a Cry1E protein of PCT Serial Number PCT/US17/53178; a Cry1F protein of U.S. Pat. Nos. 5,188,960 and 6,218,188; Cry1A/F chimeras of U.S. Pat. Nos. 7,070,982; 6,962,705 and 6,713,063; a Cry1I protein of PCT Publication number WO 2017/0233759; a Cry1J variant of US Publication US20170240603; a Cry2 protein such as Cry2Ab protein of U.S. Pat. No. 7,064,249 and Cry2A.127 protein of U.S. Pat. No. 7,208,474; a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476, 781, 7,105,332, 7,339,092, 7,378,499, 7,462,760, and 9,593, 345; a Cry9 protein such as such as members of the Cry9A, Cry9B, Cry9C, Cry9D, Cry9E and Cry9F families including the Cry9 protein of U.S. Pat. Nos. 9,000,261 and 8,802,933, and US Serial Number WO 2017/132188; a Cry15 protein of Naimov, et al., (2008) *Applied and Environmental Micro-*

*biology*, 74:7145-7151; a Cry14 protein of U.S. Pat. No. 8,933,299; a Cry22, a Cry34Ab1 protein of U.S. Pat. Nos. 6,127,180, 6,624,145 and 6,340,593; a truncated Cry34 protein of U.S. Pat. No. 8,816,157; a CryET33 and cryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083, 499, 6,548,291 and 6,340,593; a Cry46 protein of U.S. Pat. No. 9,403,881, a Cry 51 protein, a Cry binary toxin; a TIC901 or related toxin; TIC807 of US Patent Application Publication Number 2008/0295207; TIC853 of U.S. Pat. No. 8,513,493; ET29, ET37, TIC809, TIC810, TIC812, TIC127, TIC128 of PCT US 2006/033867; engineered Hemipteran toxic proteins of US Patent Application Publication Number US20160150795, AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of US Patent Application Publication Number 2011/0263488; AXMI046, AXMI048, AXMI050, AXMI051, AXMI052, AXMI053, AXMI054, AXMI055, AXMI056, AXMI057, AXMI058, AXMI059, AXMI060, AXMI061, AXMI067, AXMI069, AXMI071, AXMI072, AXMI073, AXMI074, AXMI075, AXMI087, AXMI088, AXMI093, AXMI070, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI125, AXMI126, AXMI127, AXMI129, AXMI151, AXMI161, AXMI164, AXMI183, AXMI132, AXMI137, AXMI138 of U.S. Pat. Nos. 8,461,421 and 8,461,422; AXMI-R1 and related proteins of US Patent Application Publication Number 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230 and AXMI231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, dsAXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of U.S. Pat. No. 8,461,421; AXMI192 of U.S. Pat. No. 8,461,415; AXMI281 of US Patent Application Publication Number US20160177332; AXMI422 of U.S. Pat. No. 8,252,872; cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710. The Cry proteins MP032, MP049, MP051, MP066, MP068, MP070, MP091S, MP109S, MP114, MP121, MP134S, MP183S, MP185S, MP186S, MP195S, MP197S, MP208S, MP209S, MP212S, MP214S, MP217S, MP222S, MP234S, MP235S, MP237S, MP242S, MP243, MP248, MP249S, MP251M, MP252S, MP253, MP259S, MP287S, MP288S, MP295S, MP296S, MP297S, MP300S, MP304S, MP306S, MP310S, MP312S, MP314S, MP319S, MP325S, MP326S, MP327S, MP328S, MP334S, MP337S, MP342S, MP349S, MP356S, MP359S, MP360S, MP437S, MP451S, MP452S, MP466S, MP468S, MP476S, MP482S, MP522S, MP529S, MP548S, MP552S, MP562S, MP564S, MP566S, MP567S, MP569S, MP573S, MP574S, MP575S, MP581S, MP590, MP594S, MP596S, MP597, MP599S, MP600S, MP601S, MP602S, MP604S, MP626S, MP629S, MP630S, MP631S, MP632S, MP633S, MP634S, MP635S, MP639S, MP640S, MP644S, MP649S, MP651S, MP652S, MP653S, MP661S, MP666S, MP672S, MP696S, MP704S, MP724S, MP729S, MP739S, MP755S, MP773S, MP799S, MP800S, MP801S, MP802S, MP803S, MP805S, MP809S, MP815S, MP828S, MP831S, MP844S, MP852, MP865S, MP879S, MP887S, MP891S, MP896S, MP898S, MP935S, MP968, MP989, MP993, MP997, MP1049, MP1066, MP1067, MP1080, MP1081, MP1200, MP1206, MP1233, and MP1311 of U.S. Ser. No. 62/607,372. The insecticidal activity of Cry proteins can be found for example in van Frannkenhuyzen, (2009) *J. Invert. Path.* 101:1-16). The use of Cry proteins as transgenic plant traits art and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA. (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins can also be expressed in plants such as Vip3Ab & Cry1Fa (US2012/0317682); Cry1BE & Cry1F (US2012/0311746); Cry1CA & Cry1AB (US2012/0311745); Cry1F & CryCa (US2012/0317681); Cry1 DA & Cry1BE (US2012/0331590); Cry1DA & Cry1 Fa (US2012/0331589); Cry1AB & Cry1 BE (US2012/0324606); Cry1Fa & Cry2Aa and Cry1I & Cry1E (US2012/0324605); Cry34Ab/35Ab & Cry6Aa (US20130167269); Cry34Ab/

VCry35Ab & Cry3Aa (US20130167268); Cry1 Da & Cry1Ca (U.S. Pat. No. 9,796,982); Cry3Aa & Cry6Aa (U.S. Pat. No. 9,798,963); and Cry3A & Cry1Ab or Vip3Aa (U.S. Pat. No. 9,045,766). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279 6,137,033, 7,244,820, 7,615,686, and 8,237,020 and the like. Other VIP proteins can be found at lifesci.sussex.ac.uk/home/Neil_Crickmore/Bt/vip.html, which can be accessed on the world-wide web using the "www" prefix. Pesticidal proteins also include Cyt proteins including Cyt1A variants of PCT Serial Number PCT/US2017/000510; Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but not limited to lycotoxin-1 peptides and mutants thereof (U.S. Pat. No. 8,334,366).

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of, Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monoterpene, a sesquiterpene, a steroid, hydroxamic acid, a phenylpropanoid derivative or another non-protein molecule with insecticidal activity.

(F) A polynucleotide encoding an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encoding sequences can be obtained, for example, from the ATCC® under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck, et al., (1993) *Plant Molec. Biol.* 21:673, who provide the nucleotide sequence of the parsley ubi4-2 polyubiquitin gene, and U.S. Pat. Nos. 6,563, 020; 7,145,060 and 7,087,810.

(G) A polynucleotide encoding a molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104: 1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide derivatives of Tachyplesin which inhibit fungal plant pathogens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum.*

(J) A gene encoding a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A gene encoding an insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A gene encoding a virus-specific antibody. See, for example, Tavladoraki, et al., (1993) *Nature* 366:469, who show that transgenic plants expressing recombinant antibody genes are protected from virus attack.

(M) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(N) A polynucleotide encoding a developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2), Pieterse and Van Loon, (2004) *Curr. Opin. Plant Bio.* 7(4):456-64 and Somssich, (2003) *Cell* 113(7):815-6.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. Nos. 09/950,933; 11/619,645; 11/657, 710; 11/748,994; 11/774,121 and U.S. Pat. Nos. 6,891, 085 and 7,306,946. LysM Receptor-like kinases for the perception of chitin fragments as a first step in plant defense response against fungal pathogens (US 2012/ 0110696).

(Q) Detoxification genes, such as for fumonisin, beauvericin, moniliformin and zearalenone and their structurally related derivatives. For example, see, U.S. Pat. Nos. 5,716,820; 5,792,931; 5,798,255; 5,846,812; 6,083,736; 6,538,177; 6,388,171 and 6,812,380.

(R) A polynucleotide encoding a Cystatin and cysteine proteinase inhibitors. See, U.S. Pat. No. 7,205,453.

(S) Defensin genes. See, WO 2003/000863 and U.S. Pat. Nos. 6,911,577; 6,855,865; 6,777,592 and 7,238,781.

(T) Genes conferring resistance to nematodes. See, e.g., PCT Application WO 1996/30517; PCT Application WO 1993/19181, WO 2003/033651 and Urwin, et al., (1998) *Planta* 204:472-479, Williamson, (1999) *Curr Opin Plant Bio.* 2(4):327-31; U.S. Pat. Nos. 6,284,948 and 7,301,069 and miR164 genes (WO 2012/058266).

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent Application Publication US 2009/0035765 and incorporated by reference for this purpose. This includes the Rcg locus that may be utilized as a single locus conversion.

2. Transgenes that Confer Resistance to an Herbicide
   (A) A polynucleotide encoding resistance to an herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605, 011; 5,013,659; 5,141,870; 5,767,361; 5,731,180; 5,304,732; 4,761,373; 5,331,107; 5,928,937 and 5,378, 824; U.S. patent application Ser. No. 11/683,737 and International Publication WO 1996/33270.

(B) A polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566, 587; 6,338,961; 6,248,876; 6,040,497; 5,804,425; 5,633,435; 5,145,783; 4,971,908; 5,312,910; 5,188, 642; 5,094,945, 4,940,835; 5,866,775; 6,225,114; 6,130,366; 5,310,667; 4,535,060; 4,769,061; 5,633, 448; 5,510,471; Re. 36,449; RE 37,287 and 5,491,288 and International Publications EP 1173580; WO 2001/ 66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. Pat. Nos. 7,462,481; 7,405,074 and US Patent Application Publication Number US 2008/ 0234130. A DNA molecule encoding a mutant aroA gene can be obtained under ATCC® Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919, 675; 5,561,236; 5,648,477; 5,646,024; 6,177,616 and 5,879,903, which are incorporated herein by reference for this purpose. Exemplary genes conferring resistance to phenoxy proprionic acids and cyclohexones, such as sethoxydim and haloxyfop, are the Acc1-S1, Acc1-S2 and Acc1-S3 genes described by Marshall, et al., (1992) *Theor. Appl. Genet.* 83:435.

(C) A polynucleotide encoding a protein for resistance to herbicide that inhibits photosynthesis, such as a triazine (psbA and gs+ genes) and a benzonitrile (nitrilase gene). Przibilla, et al., (1991) *Plant Cell* 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC® Accession Numbers 53435, 67441 and 67442. Cloning and expression of DNA coding for a glutathione S-transferase is described by Hayes, et al., (1992) *Biochem. J.* 285:173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) *Mol Gen Genet.* 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687) and genes for various phosphotransferases (Datta, et al., (1992) *Plant Mol Biol* 20:619).

(E) A polynucleotide encoding resistance to an herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,83 and 5,767,373 and International Publication WO 2001/12825.

(F) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide tolerance in plants was first disclosed in WO 2005/107437 (see also, US 2009/0093366). The aad-12 gene, derived from *Delftia acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(G) A polynucleotide encoding an herbicide resistant dicamba monooxygenase disclosed in US Patent Application Publication 2003/0135879 for imparting dicamba tolerance;

(H) A polynucleotide molecule encoding bromoxynil nitrilase (Bxn) disclosed in U.S. Pat. No. 4,810,648 for imparting bromoxynil tolerance;

(I) A polynucleotide molecule encoding phytoene (crtl) described in Misawa, et al., (1993) *Plant J.* 4:833-840 and in Misawa, et al., (1994) *Plant J.* 6:481-489 for norflurazon tolerance.

3. Transgenes that Confer or Contribute to an Altered Grain Characteristic

Such as:

(A) Altered fatty acids, for example, by (1) Down-regulation of stearoyl-ACP to increase stearic acid content of the plant. See, Knultzon, et al., (1992) *Proc. Natl. Acad. Sci. USA* 89:2624 and WO 1999/ 64579 (Genes to Alter Lipid Profiles in Corn).

(2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245).

(3) Altering conjugated linolenic or linoleic acid content, such as in WO 2001/12800.

(4) Altering LEC1, AGP, Dek1, Superal1, mi1 ps, and various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) *Proc. Natl. Acad. Sci.* 92:5620-5624.

(5) Genes encoding delta-8 desaturase for making long-chain polyunsaturated fatty acids (U.S. Pat. Nos. 8,058,571 and 8,338,152), delta-9 desaturase for lowering saturated fats (U.S. Pat. No. 8,063,269), *Primula* A6-desaturase for improving omega-3 fatty acid profiles.

(6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499).

(7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US Patent Application Publication Number 2012/0066794).

(8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904).

(9) Nucleic acid molecules encoding wrinkled1-like polypeptides for modulating sugar metabolism (U.S. Pat. No. 8,217,223).

(B) Altered phosphorus content, for example, by the (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 2005/113778 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. Nos. 6,197,561, 6,291,224, 6,391,348, WO 2002/059324, US Patent Application Publication Number 2003/0079247, WO 1998/45448, WO 1999/55882, WO 2001/04147.

(C) Altered carbohydrates affected, for example, by altering a gene for an enzyme that affects the branching pattern of starch or, a gene altering thioredoxin such as NTR and/or TRX (see, U.S. Pat. No. 6,531,648. which is incorporated by reference for this purpose) and/or a gamma zein knock out or mutant such as cs27 or TUSC27 or en27 (see, U.S. Pat. No. 6,858,778 and US Patent Application Publication Number 2005/0160488, US Patent Application Publication Number 2005/0204418, which are incorporated by reference for this purpose). See, Shiroza, et al., (1988) *J. Bacteriol.* 170:810 (nucleotide sequence of *Streptococcus* mutant fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 1999/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 2000/68393 involving the manipulation of antioxidant levels and WO 2003/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516.

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing or turning "on", the promoter, which in turn allows the gene that, confers male fertility to be transcribed.

(A) Introduction of a deacetylase gene under the control of a tapetum-specific promoter and with the application of the chemical N—Ac-PPT (WO 2001/29237).

(B) Introduction of various stamen-specific promoters (WO 1992/13956, WO 1992/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. Nos. 5,859,341; 6,297,426; 5,478,369; 5,824,524; 5,850,014 and 6,265,640, all of which are hereby incorporated by reference.

5. Genes that Create a Site for Site Specific DNA Integration

This includes the introduction of FRT sites that may be used in the FLP/FRT system and/or Lox sites that may be used in the Cre/Loxp system. For example, see, Lyznik, et al., (2003) *Plant Cell Rep* 21:925-932 and WO 1999/25821, which are hereby incorporated by reference. Other systems that may be used include the Gin recombinase of phage Mu (Maeser, et al., (1991) Vicki Chandler, The Maize Handbook ch. 118 (Springer-Verlag 1994), the Pin recombinase of *E. coli* (Enomoto, et al., 1983) and the R/RS system of the pSRi plasmid (Araki, et al., 1992).

6. Genes that Affect Abiotic Stress Resistance

Including but not limited to flowering, ear and seed development, enhancement of nitrogen utilization efficiency, altered nitrogen responsiveness, drought resistance or tolerance, cold resistance or tolerance and salt resistance or tolerance and increased yield under stress.

(A) For example, see: WO 2000/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801, 104, WO 2000/060089, WO 2001/026459, WO 2001/ 035725, WO 2001/034726, WO 2001/035727, WO 2001/036444, WO 2001/036597, WO 2001/036598, WO 2002/015675, WO 2002/017430, WO 2002/ 077185, WO 2002/079403, WO 2003/013227, WO 2003/013228, WO 2003/014327, WO 2004/031349, WO 2004/076638, WO 199809521.

(B) WO 199938977 describing genes, including CBF genes and transcription factors effective in mitigating the negative effects of freezing, high salinity and drought on plants, as well as conferring other positive effects on plant phenotype.

(C) US Patent Application Publication Number 2004/ 0148654 and WO 2001/36596 where abscisic acid is altered in plants resulting in improved plant phenotype such as increased yield and/or increased tolerance to abiotic stress.

(D) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also see, WO 2002/02776, WO 2003/052063, JP 2002/281975, U.S. Pat. No. 6,084,153, WO 2001/ 64898, U.S. Pat. Nos. 6,177,275 and 6,107,547 (enhancement of nitrogen utilization and altered nitrogen responsiveness).

(E) For ethylene alteration, see, US Patent Application Publication Number 2004/0128719, US Patent Application Publication Number 2003/0166197 and WO 2000/32761.

(F) For plant transcription factors or transcriptional regulators of abiotic stress, see, e.g., US Patent Application Publication Number 2004/0098764 or US Patent Application Publication Number 2004/0078852.

(G) Genes that increase expression of vacuolar pyrophosphatase such as AVP1 (U.S. Pat. No. 8,058,515) for increased yield; nucleic acid encoding a HSFA4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox 1-like (WOX1-like) polypeptide (U. Patent Application Publication Number US 2011/0283420).

(H) Down regulation of polynucleotides encoding poly (ADP-ribose) polymerase (PARP) proteins to modulate programmed cell death (U.S. Pat. No. 8,058,510) for increased vigor.

(I) Polynucleotide encoding DTP21 polypeptides for conferring drought resistance (US Patent Application Publication Number US 2011/0277181).

(J) Nucleotide sequences encoding ACC Synthase 3 (ACS3) proteins for modulating development, modulating response to stress, and modulating stress tolerance (US Patent Application Publication Number US 2010/0287669).

(K) Polynucleotides that encode proteins that confer a drought tolerance phenotype (DTP) for conferring drought resistance (WO 2012/058528).

(L) Tocopherol cyclase (TC) genes for conferring drought and salt tolerance (US Patent Application Publication Number 2012/0272352).

(M) CAAX amino terminal family proteins for stress tolerance (U.S. Pat. No. 8,338,661).

(N) Mutations in the SAL1 encoding gene have increased stress tolerance, including increased drought resistant (US Patent Application Publication Number 2010/ 0257633).

(O) Expression of a nucleic acid sequence encoding a polypeptide selected from the group consisting of: GRF polypeptide, RAA1-like polypeptide, SYR polypeptide, ARKL polypeptide, and YTP polypeptide increasing yield-related traits (US Patent Application Publication Number 2011/0061133).

(P) Modulating expression in a plant of a nucleic acid encoding a Class Ill Trehalose Phosphate Phosphatase (TPP) polypeptide for enhancing yield-related traits in plants, particularly increasing seed yield (US Patent Application Publication Number 2010/0024067).

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/14414 (CON), WO 1996/38560, WO 2001/21822 (VRN1), WO 2000/44918 (VRN2), WO 1999/49064 (GI), WO 2000/46358 (FR1), WO 1997/29123, U.S. Pat. Nos. 6,794,560, 6,307,126 (GAI), WO 1999/09174 (D8 and Rht) and WO 2004/076638 and WO 2004/031349 (transcription factors).

7. Genes that Confer Increased Yield (A) A transgenic crop plant transformed by a 1-Amino-Cyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769).

(B) Over-expression of maize zinc finger protein gene (Zm-ZFP1) using a seed preferred promoter has been shown to enhance plant growth, increase kernel number and total kernel weight per plant (US Patent Application Publication Number 2012/0079623).

(C) Constitutive over-expression of maize lateral organ boundaries (LOB) domain protein (Zm-LOBDP1) has been shown to increase kernel number and total kernel weight per plant (US Patent Application Publication Number 2012/0079622).

(D) Enhancing yield-related traits in plants by modulating expression in a plant of a nucleic acid encoding a VIM1 (Variant in Methylation 1)-like polypeptide or a VTC2-like (GDP-L-galactose phosphorylase) polypeptide or a DUF1685 polypeptide or an ARF6-like (Auxin Responsive Factor) polypeptide (WO 2012/038893).

(E) Modulating expression in a plant of a nucleic acid encoding a Ste20-like polypeptide or a homologue thereof gives plants having increased yield relative to control plants (EP 2431472).

(F) Genes encoding nucleoside diphosphatase kinase (NDK) polypeptides and homologs thereof for modifying the plant's root architecture (US Patent Application Publication Number 2009/0064373).

8. Genes that Confer Plant Digestibility (A) Altering the level of xylan present in the cell wall of a plant by modulating expression of xylan synthase (U.S. Pat. No. 8,173,866).

In some embodiments, the stacked trait may be a trait or event that has received regulatory approval including but not limited to the events with regulatory approval and can be found at the Center for Environmental Risk Assessment (cera-gmc.org/?action=gm_crop_database, which can be accessed using the www prefix) and at the International Service for the Acquisition of Agri-Biotech Applications (isaaa.org/gmapprovaldatabase/default.asp, which can be accessed using the www prefix).

Gene Silencing

In some embodiments, the stacked trait may be in the form of silencing of one or more polynucleotides of interest resulting in suppression of one or more target pest polypeptides. In some embodiments, the silencing is achieved using a suppression DNA construct.

In some embodiments, one or more polynucleotide encoding the polypeptides of the IPD102 polypeptide or fragments or variants thereof may be stacked with one or more polynucleotides encoding one or more polypeptides having insecticidal activity or agronomic traits as set forth supra and optionally may further include one or more polynucleotides providing for gene silencing of one or more target polynucleotides as discussed infra.

"Silencing," as used herein with respect to the target gene, refers generally to the suppression of levels of mRNA or protein/enzyme expressed by the target gene, and/or the level of the enzyme activity or protein functionality. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

"Antisense inhibition" refers to the production of antisense RNA transcripts capable of suppressing the expression of the target protein.

"Antisense RNA" refers to an RNA transcript that is complementary to all or part of a target primary transcript or mRNA and that blocks the expression of a target isolated nucleic acid fragment. The complementarity of an antisense RNA may be with any part of the specific gene transcript, i.e., at the 5' non-coding sequence, 3' non-coding sequence, or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see, Vaucheret, et al., (1998) *Plant J.* 16:651-659 and Gura, (2000) *Nature* 404:804-808).

Another variation describes the use of plant viral sequences to direct the suppression of proximal mRNA encoding sequences (PCT Publication WO 1998/36083).

Recent work has described the use of "hairpin" structures that incorporate all or part, of an mRNA encoding sequence in a complementary orientation that results in a potential "stem-loop" structure for the expressed RNA. In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression, see, Wesley, et al., (2003) *Methods in Molecular Biology, Plant Functional Genomics: Methods and Protocols* 236:273-286.

A construct where the stem is formed by at least 30 nucleotides from a gene to be suppressed and the loop is formed by a random nucleotide sequence has also effectively been used for suppression (PCT Publication WO 1999/61632).

The use of poly-T and poly-A sequences to generate the stem in the stem-loop structure has also been described (PCT Publication WO 2002/00894).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication WO 2002/00904.

RNA interference refers to the process of sequence-specific post-transcriptional gene silencing in animals mediated by short interfering RNAs (siRNAs) (Fire, et al., (1998) *Nature* 391:806). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire, et al., (1999) *Trends Genet.* 15:358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein, et al., (2001) *Nature* 409:363). Short interfering RNAs derived from dicer activity are typically about 21 to about 23 nucleotides in length and comprise about 19 base pair duplexes (Elbashir, et al., (2001) *Genes Dev.* 15:188). Dicer has also been implicated in the excision of 21- and 22-nucleotide small temporal RNAs (stRNAs) from precursor RNA of conserved structure that are implicated in translational control (Hutvagner, et al., (2001) *Science* 293: 834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir, et al., (2001) *Genes Dev.* 15:188). In addition, RNA interference can also involve small RNA (e.g., miRNA) mediated gene silencing, presumably through cellular mechanisms that regulate chromatin structure and thereby prevent transcription of target gene sequences (see, e.g., Allshire, (2002) *Science* 297:1818-1819; Volpe, et al., (2002) *Science* 297: 1833-1837; Jenuwein, (2002) *Science* 297:2215-2218 and Hall, et al., (2002) *Science* 297:2232-2237). As such, miRNA molecules of the disclosure can be used to mediate gene silencing via interaction with RNA transcripts or alternately by interaction with particular gene sequences, wherein such interaction results in gene silencing either at the transcriptional or post-transcriptional level.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, US Patent Application Publication 2009/0188008.

As used herein, a "suppressor enhancer element" comprises a polynucleotide comprising the target sequence to be suppressed or an active fragment or variant thereof. It is recognized that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element.

It is recognized that multiple suppressor enhancer elements from the same target sequence or from different target sequences or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the disclosure have an improved loading of RNAi into the phloem of the plant than would be observed with the expression of the silencing element construct alone and, thus provide better control of phloem feeding insects by an RNAi approach. In specific embodiments, the plants, plant parts and plant cells of the disclosure can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about a 60-70%, about a 70%-80%, about a 80%-90%, about a 90%-100% or greater increase in the level of RNAi in the plant, plant part, plant cell or phloem when compared to an appropriate control. In other embodiments, the increase in the level of RNAi in the plant, plant part, plant cell or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Examples of combined expression of the silencing element with suppressor enhancer element for the control of Stinkbugs and *Lygus* can be found in US Patent Application Publication 2011/0301223 and US Patent Application Publication 2009/0192117.

Some embodiments relate to down-regulation of expression of target genes in insect pest species by interfering ribonucleic acid (RNA) molecules, for example through the expression of dsRNA in a plant or plant cells that are consumed by a herbivorous insect. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including Western corn rootworm to control insect infestation. Furthermore, PCT Publication WO 2009/091864 describes compositions and methods for the suppression of target genes from insect pest species including pests from the *Lygus* genus. Nucleic acid molecules including RNAi for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect R-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publications 2014/0275208 and US2015/0257389 describe polynucleotide silencing elements targeting RyanR and PAT3. PCT Patent Application publication WO2016/138106 describes polynucleotide silencing elements targeting coatomer alpha or gamma. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1a Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Use in Pesticidal Control

General methods for employing strains comprising a nucleic acid sequence of the embodiments or a variant thereof, in pesticide control or in engineering other organisms as pesticidal agents are known in the art.

Microorganism hosts that are known to occupy the "phytosphere" (phylloplane, phyllosphere, rhizosphere, and/or rhizoplana) of one or more crops of interest may be selected. These microorganisms are selected to be capable of successfully competing in the particular environment with the wild-type microorganisms, provide for stable maintenance and expression of the gene expressing the IPD102 polypeptide and desirably provide for improved protection of the pesticide from environmental degradation and inactivation.

Alternatively, the IPD102 polypeptide is produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated IPD102 polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments, the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoe-bicides, pesticides, fungicides, bacteriocides, nematocides, molluscicides or mixtures of several of these preparations, if desired, together with further agriculturally acceptable carriers, surfactants or application-promoting adjuvants can be employed in the formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise, the formulations may be prepared into edible "baits" or fashioned into pest "traps" to permit feeding or ingestion by a target pest of the pesticidal formulation.

Methods of applying an active ingredient or an agrochemical composition that contains at least one of the IPD102 polypeptide produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in each area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that can bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or another buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino] furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethonmethyl, Pirimicarb, Methiocarb; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Suqarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, ε-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments, the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments, the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* JE Smith (fall armyworm); *S. exigua* Hübner (beet armyworm); *S. litura* Fabricius (tobacco cutworm, cluster caterpillar); *Mamestra* configurata Walker (bertha armyworm); *M. brassicae* Linnaeus (cabbage moth); *Agrotis ipsilon* Hufnagel (black cutworm); *A. orthogonia* Morrison (western cutworm); A. *subterranea* Fabricius (granulate cutworm); *Alabama argillacea* Hëbner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira* (Xylomyges) *curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria*

*mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit tortrix moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermuller (European grape vine moth); *Spilonota ocellana* Denis & Schiffermuller (eyespotted bud moth); *Endopiza viteana* Clemens (grape berry moth); *Eupoecilia ambiguella* Hëbner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; and *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); Antheraea pernyi Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hëbner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta*

*absoluta* Meyrick (tomato leafminer); *Yponomeuta padella* Linnaeus (ermine moth); *Heliothis* subflexa Guenée; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape colaspis); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Gehin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other *Brachycera*, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, *phylloxera* from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); Pemphigus spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stål (rice leafhopper); *Nilaparvata lugens* Stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla); *Trioza diospyri* Ashmead (persimmon psylla).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schsffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such as, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Methods for measuring pesticidal activity include for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants employed in the formulation. The coatings may be applied by impregnating propagation material with a liquid formulation or by coating with a combined wet or dry formulation. Examples of the various types of compounds that may be used as seed treatments are provided in *The Pesticide Manual*: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *Bradyrhizobium* spp. (including one or more of *betae, canariense, elkanii, iriomotense, japonicum*, liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, penicillium, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, trichoderma, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments, methods are provided for killing an insect pest, comprising contacting the insect pest, either simultaneously or sequentially, with an insecticidally-effective amount of a recombinant IPD102 polypeptide or IPD102 chimeric polypeptide of the disclosure. In some embodiments, methods are provided for killing an insect pest, comprising contacting the insect pest with an insecticidally-effective amount of a recombinant pesticidal protein of any one of SEQ ID NOs: 1-33 and 65-70 or a variant thereof.

In some embodiments, methods are provided for controlling an insect pest population, comprising contacting the insect pest population, either simultaneously or sequentially, with an insecticidally-effective amount of a recombinant IPD102 polypeptide or IPD102 chimeric polypeptide of the disclosure. In some embodiments, methods are provided for controlling an insect pest population, comprising contacting the insect pest population with an insecticidally-effective amount of a recombinant IPD102 polypeptide of SEQ ID NOs: 1-33 and 65-70 or a variant thereof. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments, methods are provided for controlling an insect pest population resistant to a pesticidal protein, comprising contacting the insect pest population, either simultaneously or sequentially, with an insecticidally-effective amount of a recombinant IPD102 polypeptide or chimeric IPD102 polypeptide of the disclosure. In some embodiments, methods are provided for controlling an insect pest population resistant to a pesticidal protein, comprising contacting the insect pest population with an insecticidally-effective amount of a recombinant IPD102 polypeptide of any one or more of SEQ ID NOs: 1-33 and 65-70 or a variant thereof.

In some embodiments, methods are provided for protecting a plant from an insect pest, comprising expressing in the plant or cell thereof at least one recombinant polynucleotide encoding an IPD102 polypeptide or chimeric IPD102 polypeptide. In some embodiments, methods are provided for protecting a plant from an insect pest, comprising expressing in the plant or cell thereof a recombinant polynucleotide encoding an IPD102 polypeptide of any one or more of SEQ ID NOs: 1-33 and 65-70 or variants thereof.

Insect Resistance Management (IRM) Strategies

Expression of *B. thuringiensis* δ-endotoxins in transgenic corn plants has proven to be an effective means of controlling agriculturally important insect pests (Perlak, et al., 1990; 1993). However, insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way to increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments, the IPD102 polypeptides of the disclosure are useful as an insect resistance management strategy in combination (i.e., pyramided) with other pesticidal proteins include but are not limited to Bt toxins, *Xenorhabdus* sp. or *Photorhabdus* sp. insecticidal proteins, other insecticidally active proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments, the methods of controlling Lepidoptera and/or Coleoptera insect infestation in a transgenic plant and promoting insect resistance management comprises the presentation of at least one of the IPD102 polypeptide insecticidal proteins to insects in the order Lepidoptera and/or Coleoptera.

In some embodiments, the methods of controlling Lepidoptera and/or Coleoptera insect infestation in a transgenic plant and promoting insect resistance management comprises the presentation of at least one of the IPD102 polypeptides of SEQ ID NOs: 1-33 and 65-70, or variants thereof, insecticidal to insects in the order Lepidoptera and/or Coleoptera.

In some embodiments, the methods of controlling Lepidoptera and/or Coleoptera insect infestation in a transgenic plant and promoting insect resistance management comprise expressing in the transgenic plant an IPD102 polypeptide and a Cry protein or other insecticidal protein to insects in the order Lepidoptera and/or Coleoptera having different modes of action.

In some embodiments, the methods of controlling Lepidoptera and/or Coleoptera insect infestation in a transgenic plant and promoting insect resistance management, comprise expression in the transgenic plant of one or more IPD102 polypeptides of SEQ ID NOs: 1-33 and 65-70 or variants thereof and a Cry protein or other insecticidal protein to insects in the order Lepidoptera and/or Coleoptera, where the IPD102 polypeptide and Cry protein have different modes of action.

Also provided are methods of reducing likelihood of emergence of Lepidoptera and/or Coleoptera insect resistance to transgenic plants expressing in the plants insecticidal proteins to control the insect species, comprising expression of an IPD102 polypeptide insecticidal to the insect species in combination with a second insecticidal protein to the insect species having different modes of action.

Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an IPD102 polypeptide and a Cry protein. Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an IPD102 polypeptide of any one of SEQ ID NOs: 1-33 and 65-70 or variants thereof and a Cry protein or other insecticidally active protein.

In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IPD102 polypeptide does not compete with binding sites for Cry proteins in such insects. In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IPD102 polypeptide of any one of SEQ ID NOs: 1-33 and 65-70, or variant thereof does not compete with binding sites for Cry proteins in such insects.

Methods for Increasing Plant Yield

Methods for increasing plant yield are provided. The methods comprise providing a plant or plant cell expressing a polynucleotide encoding at least one of the pesticidal polypeptide sequences disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing an IPD102 polypeptide disclosed herein. Expression of the IPD102 polypeptide results in a reduced ability of a pest to infest or feed on the plant, thus improving plant yield.

Methods of Processing

Further provided are methods of processing a plant, plant part or seed to obtain a food or feed product from a plant, plant part or seed comprising an IPD102 polynucleotide. The plants, plant parts or seeds provided herein, can be processed to yield oil, protein products and/or by-products that are derivatives obtained by processing that have commercial value. Non-limiting examples include transgenic seeds comprising a nucleic acid molecule encoding an IPD102 polypeptide which can be processed to yield soy oil, soy products and/or soy by-products.

"Processing" refers to any physical and chemical methods used to obtain any soy product and includes, but is not limited to, heat conditioning, flaking and grinding, extrusion, solvent extraction or aqueous soaking and extraction of whole or partial seeds.

The following examples are offered by way of illustration and not by way of limitation.

EXAMPLES

Example 1—Identification of an Insecticidal Protein Active Against Western Corn Root Worm (WCRW) from Strain SS530A12-1

The WCRW (*Diabrotica virgifera*) active protein IPD102Aa was identified by protein purification, liquid chromatography mass spectrometry (LC-MS/MS) and PCR cloning from *Pseudomonas vranovensis* strain SS530A12-1 as follows:

*Pseudomonas* Strain SS530A12-1 was grown in LB Broth for 2 days at 26° C. and 250 rpm. Cells were harvested by centrifugation and cell pellets were washed once with phosphate buffered saline (PBS) before storage at −80° C. For protein extraction, cells were thawed and re-suspended in 20 mM Tris-HCl buffer, pH 9 (buffer A) containing protease inhibitor cocktail V from CalBiochem and endonuclease from Epicentre. A crude cleared lysate was obtained by passing the cells through a homogenizer at 30,000 psi, followed by centrifugation at 20,000×g for 10 min.

WCRW bioassays were conducted using 10 microliter samples of the cell lysates mixed with molten low-melt WCRW diet (Southland Products Inc., Lake Village, Arkansas) in a 96 well format. *Diabrotica virgifera* neonates were placed into each well of a 96 well plate. The assay was run for four days at 25° C., and was then scored for insect mortality and stunting of insect growth. The scores were noted as dead, severely stunted (little or no growth but alive), stunted (growth to second instar but not equivalent to controls) or no activity observed.

Genomic DNA from strain SS530A12-1 was extracted with a Sigma Bacterial Genomic DNA Extraction Kit (Cat #NA2110-KT, Sigma-Aldrich, PO Box 14508, St. Louis, MO 63178) according to the manufacturer's instructions. The DNA concentration was determined using a NanoDrop Spectrophotometer (Thermo Scientific, 3411 Silverside Road, Bancroft Building, Suite 100, Wilmington, DE 19810) and the genomic DNA was diluted to 40 ng/ul with sterile water. A 25 ul PCR reaction was set up by combining 80 ng genomic DNA, 2 ul (5 uM) 16S ribosomal DNA primers TACCTTGTTACGACTT (SEQ ID NO: 81) and AGAGTTTGATCMTGGCTCAG (SEQ ID NO: 82), 1 ul 10cmM dNTP, 1× Phusion HF buffer, and 1 unit of Phusion High-Fidelity DNA Polymerase (New England Biolabs, Cat #M0530L, 240 County Road, Ipswich, MA 01938-2723). The PCR reaction was run in MJ Research PTC-200 Thermo Cycler (Bio-Rad Laboratories, Inc., 1000 Alfred Nobel Drive, Hercules, California, 94547, USA) with the following program: 96° C. 1 min; 30 cycles of 96° C. 15 seconds, 52° C. 2 minutes and 72° C. 2 minutes; 72° C. 10 minutes; and hold on 4° C. The PCR products were purified with Qia-Quick DNA purification Kit (Cat #28104, QIAGEN Inc., 27220 Turnberry Lane, Valencia, CA 91355). The purified PCR sample was DNA sequenced and the resulting 16S ribosomal DNA sequence was BLAST searched against the NCBI database which indicated that SS530A12-1 is a *Pseudomonas vranovensis* strain.

Isolated strain SS530A12-1 genomic DNA was also prepared according to a library construction protocol developed by Illumina and sequenced using the Illumina Genome Analyzer IIx (Cat #SY-301-1301, Illumina Inc., 9885 Towne Center Drive, San Diego, CA92121). The nucleic acid contig sequences were assembled and open reading frames were generated.

For purification, cells were thawed and re-suspended in 20 mM Tris-HCl buffer, pH 9 (buffer A) containing protease inhibitor cocktail V from CalBiochem and endonuclease from Epicentre. A crude cleared lysate was obtained by passing the cells through a homogenizer at 30,000 psi, followed by centrifugation at 20,000×g for 20 min. The supernatant was adjusted to pH 8.9 by addition of 1N NaOH. This material was loaded onto a Q-HP HiTrap column (anion exchange, GE Healthcare) and eluted with a linear gradient to 0.35 M NaCl in buffer A. Fractions were desalted and subjected for identification of insecticidal activity.

Active fractions were pooled, buffer exchanged into 1M Ammonium Sulfate, 20 mM Tris-HCl, pH 9 (buffer B) and applied to a Butyl-HP column (hydrophobic interaction, GE Healthcare). The non-binding column flow-through was collected and buffer exchanged into 20 mM Tris-HCl, pH 9 (buffer A). This material was loaded onto a Mono Q column (anion exchange, GE Healthcare). Protein elution was achieved with a salt gradient from 0 to 0.3 M NaCl in buffer A. Active fractions were identified in artificial diet insect feeding assays. Highly enriched, active fractions were analyzed by SDS-PAGE. The candidate protein band was excised, digested with trypsin and analyzed by nano-liquid chromatography/electrospray tandem mass spectrometry (nano-LC/ESI-MS/MS) on a Thermo Q Exactive Orbitrap mass spectrometer (Thermo Fisher Scientific) interfaced with an Eksigent NanoLC 1-D Plus nano-Ic system (AB Sciex). Ten product ion spectra were collected in a data dependent acquisition mode after a MS1 survey scan.

Protein identification was done by database searches using Mascot (Matrix Science). The search against the in-house database identified a novel gene encoded by strain SS530A12-1, which was designated as IPD102Aa.

Example 2—Identification of Homologous Proteins of IPD102Aa

Gene identities may be determined by conducting BLAST (Basic Local Alignment 20 Search Tool; Altschul, et al., (1993) *J. Mol. Biol.* 215:403-410; see also ncbi.nlm.nih.gov/BLAST/, which can be accessed using the www prefix) searches under default parameters for similarity to sequences contained in the publically available BLAST "nr" database (comprising all non-redundant GenBank C0S translations, sequences derived from the 3-dimensional structure Brookhaven Protein Data Bank, the last major release of the 25 SWISS-PROT protein sequence database, EMBL, and DDBJ databases). In addition to public databases, proprietary internal databases were also searched. Certain polynucleotide sequences were analyzed. The resulting percent identity values of IPD102Aa and certain homologous proteins are presented in Table 1.

TABLE 1

| | | | | IPD102Aa homologous proteins and their origins | |
|---|---|---|---|---|---|
| IPD102 Reference | Nucleotide SEQ ID NO | Amino Acid SEQ ID NO | Amino Acid Percent Identity to IPD102Aa | Source | |
| IPD102Aa | 34 | 1 | | Internal strain SSP530A12-1; SSP446D7A; SSP596G8C; SSP587C9-1; SSP433F6-1; SSP283E4-1; JH23761-2; SSP582A8-2; SS145C2; SS165C1; JH75349-2; JH37203-2; JH20756-2; JH75312-2; JH37203-2; JH36773-1; | *Pseudomonas vranovensis* |
| IPD102Ab | 35 | 2 | 99% to IPD102Aa | JH90796-1 | *Pseudomonas vranovensis* |
| IPD102Ac | 36 | 3 | 99.7% to IPD102Aa | XM21_pooled_NODE_1357_58 | |
| IPD102Ea | 37 | 4 | 56.7% to IPD102Aa | internal strain JH87857-2 | *Pseudomonas monteilii* |
| IPD102Eb | 38 | 5 | 50.9% to IPD102Aa | NCBI WP_015268242 hypothetical protein | *Echinicola vietnamensis* |
| IPD102Ec | 39 | 6 | 57.1% to IPD102Aa | WP_056615748 | *Sphingomonas* sp. |
| IPD102Ed | 40 | 7 | 50.2% to IPD102Aa | Internal Strain -AA6350030 | *Granulicella* sp. |
| IPD102Ee | 41 | 8 | 50.2% to IPD102Aa | BAW81060 | *Chromatiaceae bacterium* |
| IPD102Fa | 42 | 9 | 49.7% to IPD102Aa | NCBI WP_027393890 follicular epithelium yolk proteinsubunit | *Aquimarina latercula* |
| IPD102Fb | 43 | 10 | 49.0% to IPD102Aa | NCBI WP_004999216 follicular epithelium yolk protein subunit | *Nitrococcus mobilis* |
| IPD102Fc | 44 | 11 | 46.6% to IPD102Aa | NBCI WP_011306610 follicular epithelium yolk protein subunit | *Methanosarcina barkeri* |
| IPD102Fd | | 12 | 47.1% to IPD102Aa | JGI 2170009770 BMHB3_01721240 hypothetical protein | |
| IPD102Fe | 45 | 13 | 42.7% to IPD102Aa | WP_011033801; WP_048034539; WP_048038039; WP_048044075; WP_048040772 | *Methanosarcina mazei* |
| IPD102Ff | 46 | 14 | 47.0% to IPD102Aa | WP_038257597 | *Yokenella regensburgei* |
| IPD102Fg | 47 | 15 | 43.9% to IPD102Aa | WP_038918640 | *Dickeya* sp. |
| IPD102Fh | 48 | 16 | 44.3% to IPD102Aa | WP_042859453 | *Dickeya* sp. |
| IPD102Fi | 49 | 17 | 46.8% to IPD102Aa | WP_048041904 | *Methanosarcina mazei* |
| IPD102Fj | 50 | 18 | 46.8% to IPD102Aa | WP_048046755 | *Methanosarcina mazei* |
| IPD102Fk | 51 | 19 | 43.9% to IPD102Aa | WP_048177038 | *Methanosarcina barkeri* |
| IPD102Fl | 52 | 20 | 47.9% to IPD102Aa | WP_048178060 | *Methanosarcina* sp. |

TABLE 1-continued

IPD102Aa homologous proteins and their origins

| IPD102 Reference | Nucleotide SEQ ID NO | Amino Acid SEQ ID NO | Amino Acid Percent Identity to IPD102Aa | Source | |
|---|---|---|---|---|---|
| IPD102Fm | 53 | 21 | 50% to IPD102Aa (partial) | A0A0E3LR34 | *Methanosarcina barkeri* |
| IPD102Fn | | 22 | 47.2% to IPD102Aa | WP_054868675 | *Methanosarcina mazei* |
| IPD102Fo | 54 | 23 | 40% to IPD102Aa | internal pool YJP-3_D0530001_NODE_186_185 | |
| IPD102Fp | 55 | 24 | 47.1% to IPD102Aa | WP_048034539 | *Methanosarcina mazei* |
| IPD102Fq | 56 | 25 | 47.1% to IPD102Aa | WP_048038039 | *Methanosarcina mazei* |
| IPD102Fr | 57 | 26 | 47.1% to IPD102Aa | WP_048044075 | *Methanosarcina mazei* |
| IPD102Fs | 58 | 27 | 47.1% to IPD102Aa | WP_048040772 | *Methanosarcina sp.* |
| IPD102Ft | 59 | 28 | 46.8% to IPD102Aa | APJ03582 | *Proteobacteria sp.* |
| IPD102Ga | 60 | 29 | 35% to IPD102Aa | WP_048311487 | *Anaerobacillus macyae* |
| IPD102Gb | 61 | 30 | 34.3% to IPD102Aa | A0A155UFZ2 | *Enterobacter cloacae* |
| IPD102Gc | 62 | 31 | 34.2% to IPD102Aa | A0A093UC85 | *Pectobacterium betavasculorum* |
| IPD102Gd | 63 | 32 | 34% to IPD102Aa | W0HUQ5 | *Sodalis praecaptivus* |
| IPD102Ge | 64 | 33 | 37.5% to IPD102Aa | APJ03924 | *Proteobacteria sp.* |

Example 3—*E. coli* Expression of IPD102Aa and Homologous Proteins

The IPD102Aa gene and its homolog IPD102Ea were amplified by PCR using genomic DNA isolated from strains SS530A12-1 and JH87857-2 with forward and reverse primers listed in Table 2. The resulting PCR products were DNA sequence verified and subcloned into the *E. coli* expression vector pET24a. Homologous genes of IPD102Eb, Fa, Fb, Fc, Fd were synthesized for activity testing.

TABLE 2

Gene cloning primers

| | Forward | Reverse |
|---|---|---|
| IPD102Aa | tatatcatatggctattagtatcgcgatcaatgctgg (SEQ ID NO: 77) | ttggatccttatgaactgatgcccggcctggccgagg (SEQ ID NO: 78) |
| IPD102Ea | tatatcatatgatggctatttcaattaatattgttgc gggac (SEQ ID NO: 79) | Aaggatccttacgaagcaactctcttaacatcaagtt tg (SEQ ID NO: 80) |
| IPD102Eb | | Gene synthesized |
| IPD102Fa | | Gene synthesized |
| IPD102Fb | | Gene synthesized |
| IPD102Fc | | Gene synthesized |
| IPD102Fd | | Gene synthesized | pET24a plasmid DNA, containing a respective IPD102 gene insert, was transformed into competent C41 *E. coli* cells for recombinant protein expression. *E. coli* cells were grown overnight at 37° C. with kanamycin selection and then inoculated to a fresh 2×YT medium (1:25) and further grown to an optical density of about 0.8. At that point cells were chilled in the presence of 0.5 mM ITPG and further grown at 20° C. for 16 hours to induce protein expression. Untagged, N- or C-His 10 tagged proteins were tested for insect activity. The *E. coli* expressed proteins were purified by immobilized metal ion chromatography using Ni-NTA agarose (Qiagen, Germany) according to the manufacturer's protocols.

Example 4—Insecticidal Activity of IPD102Aa and Homologous Proteins

A series of concentrations of the purified IPD102Aa protein and certain homologous proteins were assayed against selected Coleoptera, Lepidoptea and Hemiptera insect species. Concentrations for 50% mortality ($LC_{50}$) or inhibition of 50% of the individuals ($IC_{50}$) were calculated in two independent experiments.

To measure insecticidal activities against Western Corn Root Worm (WCRW)(*Diabrotica virgifera*), bioassays were conducted using 20 ul of the purified protein samples applied topically over 75 ul of artificial WCRW diet (Bio-Serv F9800B based) in each of a 96 well bioassay plate (BD Falcon 353910) then air dried. A variable number of *Diabrotica virgifera* neonates (3 to 9) were placed into each well of the 96 well plate. The assay was run for four days at 25° C. with no light and then scored for mortality and stunting.

Southern Corn Root Worm (SCRW)(*Diabrotica undecimpunctata howardi*), and Northern Corn Root Worm (NCRW, *Diabrotica barben*) were assessed in similar fashion. 20 ul of the purified protein samples were applied topically over 75 ul of artificial SCRW diet (Bio-Serv F9800B based) in each of a 96 well bioassay plate (BD Falcon 353910), and then air dried. A variable number of SCRW (*Diabrotica undecimpunctata howardi*) neonates (3 to 5) were placed into each well of the 96 well plate. The assay was run for four days at 25° C. with no light and then scored for mortality and stunting.

Lepidoptera feeding assays were conducted on an artificial diet in a 96 well plate set up. The respective purified protein was incorporated with the Lepidopteran-specific artificial diet in a ratio of 10 ul protein and 40 ul of diet mixture. Two to five neonate larvae were placed in each well to feed ad libitum for 5 days. Results were expressed as positive for larvae reactions such as stunting and/or mortality. Results were expressed as negative if the larvae were similar to the negative control (i.e., feeding diet to which the above buffer only has been applied).

Southern Green Stink Bug (SGSB, *Nezara viridula*) feeding assays were conducted on an artificial diet. In each assay well, 320 ul of diet were mixed with 80 ul of protein samples. Five insects were infested to each well where the insects were separated from the diet with a parafilm. The assay was run for 5 days and then scored for mortality and stunting.

IPD102Aa was assayed against certain insects selected from Western Corn Root Worm (WCRW)(*Diabrotica virgifera*), Southern Corn Root Worm (SCRW)(*Diabrotica undecimpunctata howardi*), Northern Corn Root Worm (NCRW, *Diabrotica barberi*), European Corn Borer (ECB) (*Ostrinia nubilalis*), Corn Earworm (CEW) (*Helicoverpa zea*), Fall Armyworm (FAW) (*Spodoptera frugiperda*), Soybean Looper (SBL) (*Pseudoplusia includens*), Southern Green Stink Bug (SGSB, *Nezara viridula*) and Western Tarnished Plant Bug (WTPB, *Lygus Hesperus*).

IPD102Ea was assayed against WCRW and NCRW. IPD102Fb was assayed against NCRW, SBL, FAW, CEW, and ECB. IPD102Fc was assayed against SBL, FAW, CEW, and ECB.

TABLE 3

$LC_{50}/IC_{50}$ determination for IPD102Aa and certain homologs

| Sample | LC/IC | On WCRW (ppm) | Lower 95% CL | Upper 95% CL | Slope |
|---|---|---|---|---|---|
| IPD102Aa | LC50 | 16.91 | 0.4878 | 344.1 | |
| | IC50 | 12.85 | 9.347 | 17.84 | 1.978 |
| IPD102Ea | LC50 | 83.55 | 67.51 | 108.74 | 3.23 |
| | IC50 | 32.64 | 27.25 | 38.91 | 4.42 |

| Sample | LC/IC | On NCRW (ppm, 6 d)* | Lower 95% CL | Upper 95% CL |
|---|---|---|---|---|
| IPD102Ea | LC50 | ~172 | | |
| | IC50 | 69.93 | 58 | 83.3 |
| IPD102Fb | LC50 | 21.15 | 17.12 | 25.85 |
| | IC50 | 14.07 | 11.61 | 16.85 |

TABLE 4

Insecticidal activity and spectrum of IPD102Aa

| Insect | IC-50 | LC-50 | ILC50 IPD102Aa | dose tested |
|---|---|---|---|---|
| | | | ppm | |
| SCRW | | | 52 | |
| WTPB | | ~50 | | 200* |
| SGSB | | ~150 | | 3000 |
| SBL | inactive | | | 3000 |
| FAW | inactive | | | 3000 |
| CEW | inactive | | | 3000 |
| ECB | inactive | | | |

*severe stunting at 150 ppm.

IPD102Fb and IPD102Fc demonstrated mild stunting against SBL and CEW at the highest tested concentration of 450 ppm and did not demonstrate activity against FAW and ECB under test conditions at the highest tested concentration of 450 ppm.

IPD102Aa, IPD102Ea, IPD102Eb, IPD102Fa, IPD102Fb, IPD102Fc, and IPD102Fd were assayed in duplicate against SGSB. The estimated LC-50 based on the average efficacy scores for each protein is presented in Table 5.

TABLE 5

IPD102 homolog activity on SGSB

| Protein | Estimated LC-50 | The highest concentration tested |
|---|---|---|
| IPD102Aa | 120 ppm | 200 ppm |
| IPD102Ea | inactive | 100 ppm |
| IPD102Eb | 120 ppm | 200 ppm |
| IPD102Fa | 100 ppm | 200 ppm |
| IPD102Fb | <50 ppm | 200 ppm |
| IPD102Fc | 160 ppm | 200 ppm |
| IPD102Fd | 160 ppm | 200 ppm |

IPD102Aa is a selective insecticidal protein with high potency against several members of the root worm complex under test conditions, reduced potency against two hemipteran insects under test conditions, and no observable potency against four lepidoptean insects under test conditions.

Example 5—IPD102Aa/IPD102Fc Chimera Variants

Chimera variants of IPD102Aa (SEQ ID NO: 1) and IPD102Fc (SEQ ID NO: 11) were created by PCR fragments with 20 base pair overlap at crossover site and using NEBuilder® kit (New England Biolabs Inc, Ipswich, MA) to assemble into full length gene. The variant genes were cloned into pET24 vector and expressed in *E. coli* host as described in Example 3. The *E. coli* cell crude, cleared lysates expressing chimera proteins were used for the WCRW activity assay. Active chimeras were recovered.

TABLE 6

Active chimera sequences aligned with IPD102Aa

|  | AA SEQ ID NO | DNA SEQ ID NO | IPD102Aa | Chimera 1 | Chimera 2 | Chimera 4 | Chimera 1.1 | Chimera 7 | Chimera 8 |
|---|---|---|---|---|---|---|---|---|---|
| IPD102Aa | 1 | 34 |  | 58 | 74 | 91 | 65 | 51 | 60 |
| Chimera 1 | 65 | 71 |  |  | 84 | 48 | 74 | 88 | 79 |
| Chimera 2 | 66 | 72 |  |  |  | 65 | 91 | 77 | 86 |
| Chimera 4 | 67 | 73 |  |  |  |  | 74 | 60 | 69 |
| Chimera 1.1 | 70 | 76 |  |  |  |  |  | 86 | 95 |
| Chimera 7 | 68 | 74 |  |  |  |  |  |  | 91 |
| Chimera 8 | 69 | 75 |  |  |  |  |  |  |  |

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees celsius; and pressure is at or near atmospheric.

That which is claimed is:

1. A polynucleotide encoding an insecticidal polypeptide having at least 98% sequence identity to the polypeptide of SEQ ID NO: 4, operably linked to a heterologous regulatory element.

2. A polynucleotide having at least 98% sequence identity to the polynucleotide of SEQ ID NO: 37, wherein the polynucleotide is operably linked to a heterologous regulatory element.

3. The polynucleotide of claim 1, wherein the polynucleotide has codons optimized for expression in an agriculturally important crop.

4. The polynucleotide of claim 1, further comprising an herbicide resistance gene as a DNA construct.

5. A transgenic plant comprising the polynucleotide of claim 1.

6. A transgenic plant comprising the DNA construct of claim 4.

7. An insecticidal polypeptide having at least 98% sequence identity to the polypeptide of SEQ ID NO:4 joined to a heterologous signal sequence, a transit sequence, or a poly-Histidine tag.

8. The insecticidal polypeptide of claim 7, wherein the insecticidal polypeptide is joined to a heterologous signal sequence or a transit sequence.

9. The insecticidal polypeptide of claim 7, wherein the insecticidal polypeptide is joined to a poly-Histidine tag.

10. A composition comprising at least one insecticidal polypeptide of claim 7.

11. A method of inhibiting growth or killing an insect pest or pest population, the method comprising contacting the insect pest with the insecticidal polypeptide of claim 7.

12. A method of inhibiting growth or killing an insect pest or pest population, the method comprising expressing in a plant the polynucleotide of claim 1.

13. A method for controlling pest infestation, the method comprising providing in the diet of the pest the transgenic plant of claim 5, or a part thereof.

14. A method for improving the yield of a plant, the method comprising growing the transgenic plant of claim 7, wherein the yield of the transgenic plant is increased in the presence of an insect pest relative to a plant that is not transgenic.

15. The method of claim 12, wherein the insect pest or pest population is resistant to at least one Cry insecticidal protein.

* * * * *